(12) United States Patent
Koldiaev et al.

(10) Patent No.: US 10,591,525 B2
(45) Date of Patent: Mar. 17, 2020

(54) WAFER METROLOGY TECHNOLOGIES

(71) Applicant: FemtoMetrix, Inc., Irvine, CA (US)

(72) Inventors: Viktor Koldiaev, Morgan Hill, CA (US); Marc Kryger, Fountain Valley, CA (US); John Changala, Tustin, CA (US)

(73) Assignee: FemtoMetrix, Inc., Irvine, CA (US)

(*) Notice: Subject to any disclaimer, the term of this patent is extended or adjusted under 35 U.S.C. 154(b) by 0 days.

(21) Appl. No.: 15/806,271

(22) Filed: Nov. 7, 2017

(65) Prior Publication Data
US 2018/0217193 A1     Aug. 2, 2018

Related U.S. Application Data

(63) Continuation of application No. 14/690,279, filed on Apr. 17, 2015.
(Continued)

(51) Int. Cl.
*G01R 29/24* (2006.01)
*G01N 21/88* (2006.01)
(Continued)

(52) U.S. Cl.
CPC .......... *G01R 29/24* (2013.01); *G01N 21/636* (2013.01); *G01N 21/8806* (2013.01);
(Continued)

(58) Field of Classification Search
CPC ............................ G01R 29/24; G01R 31/2601; G01R 31/2656; G01N 21/636; G01N 21/8806;
(Continued)

(56) References Cited

U.S. PATENT DOCUMENTS 3,850,508 A * 11/1974 Sittig ................. G01N 21/1717
                                                   356/30
4,286,215 A    8/1981 Miller
(Continued)

FOREIGN PATENT DOCUMENTS

EP    0 378 061    7/1990
EP    0 710 848    5/1996
(Continued)

OTHER PUBLICATIONS

Schaller et al. "Time-Resolved Second Harmonic Generation Near-Field Scanning Optical Microscopy", CHEMPHYSCHEM 2003, 4, pp. 1243-1247.*
(Continued)

*Primary Examiner* — Hina F Ayub
(74) *Attorney, Agent, or Firm* — Knobbe, Martens, Olson & Bear, LLP

(57) ABSTRACT

Various approaches can be used to interrogate a surface such as a surface of a layered semiconductor structure on a semiconductor wafer. Certain approaches employ Second Harmonic Generation and in some cases may utilize pump and probe radiation. Other approaches involve determining current flow from a sample illuminated with radiation. Decay constants can be measured to provide information regarding the sample. Additionally, electric and/or magnetic field biases can be applied to the sample to provide additional information.

32 Claims, 24 Drawing Sheets

Related U.S. Application Data

(60) Provisional application No. 61/980,860, filed on Apr. 17, 2014.

(51) Int. Cl.

| | | |
|---|---|---|
| *G01N 21/95* | (2006.01) | |
| *G01N 21/94* | (2006.01) | |
| *G01R 31/265* | (2006.01) | |
| *G01R 31/26* | (2020.01) | |
| *G01N 27/00* | (2006.01) | |
| *H01L 21/66* | (2006.01) | |
| *G01N 21/63* | (2006.01) | |

(52) U.S. Cl.
CPC ......... *G01N 21/94* (2013.01); *G01N 21/9501* (2013.01); *G01N 27/00* (2013.01); *G01R 31/2601* (2013.01); *G01R 31/2656* (2013.01); *H01L 22/12* (2013.01); *G01N 2201/06113* (2013.01)

(58) Field of Classification Search
CPC .... G01N 21/94; G01N 21/9501; G01N 27/00; G01N 2201/06113; H01L 22/12
USPC ......................................................... 356/237
See application file for complete search history.

(56) References Cited

U.S. PATENT DOCUMENTS

| | | | |
|---|---|---|---|
| 4,291,961 A * | 9/1981 | Takayama | A61B 1/045 396/17 |
| 5,294,289 A | 3/1994 | Heinz et al. | |
| 5,557,409 A | 9/1996 | Downer et al. | |
| 5,814,820 A * | 9/1998 | Dong | G02B 21/16 250/458.1 |
| 6,147,799 A | 11/2000 | MacDonald | |
| 6,321,601 B1 * | 11/2001 | Maris | G01B 11/02 73/655 |
| 6,356,377 B1 | 3/2002 | Bishop et al. | |
| 6,650,800 B2 | 11/2003 | Litvin | |
| 6,795,175 B2 | 2/2004 | Hunt | |
| 6,751,374 B2 | 6/2004 | Wu et al. | |
| 6,781,686 B2 | 8/2004 | Hunt | |
| 6,788,405 B2 | 9/2004 | Hunt | |
| 6,791,099 B2 | 9/2004 | Some et al. | |
| 6,819,844 B2 | 11/2004 | Hunt | |
| 6,856,159 B1 * | 2/2005 | Tolk | G01R 31/311 324/754.23 |
| 6,882,414 B2 | 4/2005 | Hunt | |
| 6,898,359 B2 | 5/2005 | Soljacic et al. | |
| 6,900,894 B2 | 5/2005 | McMillen et al. | |
| 7,158,284 B2 | 1/2007 | Alles et al. | |
| 7,259,868 B2 | 8/2007 | Ozcan et al. | |
| 7,304,305 B2 | 12/2007 | Hunt | |
| 7,324,267 B2 | 1/2008 | Melloni et al. | |
| 7,355,618 B2 | 4/2008 | Seto et al. | |
| 7,433,056 B1 | 10/2008 | Janik | |
| 7,580,138 B2 | 8/2009 | Price | |
| 7,592,828 B2 | 9/2009 | Song | |
| 7,595,204 B2 | 9/2009 | Price | |
| 7,616,307 B2 | 11/2009 | Murtagh et al. | |
| 7,659,979 B2 | 2/2010 | Murtagh et al. | |
| 7,684,047 B2 | 3/2010 | Drake et al. | |
| 7,718,969 B2 | 5/2010 | Zhang et al. | |
| 7,781,739 B1 | 8/2010 | Jannson et al. | |
| 7,830,527 B2 | 11/2010 | Chen | |
| 7,893,703 B2 | 2/2011 | Rzepiela et al. | |
| 7,894,126 B2 | 2/2011 | Gunter et al. | |
| 7,982,944 B2 | 7/2011 | Kippenberg et al. | |
| 8,049,304 B2 | 11/2011 | Srividya et al. | |
| 8,143,660 B2 | 3/2012 | Lee et al. | |
| 8,525,287 B2 | 9/2013 | Tian et al. | |
| 8,573,785 B2 | 11/2013 | Kuksenkov et al. | |
| 8,693,301 B2 | 4/2014 | Knittel et al. | |
| 8,755,044 B2 | 6/2014 | Reich et al. | |
| 9,018,968 B2 | 4/2015 | Huang et al. | |
| 9,194,908 B2 | 11/2015 | Heidmann | |
| 9,285,338 B2 | 3/2016 | Dickerson et al. | |
| 9,652,729 B2 | 5/2017 | Hoffman, Jr. et al. | |
| 9,759,656 B2 | 9/2017 | Ito et al. | |
| 10,371,668 B2 | 8/2019 | Garnett et al. | |
| 2003/0148391 A1 * | 8/2003 | Salafsky | B82Y 30/00 435/7.2 |
| 2003/0190109 A1 * | 10/2003 | Litvin | H04J 14/08 385/15 |
| 2005/0058165 A1 * | 3/2005 | Morehead | H01S 3/08 372/39 |
| 2005/0111002 A1 * | 5/2005 | Ozcan | G01N 21/636 356/432 |
| 2008/0218741 A1 * | 9/2008 | Murtagh | G01N 21/1717 356/73 |
| 2008/0316498 A1 * | 12/2008 | Drake, Jr. | G01N 29/2418 356/502 |
| 2010/0208757 A1 | 8/2010 | Hu | |
| 2010/0272134 A1 | 10/2010 | Blanding et al. | |
| 2011/0125458 A1 | 5/2011 | Xu et al. | |
| 2013/0003070 A1 | 1/2013 | Sezaki et al. | |
| 2013/0050689 A1 * | 2/2013 | Reich | G01N 21/9501 356/237.4 |
| 2013/0257461 A1 * | 10/2013 | Heidmann | G01R 31/2656 324/703 |
| 2015/0330908 A1 | 11/2015 | Koldiaev et al. | |
| 2015/0330909 A1 | 11/2015 | Koldiaev et al. | |
| 2015/0331029 A1 | 11/2015 | Koldiaev et al. | |
| 2015/0331035 A1 | 11/2015 | Koldiaev et al. | |
| 2015/0331036 A1 | 11/2015 | Koldiaev et al. | |
| 2016/0131594 A1 | 5/2016 | Koldiaev et al. | |
| 2017/0067830 A1 | 3/2017 | Adell et al. | |
| 2018/0217192 A1 | 8/2018 | Koldiaev et al. | |
| 2018/0292441 A1 | 10/2018 | Koldiaev et al. | |
| 2018/0299497 A1 | 10/2018 | Koldiaev et al. | |

FOREIGN PATENT DOCUMENTS

| | | |
|---|---|---|
| JP | 2004-226224 | 8/2004 |
| JP | 2008-218957 | 9/2008 |
| TW | 200421460 | 10/2004 |
| TW | 201723467 | 7/2017 |
| WO | WO 00/55885 | 9/2000 |
| WO | WO 02/065108 | 8/2002 |
| WO | WO 2015/161136 | 10/2015 |
| WO | WO 2016/077617 | 5/2016 |
| WO | WO 2017/041049 | 3/2017 |

OTHER PUBLICATIONS

"Rapid Non-destructive Characterization of Trap Densities and Layer Thicknesses in HfO2 Gate Materials Using Optical Second Harmonic Generation", Semicon Korea, Santa Ana, California, Jan. 2016, in 24 pages.

Adell, P. C. et al., "Impact of Hydrogen Contamination on the Total Dose Response of Linear Bipolar Micocircuits", IEEE, Aug. 2007, in 8 pages.

Alles, M. et al, "Second Harmonic Generation for Noninvasive Metrology of Silicon-on-Insulators Wafers", IEEE Transactions on Semiconductor Manufacturing, vol. 20(2), May 2007, pp. 107-113, in 7 pages.

An, Y. et al., "Role of photo-assisted tunneling in time-dependent second-harmonic generation from Si surfaces with ultrathin oxides", Applied Physics Letters, vol. 102, Feb. 4, 2013, pp. 051602-051602-4, in 5 pages.

Bierwagen, O. et al., "Dissipation-factor-based criterion for the validity of carrier-type identification by capacitance-voltage measurements", Applied Physics Letters, vol. 94, Apr. 2009, pp. 152110-152110-3, in 3 pages.

Bloch, J. et al., "Electron Photoinjection from Silicon to Ultrathin SiO2 Films via Ambient Oxygen", Physical Review Letters vol. 77(5), Jul. 29, 1996, pp. 920-923, in 4 pages.

(56) References Cited

OTHER PUBLICATIONS

Campagnola, P., "Second Harmonic Generation Imaging Microscopy: Applications to Diseases Diagnostics", Analytical Chemistry, May 2011, pp. 3224-3231, in 16 pages.
Chang, C. L. et al., "Direct determination of flat-band voltage for metal/high κ oxide/semiconductor heterointerfaces by electric-field-induced second-harmonic generation", Applied Physics Letters vol. 98, Apr. 2011, pp. 171902-171902-3, in 3 pages.
Dautrich, M. et al., "Noninvasive nature of corona charging on thermal Si/SiO2 structures", Applied Physics Letters, vol. 85(10), Sep. 6, 2004, pp. 1844-1845, in 2 pages.
De Vries, J. et al., "Measuring the concentration and energy distribution of interface states using a non-contact corona oxide semiconductor method", Applied Physics Letters, vol. 100, Feb. 24, 2012, pp. 082111-082111-3, in 3 pages.
Dixit, S. K. et al., "Radiation Induced Charge Trapping in Ultrathin HfO2-Based MOSFETs", IEEE Transactions on Nuclear Science, vol. 54(6), Dec. 2007, pp. 1883-1890, in 8 pages.
Erley, G. et al., "Silicon interband transitions observed at Si(100)-SiO2 interfaces", Physical Review B, vol. 58(4), Jul. 15, 1998, pp. R1734-R1737, in 4 pages.
Esqueda, I. et al., "Modeling the Effects of Hydrogen on the Mechanisms of Dose Rate Sensitivity", RADECS 2011 Proceedings—A-1, Sep. 2011, pp. 1-6, in 6 pages.
Fomenko, V. et al., "Optical second harmonic generation studies of ultrathin high-κ dielectric stacks", Journal of Applied Physics, American Institute of Physics, vol. 97(8), Apr. 11, 2005, in 8 pages.
Fomenko, V. et al., "Second harmonic generation investigations of charge transfer at chemically-modified semiconductor interfaces", Journal of Applied Physics, vol. 91(7), Apr. 1, 2002, pp. 4394-4398, in 5 pages.
Geiger, F., "Second Harmonic Generation, Sum Frequency Generation and X(3): Dissecting Environmental Interfaces with a Nonlinear Optical Swiss Army Knife", Annual Review of Physical Chemistry, vol. 60(1), Nov. 2008, pp. 61-83, in 25 pages.
Gielis, J. J. H. et al., "Negative charge and charging dynamics in Al2O3 films on Si characterized by second-harmonic generation", Journal of Applied Physics, American Institute of Physics, vol. 104(7), Nov. 2008, pp. 073701-073701-5, in 6 pages.
Gielis, J. J. H. et al., "Optical second-harmonic generation in thin film systems", Journal of Vacuum Science Technology A, vol. 26(6), Nov./Dec. 2008, pp. 1519-1537, in 20 pages.
Glinka, Y. D. et al., "Ultrafast dynamics of interfacial electric fields in semiconductor heterostructures monitored by pump-probe second-harmonic generation", Applied Physics Letter, vol. 81(20), Nov. 11, 2002, pp. 3717-3719, in 3 pages.
Heinz, T. F. et al., "Optical Second-Harmonic Generation from Semiconductor Surfaces", Advances in Laser Science III, edited by A. C. Tam, J. L. Cole and W. C. Stwalley (American Institute of Physics, New York, 1988) p. 452, in 8 pages.
Istratov, A. et al., "Exponential analysis in physical phenomena", Review of Scientific Instruments, vol. 70(2), , Feb. 1999, pp. 1233-1257, in 25 pages.
Jiang, Y. et al., "Finite difference method for analyzing band structure in semiconductor heterostructures without spurious solutions", Journal of Applied Physics, vol. 116(17), Nov. 2014, pp. 173702-173702-9, in 10 pages.
Jozwikowska, A., "Numerical solution of the nonlinear Poisson equation for semiconductor devices by application of a diffusion-equation finite difference scheme", Journal of Applied Physics, vol. 104, Oct. 2008, pp. 063715-1 to 063715-9, in 10 pages.
Jun, H. et al., "Charge Trapping in Irradiated SOI Wafers Measured by Second Harmonic Generation", IEEE Transactions on Nuclear Science, vol. 51(6), Dec. 2004, pp. 3231-3237, in 8 pages.
Kang, A. Y. et al., "The Radiation Response of the High Dielectric-Constant Hafnium Oxid/Silicon System", IEEE Transactions on Nuclear Science, vol. 49(6), Dec. 2002, pp. 2636-2642, in 7 pages.
Katsube, T. et al., "Memory Traps in MNOS Diodes Measured by Thermally Stimulated Current", Solid State Electronics, vol. 19(1), Jan. 1976, pp. 11-16, in 6 pages.

Koldyaev, V. et al., "Rapid Non-Destructive Detection of Sub-Surface Cu in Silicon-on-Insulator Wafers by Optical Second Harmonic Generation", ASMC, May 2015, in 4 pages.
Lantz, J. et al., "Time-Resolved Optical Second Harmonic Generation Measurements of Picosecond Band Flattening Processes at Single Crystal Ti02 Electrodes", The Journal of Physical Chemistry, vol. 98(38), Sep. 1994, pp. 9387-9390, in 4 pages.
Lei, M. et al., "Hot carrier injection from nanometer-thick silicon-on-insulator films measured by optical second harmonic generation", Applied Physics Letters, vol. 96, Jul. 2010, pp. 241105-241105-3, in 3 pages.
Lundstrom, I. et al., "Tunneling to traps in insulators", Journal of Applied Physics, vol. 43(12), Dec. 1972, pp. 5045-5047, in 4 pages.
Lupke, G. et al., "Electron Trapping in Ultrathin SiO2 on Si(001) Probed by Electric-Field-Induced Second-Harmonic Generation", IEEE Nonlinear Optics: Materials, Fundamentals and Applications-Conference Proceedings, MC22, Aug. 1998, pp. 89-91, in 3 pages.
Mandoc, M. M. et al., "Corona Charging and Optical Second-Harmonic Generation Studies of the Field-Effect Passivation of c-Sl by Al2O3 Films", IEEE, Jul. 2010, in 5 pages.
Marano, S. et al., "Sequential Detection of Almost-Harmonic Signals", IEEE Transactions on Signal Processing, vol. 51(2), Feb. 2003, pp. 395-406, in 12 pages.
Marka, Z. et al., "Band offsets measured by internal photo-emission-induced second-harmonic generation", Physical Review B, vol. 67(4), Jan. 2003, pp. 045302-045302-5, in 6 pages.
Marka, Z. et al., "Band offsets measurement of Si-SiO2 interfaces by internal photoemission induced second-harmonic generation", Physical Review Journal, paper QTuM6, 2003, in 2 pages.
Marka, Z. et al., "Characterization of X-Ray Radiation Damage in Si/SiO2 Structures Using Second-Harmonic Generation", IEEE Transactions on Nuclear Science, vol. 47(6), Dec. 2000, pp. 2256-2261, in 6 pages.
Marka, Z. et al., "Two-color optical technique for characterization of x-ray radiation-enhanced electron transport in SiO2", Journal of Applied Physics, vol. 93(4), Feb. 15, 2003, pp. 1865-1870, in 6 pages.
Mihaychuk, J. G. et al, "Time-dependent second-harmonic generation from the Si-SiO2 interface induced by charge transfer", Optics Letters, vol. 20(20), Oct. 1995, pp. 2063-2065, in 4 pages.
Murzina, T. et al., "Optical Second Harmonic Generation in Semiconductor Nanostructures", Physics Research International, vol. 2012, Mar. 16, 2012, in 12 pages.
Nagel, J. et al., "Solving the Generalized Poisson Equation Using the Finite-Difference Method (FDM)", Feb. 15, 2012, pp. 1-18, in 18 pages.
Neethling, P. H. et al., "Second harmonic generation as a technique to probe buried interfaces", South African Journal of Science, vol. 105, Jul./Aug. 2009, pp. 282-284, in 3 pages.
Park, H. et al., "Total Ionizing Dose Effects on Strained HfO2-Based nMOSFETs", IEEE Transactions on Nuclear Science, vol. 55(6), Dec. 2008, pp. 2981-2985, in 5 pages.
Pasternak, R. et al., "Laser detection of radiation enhanced electron transport in ultra-thin oxides", Nuclear Instruments and Methods in Physics Research A, vol. 514, 2003, pp. 150-155, in 6 pages.
Pedersen, K. et al., "Spectroscopic second-harmonic generation from silicon-on-insulator wafers", Optical Society of America, vol. 26(5), May 2009, pp. 917-922, in 6 pages.
Powell, R. D., "The Use of Photoinjection to Determine Oxide Charge Distributions and Interface Properties in MOS Structures", IEEE Transactions on Nuclear Sciences, vol. 17(6), Jan. 1971, pp. 41-46, in 6 pages.
Price, J. et al., "Charge trapping defects in Si/SiO2/Hf(1-x)SixO2 film stacks characterized by spectroscopic second-harmonic generation", Journal of Vacuum Science and Technology: Part B, AVS/SIP, vol. 29(4), Jul. 2011, pp. 4D101-4D101-11, in 12 pages.
Price, J. et al., "Optical second-harmonic generation study of charge trapping dynamics in HfO2/SiO2 films on Si(100)", Physica Status Solidi, vol. 5(8), Jun. 2008, pp. 2667-2670, in 4 pages.
Rai, V. N. et al., "A transistorized Marx bank circuit providing sub-nanosecond high-voltage pulses", Measurement Science and Technology, vol. 5(4), Nov. 1993, pp. 447-449, in 3 pages.

(56) References Cited

OTHER PUBLICATIONS

Reber, R. et al., "Thermally stimulated current measurements of SiO2 defect density and energy in irradiated metal-oxide-semiconductor capacitors", Review of Scientific Instruments, vol. 63(12), Jun. 4, 1998, pp. 5714-5725, in 13 pages.
Robertson, J., "Band offsets of wide-band-gap oxides and implications for future electronic devices", Journal of Vacuum Science and Technology B, vol. 18(3), May 2000, pp. 1785-1791, in 7 pages.
Shaver, J. et al., "A 2D Finite Difference Simulation to Investigate the High Voltage Blocking Characteristics of 4H-SiC Photoconductive Semiconductor Switches", IEEE, 978-1-4799-8403-9/15, May 2015, pp. 193-195, in 3 pages.
Taguchi, D. et al., "Probing of carrier behavior in organic electroluminescent diode using electric field induced optical second-harmonic generation measurement", Applied Physics Letters, vol. 95, Dec. 30, 2009, pp. 263310-263310-3, in 4 pages.
Ushiki, T. et al., "Evidence of Energetically-Localized Trap-States at SOI-BOX Interface in High-Dose SIMOX Wafers", IEEE International SOI Conference, Oct. 1999, pp. 48-49, in 2 pages.
Vanbel, M. K. et al., "Electric-Field-Induced Second-Harmonic Generation Demonstrates Different Interface Properties of Molecular Beam Epitaxy Grown MgO on Si", The Journal of Physical Chemistry, vol. 118(4), Jan. 2014, in 6 pages.
Vanbel, M. K. et al., "Tunneling of holes is observed by second-harmonic generation", Applied Physics Letters, vol. 102(8), Feb. 2013, in 5 pages.
Vasudevan, V. et al., "A numerical simulation of hole and electron trapping due to radiation in silicon dioxide", Journal of Applied Physics, vol. 70, Nov. 1991, pp. 4490-4495, in 7 pages.
Wang, H. et al., "Non-degenerate fs pump-probe study on InGaN with multi-wavelength second-harmonic generation", Optics Express, Jul. 11, 2005, vol. 13(14), pp. 5245-5252, in 8 pages.
Wang, W. et al., "Coupled Electron-Hole Dynamics at the Si/SiO2 Interface", Physical Review Letters, vol. 81(19), Nov. 9, 1998, pp. 4224-4227, in 4 pages.
White, Y. V. et al., "Studies of charge carrier trapping and recombination processes in Si SiO2 MgO structures using second-harmonic generation", Applied Physics Letters, vol. 88, Feb. 2006, pp. 062102-062102-3, in 3 pages.
Xiao, D. et al., "Optical probing of a silicon integrated circuit using electric-field-induced second-harmonic generation", Applied Physics Letters, vol. 88, Mar. 17, 2006, pp. 114107-114107-3, in 4 pages.
European Extended Search Report dated Feb. 26, 2019 in corresponding EP Application No. 16843152.6.
European Extended Search Report dated Sep. 28, 2017 in corresponding EP Application No. 15779557.6.
European Extended Search Report dated Apr. 3, 2018 in corresponding EP Application No. 15858539.8.
European Office Action dated Aug. 30, 2019 in corresponding EP Application No. 15858539.8.
International Search Report and Written Opinion dated Dec. 21, 2016 in corresponding PCT Application No. PCT/US2016/050286.
International Preliminary Report on Patentability and Written Opinion dated Mar. 6, 2018 in corresponding PCT Application No. PCT/US2016/050286.
Invitation to Pay Addition Fees and Partial Search Report dated Jul. 27, 2015 in corresponding PCT Application No. PCT/US2015/026263.
International Search Report and Written Opinion dated Sep. 23, 2015 in corresponding PCT Application No. PCT/US2015/026263.
International Preliminary Report on Patentability and Written Opinion dated Oct. 27, 2016 in corresponding PCT Application No. PCT/US2015/026263.
International Search Report and Written Option dated Feb. 26, 2016 in corresponding PCT Application No. PCT/US2015/060437.
International Preliminary Report on Patentability and Written Opinion dated May 26, 2017 in corresponding PCT Application No. PCT/US2015/060437.
International Search Report and Written Option dated Aug. 13, 2019 in corresponding PCT Application No. PCT/US2019/029485.
International Search Report and Written Opinion dated Sep. 25, 2019 in corresponding PCT Application No. PCT/US2019/032282.
International Search Report and Written Option dated Aug. 8, 2019 in corresponding PCT Application No. PCT/US2019/029439.
Taiwanese Office Action dated Sep. 28, 2017 in corresponding TW Application No. 105131588.
Taiwanese Office Action dated Jan. 21, 2019 in corresponding TW Application No. 105131588.
U.S. Office Action dated Jul. 13, 2018 in corresponding U.S. Appl. No. 15/256,442.
U.S. Office Action dated Apr. 4, 2019 in corresponding U.S. Appl. No. 15/256,442.
U.S. Office Action dated Jul. 26, 2019 in corresponding U.S. Appl. No. 15/256,442.
U.S. Office Action dated Feb. 8, 2017 in corresponding U.S. Appl. No. 14/690,179.
U.S. Office Action dated Aug. 28, 2017 in corresponding U.S. Appl. No. 14/690,179.
U.S. Office Action dated Jan. 14, 2019 in corresponding U.S. Appl. No. 15/882,433.
U.S. Office Action dated Jul. 25, 2019 in corresponding U.S. Appl. No. 15/882,433.
U.S. Office Action dated Oct. 13, 2016 in corresponding U.S. Appl. No. 14/690,256.
U.S. Office Action dated Jul. 28, 2017 in corresponding U.S. Appl. No. 14/690,256.
U.S. Office Action dated Oct. 31, 2018 in corresponding U.S. Appl. No. 15/880,308.
U.S. Office Action dated May 1, 2017 in corresponding U.S. Appl. No. 14/690,251.
U.S. Office Action dated Jun. 25, 2018 in corresponding U.S. Appl. No. 15/799,594.
U.S. Office Action dated Apr. 17, 2019 in corresponding U.S. Appl. No. 15/799,594.
U.S. Office Action dated Sep. 5, 2019 in corresponding U.S. Appl. No. 15/799,594.
U.S. Office Action dated Oct. 7, 2016 in corresponding U.S. Appl. No. 14/690,279.
U.S. Office Action dated May 8, 2017 in corresponding U.S. Appl. No. 14/690,279.
U.S. Office Action dated Feb. 5, 2018 in corresponding U.S. Appl. No. 14/939,750.
U.S. Office Action dated Jun. 26, 2018 in corresponding U.S. Appl. No. 14/939,750.
U.S. Office Action dated Feb. 13, 2019 in corresponding U.S. Appl. No. 14/939,750.
U.S. Office Action dated Sep. 24, 2019 in corresponding U.S. Appl. No. 14/939,750.

* cited by examiner

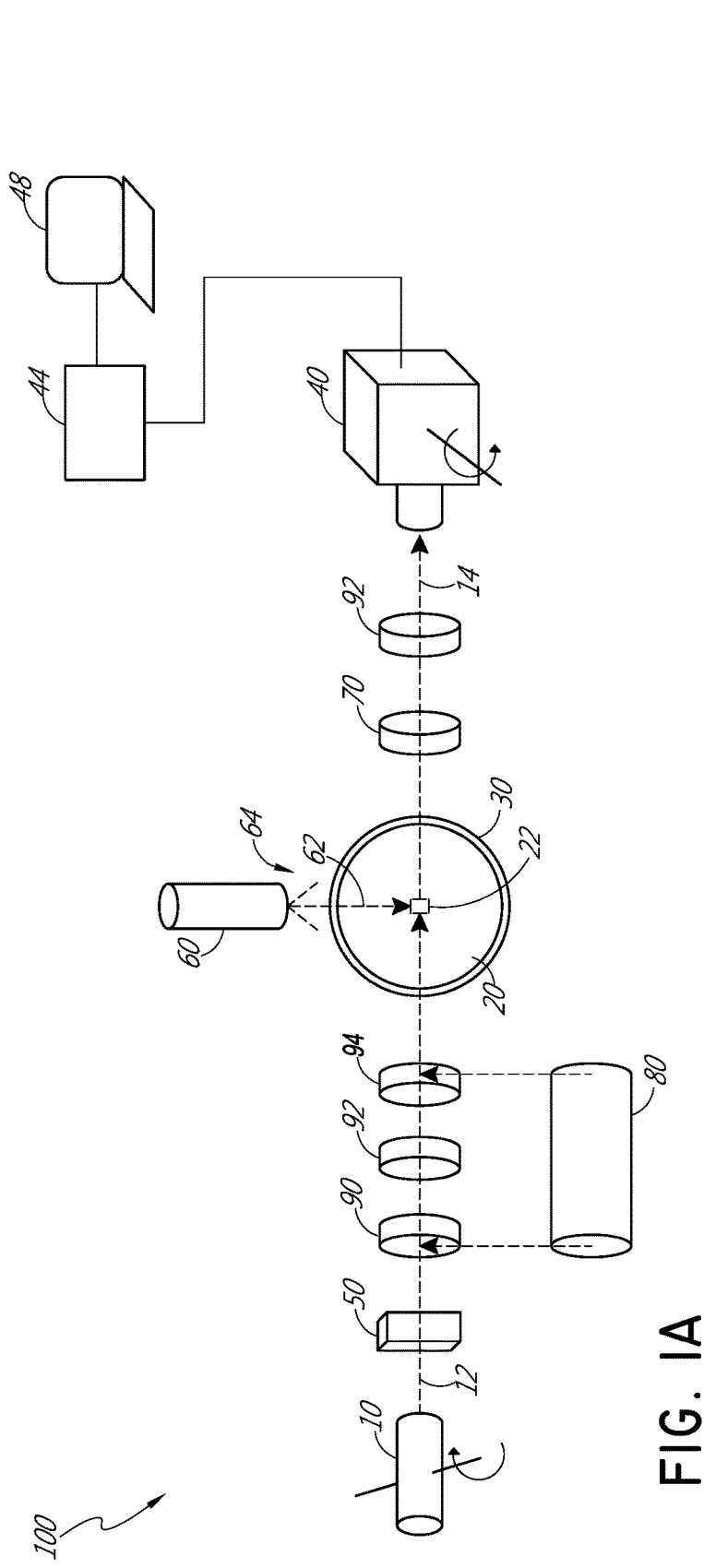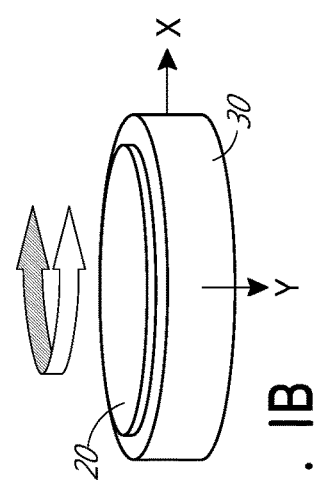
FIG. 1A
FIG. 1B

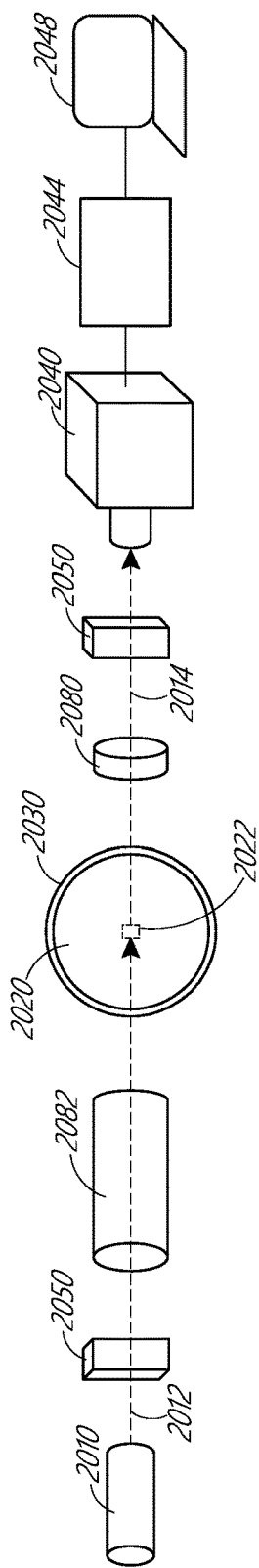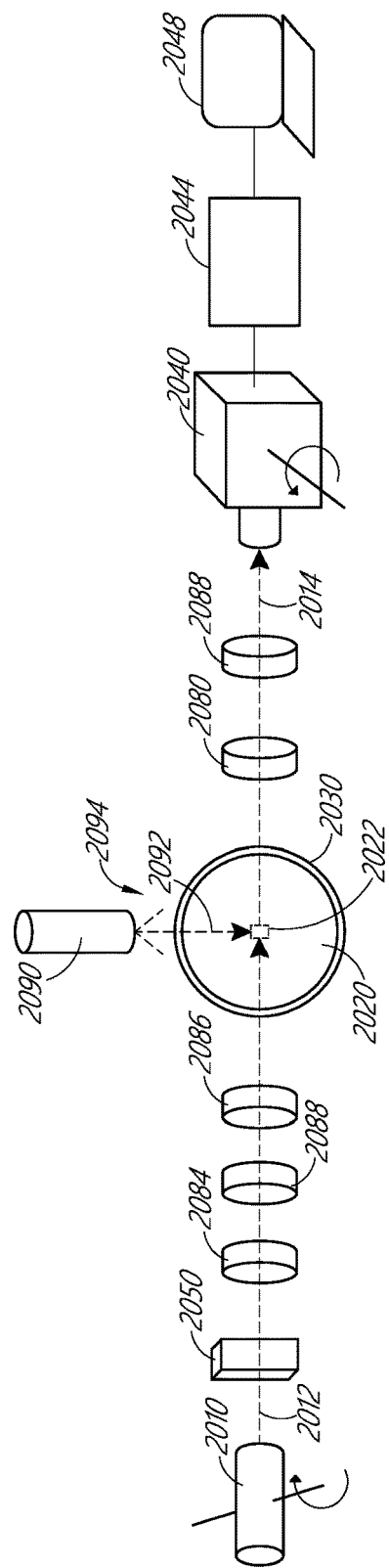
FIG. 6A
FIG. 6B

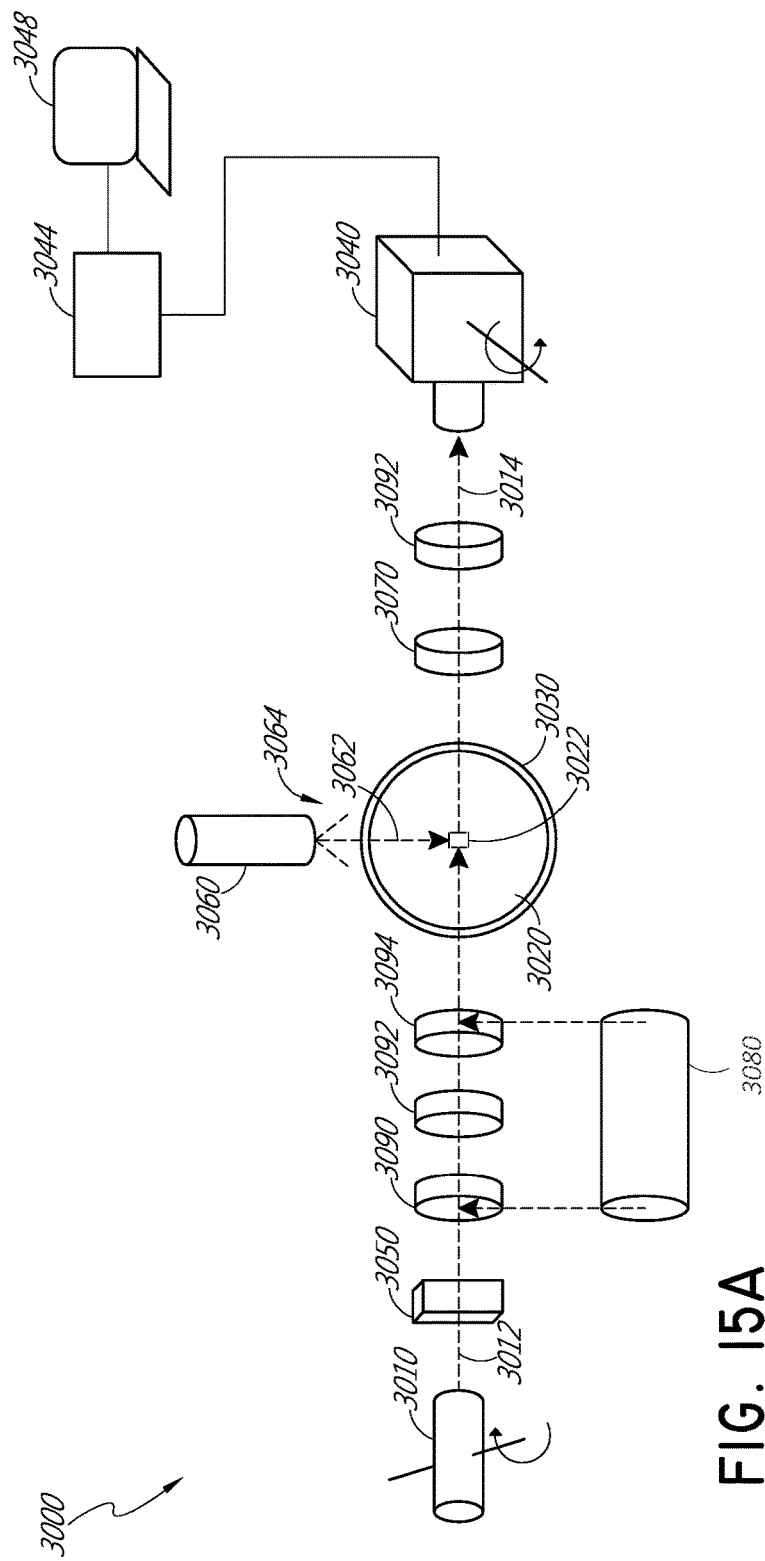
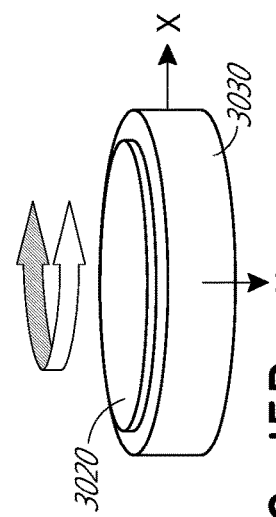
FIG. 15A
FIG. 15B

WAFER METROLOGY TECHNOLOGIES

CROSS-REFERENCE TO RELATED APPLICATIONS

This application is a continuation of U.S. patent application Ser. No. 14/690,279, filed on Apr. 17, 2015, which claims benefit under 35 U.S.C. § 119(e) of U.S. Provisional Application No. 61/980,860, filed on Apr. 17, 2014, titled "WAFER METROLOGY TECHNOLOGIES." Both of the above-identified applications are incorporated by reference herein in its entirety, including but not limited to each of the Sections I, II, III, and IV, of the of U.S. Provisional Application No. 61/980,860 each of which are also incorporated herein by reference in their entirety.

FIELD

The subject filing relates to systems for Second Harmonic Generation (SHG) based wafer inspection, semiconductor metrology, materials characterization, surface characterization and/or interface analysis.

BACKGROUND

In nonlinear optics, light beam input(s) are output as the sum, difference or harmonic frequencies of the input(s). Second Harmonic Generation (SHG) is a non-linear effect in which light is emitted from a material at an angle with twice the frequency of an incident source light beam. The process may be considered as the combining of two photons of energy E to produce a single photon of energy 2E (i.e., the production of light of twice the frequency ($2\omega$) or half the wavelength) of the incident radiation.

A survey of scientific investigations in which the SHG technique has been employed is provided by, "Optical Second-Harmonic Generation from Semiconductor Surfaces" by T. F. Heinz et al., Published in Advances in Laser Science III, edited by A. C. Tam, J. L. Cole and W. C. Stwalley (American Institute of Physics, New York, 1988) p. 452. As reviewed, the SHG process does not occur within the bulk of materials exhibiting a center of symmetry (i.e., in inversion or centrosymmetric materials). For these materials, the SHG process is appreciable only at surfaces and/or interfaces where the inversion symmetry of the bulk material is broken. As such, the SHG process offers a unique sensitivity to surface and interface properties.

So-understood, the SHG effect is described in U.S. Pat. No. 5,294,289 to Heinz et al. Each of U.S. Pat. No. 5,557,409 to Downer, et al., U.S. Pat. Nos. 6,795,175; 6,781,686; 6,788,405; 6,819,844; 6,882,414 and 7,304,305 to Hunt, U.S. Pat. No. 6,856,159 to Tolk, et al. and U.S. Pat. No. 7,158,284 to Alles, et al. also describe other approaches or "tools" that may be employed. Yet, the teachings of these patents appear not to have overcome some of the main obstacles to the adoption of SHG as an established technique for use in semiconductor manufacturing and metrology.

SUMMARY

Part I

An SHG metrology tool is described in which electrons in a layered semiconductor substrate are excited, variously, by each of a pump light source and a probe light source having different power characteristics for the purpose of Sum Frequency Generation (SFG) (e.g., typically SHG). For such an approach, a metrology characterization tool is provided with an "additional" integrated light source (e.g., a UV flash lamp or laser) operating as a "pump" to induce a potential difference across heterointerface(s) in layered semiconductor device templates, together with a short or ultra-short pulsed laser (e.g., a femto-second solid state laser) operating as a "probe" light source. Utility is derived from using the two different sources for different purposes in concert or in conjunction with each other (via various time-offset and/or variable pump energy methods as further described) as distinguished from a single laser SHG or a dual or multiple laser SFG system.

In one method, the pump is employed as a pre-exciting or pre-excitation light source to allow for total characterization time of some materials to be reduced. In many such implementations, the time-dependent electric field is not primarily produced by the probe/probing laser. In one variation of this method, the pump is used to UV flash an entire wafer and then use the probe laser to raster or otherwise scan the entire wafer or some portion thereof spending minimum probe time per point (e.g., scanning as fast as hardware can move the laser). Options in this regard include row-by-row scanning with a step along the (scan) column by wafer shift. Another approach may employ wafer rotating and scanning along the radii.

In another variation, the pump allows a quick charge up of the material interface at a sample site, followed by observation of the decay of that charged interface with the probe in connection with fast-blocking and/or optical delay methods further described in in the portion of U.S. Provisional Application No. 61/980,860, filed on Apr. 17, 2014, titled "WAFER METROLOGY TECHNOLOGIES," referred to as Section II entitled, "CHARGE DECAY MEASUREMENT SYSTEMS AND METHODS". Regardless, in various embodiments, the intent of pump use for pre-excitation is to inject charge carriers into, e.g., the dielectric in a quantity sufficient to impact the interfaces.

In another method, the pump laser is employed as a post-exciting or post-excitation light source to affect an SHG signal already being produced by the probe laser at a sample site. Yet another method employs a compare/contrast of the SHG signal generated by the probe pre- and post-pump laser energy application. By probing the sample and measuring the SHG response prior to pumping, then applying radiation from the pump light source and after that, re-probing, the difference in the SHG response pre- and post-pump can be used to determine additional material properties, such as trap density in the material dielectric.

In various methods discussed herein, a timing differential (i.e., in terms of pre- and/or post-excitation by the pump source in relation to probe laser use) is employed to deliver interrogation curves evincing further information about the material interface.

In various methods, the pump and probe sources are used simultaneously, with the combination used to provide an SHG signal for determining threshold injection carrier energy. Specifically, while probing with the probe laser, a tunable pump laser is ramped-up in frequency. At a particular frequency, the SHG signal exhibits an inflection point (or a region of discontinuity). A value corresponding to the pump laser frequency at the inflection point (or the region of discontinuity) can be related to threshold injection carrier energy.

Various embodiments of the subject pump and probe system offers certain hardware-based advantage possibilities as well. In an example where the pump is a flash lamp, highly relevant cost savings can be achieved relative to 2-laser systems. Whether provided as a flash lamp or a second laser, the combination of a pump and probe as contemplated herein can also reduce the risk of optical damage to the substrate to be interrogated because illumination that is too powerful will degrade the dielectrics and even substrate if a threshold average power is exceeded. The threshold average power that causes optical damage to the substrate can be determined by experimental calibration study.

To understand the latter possibility in connection with the subject hardware some background is provided. Namely, both pump and probe energies, alone, are capable of producing an SHG signal with such hardware. While the pump and probe sources do not need to operate in conjunction to produce SHG signal, relevant material properties are derived in the subject methods primarily from the SHG intensity produced by the probe, as the pump will generally not have the peak power to drive buried interfacial SHG appropriately. Time-dependent SHG intensity curves will change based on the distribution of charge carriers across an interface, for example, between the dielectric and substrate. The time it takes for injection of carriers across an interface, for example, between the dielectric and a semiconductor substrate, is dependent upon the average power targeted on the sample. In some implementations, the probe alone can enable injection of carriers across an interface between the dielectric and substrate. In such implementations due to the inability to decouple average power from peak power, the time taken to reach the target average power that allows for injection of carriers across an interface between the dielectric and substrate without exceeding the optical damage threshold of a material may be greater than implementations using a combination of pump and probe. By using a high average power but low peak power optical source as a pump to inject carriers across an interface between the dielectric and substrate prior to probing, the time savings of increased average power can be had without the potential damage complications a high peak power at said average power may induce.

Accordingly, as compared to the pump, the subject probe is typically a higher peak power source with low average power. Stated otherwise, the probe laser is typically relatively very weak. In one aspect, this allows for minimal disturbance to the native electric field present at the substrate interface to yield an initial time-independent signal.

With higher average power but low peak power, the pump induces an electric field (E) by causing charge carriers to jump up in energy level at the material interface or across the interface. By using a relatively high average power source as the pump and quickly "charging up" the interface by giving all the available electrons the energy at least sufficient to jump into the dielectric, a situation is created where the high peak power (providing high SHG conversion rates) but low average power (due to short pulse duration and limited number of such pulses) probe laser can quickly interrogate the surface to provide time-independent SHG signal data.

Accordingly, in various embodiments described herein a reduction in the time required for a/the probe laser to move electrons to higher energy levels or across interfaces can be achieved which can allow for faster evaluations of a steady-state SHG signal and/or charge carrier time dynamics measurements. This approach also allows for separating the effects of the SHG probe from its own influence on the electric field at substrate interfaces. It also allows time-dependence in the SHG process to be sped up or ignored as well as allowing for faster acquisition of time-independent SHG data over at least part of an acquired signal from the probe beam. Likewise, another aspect allows for faster and/or more accurate determination of threshold energy for carrier injection into an interface (e.g., interface between a semiconductor and a dielectric), as well as fast(er) throughput in a line tool environment. Whatever the context, the available time reduction offered can advantageously facilitate high throughput testing in any sort of in-line metrology tool in the semiconductor industry. By way of example, to generate time dependence curves using pre-existing application of the SHG technique on a device including a 25 nm buried oxide layer under a 10 nm Silicon on Insulator (10 nm device layer/25 nm BOX SOI) takes 6 to 12+ seconds per point. Using pre-excitation as described herein, time dependence can be generated in under 1 second, pending material and pump/probe power. This advance would enable a 10×+ surface area covered on a wafer given available time/wafer on the line, or enable equivalent confidence in 10% of the time. And while these sort of numbers will vary based on material, layer thickness and specific pump/probe power and wavelength, they should be illuminating.

All said, invention embodiments hereof include each of the methodology associated with the approaches described herein, alone or in combination with elements components or features from the different parts of this application, the referenced co-pending patent applications, and any documents incorporated by reference herein, hardware to carry out the methodology, productions systems incorporating the hardware and products (including products-by-process) thereof.

Part II

To date, there has been limited adoption of SHG-based metrology tools. It is believed that this fact stems from an inability of existing systems to make distinctions between detected interfacial properties. In other words, while existing SHG techniques offer means of determining location and presence of interfacial electrically active anomalies, their methods rely on relative measurements and are not practically able to parse between electrically active anomaly types (e.g., gettered contaminants such as copper vs. bond voids) and/or to quantify detected contaminants.

However, the subject systems and methods variously enable capturing the quantitative information for making the determinations required for such activity. In these systems and methods, after charging a wafer sample with optical electro-magnetic radiation (at a specific site with a pulsed laser or with a flash lamp or other electro-magnetic energy source or light source or other means) a plurality of measurements are made to monitor transient electric field decay associated with heterointerfaces controlling the decay period.

Using decay curve data generated and characterized with multiple points, spectroscopic parameters of an anomaly or problem at a sample site can be determined such that differentiation and/or quantification of defect type or contaminant(s) is possible. In all, the decay dependent data is collected and used to provide systems by which charge carrier lifetimes, trap energies and/or trapped charge densities may be determined in order that defects and contaminants can be discerned or parsed from one another, for species differentiation if a contaminant is detected and/or for contaminant quantification if detected.

Such activity is determined on a site-by-site basis with the selected methodology typically repeated to scan an entire wafer or other material sample or region thereof. As for the computer processing required to enable such determination, it may occur in "real time" (i.e., during the scanning without any substantial delay in outputting results) or via post-processing. However, in various embodiments, control software can run without lag in order to provide the precise system timing to obtain the subject data per methodology as described below.

Optionally, sample material charge-up is monitored in connection with SHG signal production. In which case, the information gained via this signal may be employed in material analysis and making determinations.

In any case, system embodiments may include an ultra-short pulse laser with a fast shutter operating in the range of $10^2$ seconds to picosecond ($10^{-12}$ seconds) range. Such systems may be used to monitor SHG signal generation at a sample site from surface and buried interfaces of thin film materials after the introduction of a plurality of short blocking intervals. These intervals may be timed so as to monitor the field decay of interest.

The subject systems may also include an optical line delay. The delay line may be a fiber-based device, especially if coupled with dispersion compensation and polarization control optics. Alternatively, the delay line may be mirror-based and resemble the examples in U.S. Pat. No. 6,147,799 to MacDonald, U.S. Pat. No. 6,356,377 to Bishop, et al. or U.S. Pat. No. 6,751,374 to Wu, et al. In any case, the delay is used in the system in order to permit laser interrogation of the material in the picosecond ($10^{-12}$ second) to femtosecond ($10^{-15}$ second) and, possibly, attosecond ($10^{-18}$ second) ranges. Such interrogation may be useful in detecting multiple charge decay-dependent data points along a single decay curve.

The subject methods include one that involves measuring an SHG signal for decay data points acquired after successive charge-up events. The conditions for obtaining a SHG signal may be different at each charge-up event. Additionally, the time interval between successive charge-up events may be different. In this method, the multiple data points (at least two but typically three or more) can be correlated and expressed as a single composite decay curve. Another method employs minimally disruptive (i.e., the radiation used to produce the SHG signal does not significantly recharge the material) SHG signal interrogation events after a single charging event.

Yet another method for determining transient charge decay involves measuring discharge current from the sample material (more accurately, its structures that were charged by optical radiation). The time dependence (kinetics) of this signal may then be treated in the same way as if SHG sensing had been employed. Further, as above, such sensing may be done in the span of one decay interval and/or over a plurality of them following charge to a given level. In any case, electrode-specific hardware for such use is detailed below.

Regarding charge or charging level, this may be taken to a point of apparent saturation when charge dynamics are observed in standard linear time or against a log time scale. Per above, the subject methodologies optionally observe, record and analyze charging kinetic as this may yield important information.

For successive charge/interrogation events, if an initial charge state of a sample is measured and the saturation level is not far from the initial charge state, the system may omit further or subsequent characterization. In this context, what may be regarded as "not far" may mean about 1% to about 10% of charge increase versus the initial charge state to be determined by learning when the subject tool is used for a given time of sampling.

Stated otherwise, so-called "saturation" is a relative term. Using a linear time scale, material will appear saturated very quickly. But if an SHG signal intensity associated with charging is observed in log scale from 10-100 seconds, it can be observed that the later part of saturation occurs with a different time constant and is relatively more gradual or time-consuming. Thus, while examples of the methodology provided herein discuss charging to saturation, the delay and other timing may be regarded as occurring with respect to apparent saturation. Rather than waiting the full amount of time for 100% saturation, as this may be unnecessarily time consuming to reach, instead, the instrument may delay until the time it takes to get to apparent saturation or the time in which can extract important parameters, regardless of how long it takes for full saturation.

Further, it is to be understood that when monitoring the amount or degree of charge-up toward saturation (e.g., in connection with SHG monitoring), the subject methods and systems may operate with charge and/or re-charging levels at less than saturation (as discussed above) while still yielding meaningful decay curve information. Without such measurement, however, when approximate saturation is a known parameter (e.g., by experience with the subject tool with a given material) charge to saturation is employed as the target level.

Notably, various interfacial material properties may also be determined using laser beam blocking or delay as further described in the portion of U.S. Provisional Application No. 61/980,860, filed on Apr. 17, 2014, titled "WAFER METROLOGY TECHNOLOGIES," referred to as Section III, titled "TEMPERATURE-CONTROLLED METROLOGY," which is incorporated herein by reference in its entirety. Introducing a DC bias across the sample being tested can also assist in analysis of the material. Employing a DC bias actively changes the initial charge distribution at the interfaces before photo-induced voltage has any effect. To do so, the sample being tested may be mounted atop a conductive chuck which can be used as a ground for DC biasing across the sample using sample top surface probes. Other means of introducing induced voltage biases are possible as well without the use of surface probes as further described in the portion of U.S. Provisional Application No. 61/980,860, filed on Apr. 17, 2014, titled "WAFER METROLOGY TECHNOLOGIES," referred to as Section IV entitled, "FIELD-BIASED SHG METROLOGY".

Also, the subject systems may use a secondary light source in addition to the primary laser involved in blocking-type analysis for charge decay determination. Such a set of sources may be employed as a radiation pump/probe combination as further described in the portion of U.S. Provisional Application No. 61/980,860, filed on Apr. 17, 2014, titled "WAFER METROLOGY TECHNOLOGIES," referred to as Section I entitled, "PUMP AND PROBE TYPE SHG METROLOGY".

All said, invention embodiments hereof include each of the methodology associated with the approaches described herein, alone or in combination with elements components or features from the different parts of this application, the referenced co-pending patent applications, and any documents incorporated by reference herein, hardware to carry out the methodology, productions systems incorporating the hardware and products (including products-by-process) thereof.

Part III

Various field-biased (e.g., magnetic-field biases, DC bias and/or voltage bias induced by an AC field alone, with a capacitive coupling and/or a changing magnetic field) SHG-based systems and their methods of use are described. These are treated in turn. They may be used independently and/or in a combined system. Various embodiments described herein include each of the methodology associated with the approaches described above, hardware to carry out the methodology, productions systems incorporating the hardware and products (including products-by-process) thereof.

Magnetic Field Bias

A static or changing magnetic field applied to the sample will cause the second order optical susceptibility tensor of a material to change. Thus, a magnetic field could be used to increase SHG signal from the sample, to an optimum value. Moreover, a changing magnetic field can be used to induce bias as further discussed below.

Induced Voltage Bias for Eliminating DC Contact Probes

Systems and methods are described for characterizing the SHG response of a layered semiconductor material that is subjected to a discrete electric field across its interfaces without use of contact bias probes in a system that can synchronize the pulses of a probing laser and/or the gating of a detector with a predetermined amplitude of voltage of an AC, variable or pulsed bias applied to the sample to produce a corresponding or coordinated induced voltage field at the surface to be interrogated.

The subject hardware comprises an SHG apparatus (e.g., further described in the portion of U.S. Provisional Application No. 61/980,860, filed on Apr. 17, 2014, titled "WAFER METROLOGY TECHNOLOGIES," referred to as Section II titled, "CHARGE DECAY MEASUREMENT SYSTEMS AND METHODS") together with a means of inducing (e.g., a component configured to induce) a voltage at or along the "device" surface of a sample without contact. Such means or component may be either via backside contact with probes or a conductive chuck, involving capacitively coupled probes connected to a power source also in communication with backside contact probes or such a chuck, or by applying a changing magnetic field to the sample, with the purpose of inducing an external voltage field across its multilayer interfaces.

A transient electric field produced by a variable waveform (optionally AC) power supply (via any of the approaches above) induces an electric field across the interfaces of the multilayer semiconductor material. The relationship between the voltage and the material interface electrical field may be modeled by a transfer function or otherwise, including by accounting for various (capacitive or otherwise) external influences. The output of this function, given a particular amplitude and frequency of AC (or other) current, may be employed as a timing cue to trigger the laser shutter and/or photon counter simultaneously for SHG characterization of the testing point for constant near-instantaneous values of the electric field amplitude at the interfaces. As such, the system is able to simulate a constant (DC) voltage applied topside (i.e., at the device layer of the substrate) via contact electrical probes.

With direct application of AC to the backside of the sample, the system begins with the chuck at a 'neutral' or ground state, and bulk and device layers at an equilibrium potential. Then, an alternating bias is applied to the chuck, which is in galvanic contact with the bulk, or substrate layer of the multilayered semiconductor material. Since the device layer is separated from the bulk by the buried oxide layer, and not directly connected with a conductor, an electric potential field, or voltage will be created (i.e., induced) between the device and bulk layers.

Alternatively, capacitively coupled probe(s) that reside near (within about 1 to about 2 mm) but without touching the top side of the sample may be employed. A preferred approach in this regard may be a plate sized to cover (but not touch) the entire wafer, hovering with a small hole for the incident laser to pass through on its way to the sample and for the SHG beam to pass through on its way out of the sample.

In some implementations, a non-contacting electrode can be implemented using MEMS technology. For example, in an implementation, a Si wafer can be oxidized on both sides. A spiral or a grid-like electrode can then be placed by deposition on one or more locations of the wafer. The oxide material can be removed from the back-side of the wafer at those locations. An electro-magnetic field applied to the electrode can inductively bias the wafer in such implementations through near-field inductive coupling. The magnetic field produced by an external electric current can be used to generate an electric current across the wafer by inducing a current in the deposited electrode. Other methods of implementing non-contacting probes can also be used.

In any case, SHG methodology is used to interrogate the sample, for example, as further described in the portion of U.S. Provisional Application No. 61/980,860, filed on Apr. 17, 2014, titled "WAFER METROLOGY TECHNOLOGIES," referred to as Section I titled, "PUMP AND PROBE TYPE SHG METROLOGY" and/or Section III, titled "TEMPERATURE-CONTROLLED METROLOGY," both of which are incorporated herein by reference in their entirety. The same holds true with respect to the other embodiments discussed below.

Regardless, in the subject embodiments, since it is desirable to monitor SHG as a function of the voltage across the interfaces, the SHG signal will be synchronized with the power supply. This synchronization can be accomplished by controlling the laser(s) used for SHG signal production and SHG signal processing software, the laser(s) alone, or only the SHG signal processing software, in time with voltage changes. The voltage of the chuck can also be controlled.

An advantage of this synchronization is that voltage biased SHG measurements can be obtained that would be similar to DC biased SHG measurements, without using contact voltage bias probes on the front surface of the wafer. Instead of applying a DC bias, the system would use an AC bias synchronized with SHG measurement and/or generation to collect SHG data at discrete points on the voltage cycle. The AC bias could be applied using near-field inductive coupling, or via capacitive coupling of the sample. SHG data collected with these biasing techniques would yield the same material properties information as DC biased SHG.

To reduce or minimize noise and obtain statistically relevant indicator(s) of SHG intensity as a function of voltage across the interfaces, multiple photon counting windows may be desirable as further described below.

Induced Voltage Bias for Characterizing Interfacial Leakage

Systems and methods are described for characterizing interfacial leakage current and/or carrier injection energies between layers of layered (e.g., semiconductor) materials using SHG and a voltage change (such as an alternating, variable and/or pulsed voltage or current signal or a device that changes magnetic field in a manner to induce voltage change in a device layer of a sample) applied to the layered semiconductor material as per above.

By measuring the SHG response from optical pulses generated by a pulsed laser directed at a layered semiconductor/dielectrics structure while or shortly after an alternating, variable or pulsed voltage is applied to the layered semiconductor material, interfacial leakage current and/or carrier injection energies between layers can be characterized. In some embodiments, the time evolution of the SHG signal from interfaces as a function of the time constant of decay of the induced voltage can be measured. This yields information about charge carrier mobility across the interfaces.

Induced Voltage Bias for Characterizing Threshold Carrier Injection Energy

Systems and methods are described for SHG measurement applied in connection with a varied electrical field at a sample device layer in lieu of using tunable wavelength laser excitation to determine energy thresholds for photo-induced charge carrier injection into the dielectric in a layered semiconductor material. More specifically, to measure the threshold energy necessary for photo-induced charge carrier injection into the dielectric one can expose the material to a substantially monochromatic incident photon beam for SHG production and then incrementally change voltage across an interface of the exposed layered semiconductor material, measuring SHG signal count at each incremental voltage change until the SHG response has significant inflection or discontinuity or sudden change in slope from prior measurements. This change in slope could be a maximum or minimum (e.g., local maximum or minimum) or cusp, or step function, etc. The net charge change transfer due to all these processes can be described as the integral of the contributions of the 3rd harmonic injection current, "forward" leakage current to the dielectric due to the strong electric field, and "backward" discharge leakage current. Put in equation form: $Q(t)=\int(I_X+I_E-I_L)dt$ Kinetic features of this curve shape (bending moment and saturation moments of time) will then provide information for determining threshold carrier injection energy.

All said, invention embodiments hereof include each of the methodology associated with the approaches described herein, alone or in combination with elements components or features from the different parts of this application, the referenced co-pending patent applications, and any documents incorporated by reference herein, hardware to carry out the methodology, productions systems incorporating the hardware and products (including products-by-process) thereof.

BRIEF DESCRIPTION OF THE DRAWINGS

The figures diagrammatically illustrate aspects of various embodiments of different inventive variations.

FIG. 1A is a diagram of an SHG metrology system embodiment hereof; FIG. 1B is a perspective view of a chuck for use in such an SHG system.

FIGS. 6A-6C are diagrams of systems embodiments;

FIGS. 15A and 15B are schematic diagrams of SHG system components as may be used herein.

DETAILED DESCRIPTION

Part I

Figure 1C:
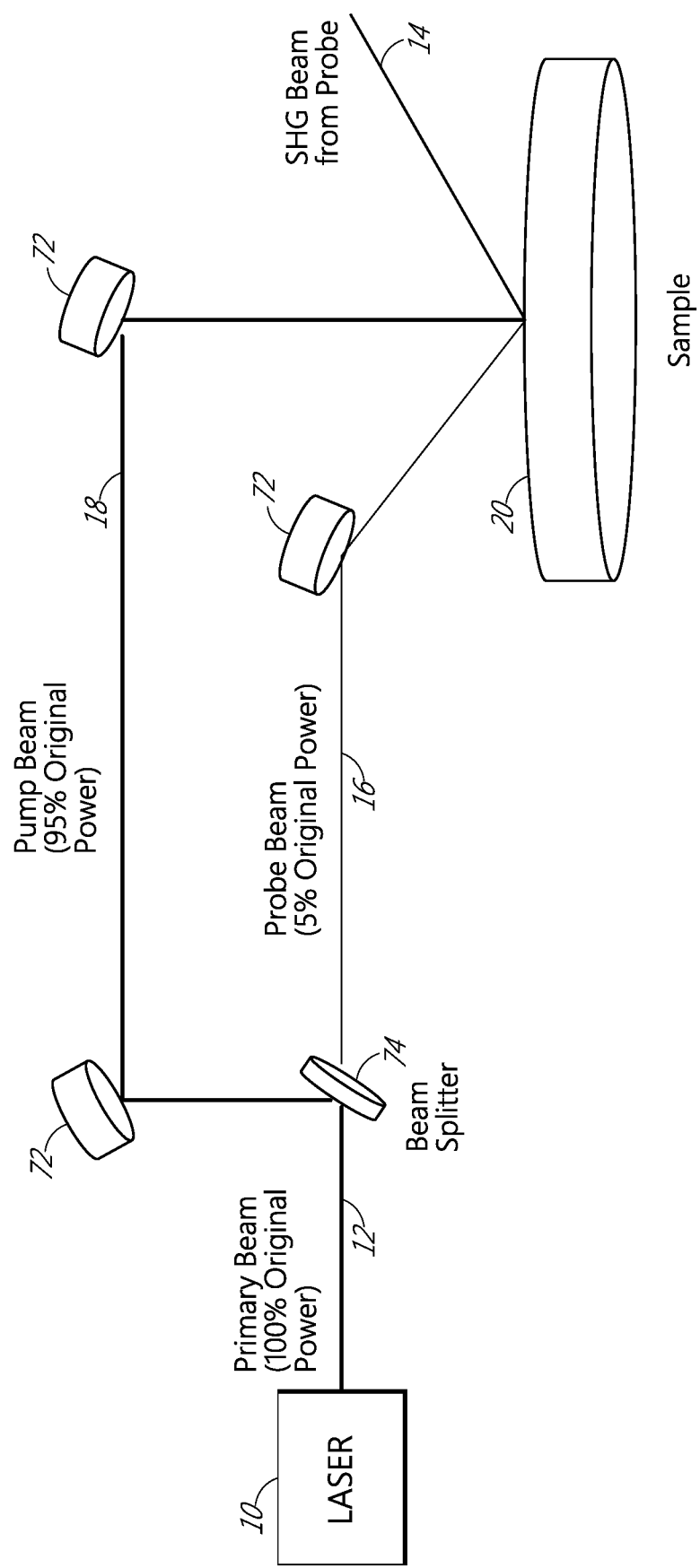
FIG. 1C is a diagram of another SHG metrology system embodiment hereof.

FIG. 1 is a diagram of a system 100 as may be employed in connection with the subject methodology. Other suitable system variations are presented in the portion of U.S. Provisional Application No. 61/980,860, filed on Apr. 17, 2014, titled "WAFER METROLOGY TECHNOLOGIES," referred to as Section II entitled, "CHARGE DECAY MEASUREMENT SYSTEMS AND METHODS" for example, as to intermediate optics, the inclusion of optical delay line(s) and optional electrode features.

As shown, system 100 includes a primary or probe laser 10 for directing an interrogation beam 12 of electro-magnetic radiation at a sample wafer 20, which is held by a vacuum chuck 30. As illustrated in FIG. 1B, the chuck 30 includes or is set on x- and y-stages and optionally also a rotational stage for positioning a sample site 22 across the wafer relative to where the laser(s) are aimed. The x-y stage enables scanning multiple wafer surface sites or locations 22 without movement of other hardware. A rotational stage optionally enables assessing crystal structure effects on SHG such as strain, and associated defects or areas of concern on materials being characterized. Further optional features, aspects and/or uses of chuck 30 are presented in portions of U.S. Provisional Application No. 61/980,860, filed on Apr. 17, 2014, titled "WAFER METROLOGY TECHNOLOGIES," referred to as Section IV entitled, "FIELD-BIASED SHG METROLOGY" and Section III titled "TEMPERATURE-CONTROLLED METROLOGY," both which are incorporated herein by reference in their entirety. The sample site 22 can include one or more layers. The sample site 22 can comprise a composite substrate including at least two layers. The sample site 22 can include an interface between two dissimilar materials (e.g., between two different semiconductor materials, between two differently doped semiconductor materials, between a semiconductor and an oxide, between a semiconductor and a dielectric material, between a semiconductor and a metal or an oxide and a metal).

When system 100 is in use, a beam 14 of reflected radiation directed at a detector 40 will include an SHG signal. The detector may be any of a photomultiplier tube, a CCD camera, a avalanche detector, a photodiode detector, a streak camera and a silicon detector. System 100 may also include one or more shutter-type devices 50. The type of shutter hardware used will depend on the timeframe over which the laser radiation is to be blocked, dumped or otherwise directed away from the sample site. An electro-optic blocking device such as a Pockel's Cell or Kerr Cell can be used to obtain very short blocking periods (i.e., with actuation times on the order of $10^{-9}$ to $10^{-12}$ seconds).

For longer blocking time intervals (e.g., from about $10^{-5}$ seconds and upwards) mechanical shutters or flywheel chopper type devices may be employed. However, electro-optic blocking devices will allow a wider range of materials to be tested in accordance with the methods below. A photon counting system 44 capable of discretely gating very small time intervals, typically, on the order of picoseconds to microseconds can be employed to resolve the time-dependent signal counts. For faster-yet time frames optical delay line(s) may be incorporated as noted above.

System 100 can include an additional electromagnetic radiation source 60 also referred to as a pump source. In various implementations, the radiation source 60 can be a laser illustrated as emitting a directed beam 62 or a UV flash lamp emitting a diverging or optically collimated pulse 64. In the case of a laser source, its beam 62 may be collinear with beam 12 (e.g., as directed by additional mirrors or prisms, etc.) Source 60 output wavelengths of light may be anywhere from about 80 nm and about 1000 nm. Using shorter wavelengths in this range (e.g. less than about 450 nm), is possible to drive charge excitation using fewer photons and/or with lower peak intensities than at longer wavelengths.

For a flash lamp, energy per flash or power level during flash may be substrate material dependent. A flashlamp producing a total energy of 1 J to 10 kJ per flash would be appropriate for fully depleted silicon-on-insulator (FD-SOI). However a pulsed or constant UV source would be viable as well. The important factor in the pump characteristics and use is that charge carriers are injected into the dielectric of the material to be interrogated. Manufacturers of suitable flash lamps include Hellma USA, Inc. and Hamamatsu Photonics K.K.

When a laser is employed as source 60, it may be any of a nanosecond, picosecond or femtosecond or faster pulse laser source. It may even be a continuous solid-state laser. In various embodiments, the pump source is tunable in wavelength. Commercially available options regarding lasers which are tunable include Spectra Physics' Velocity and Vortex Tunable Lasers. Additional tunable solid state solutions are available from LOTIS Ltd.'s LT-22xx series of solid state lasers.

Whether provided as a laser or a flash lamp, pump source 60 can be selected for relatively high average power. This could be from about 10 mW to about 10 W, but more typically from about 100 mW to about 4 W, depending on material to be interrogated (as, again, the consideration is ensuring that charge carrier mobility is induced in a way such that charge carriers are injected into the interface of the material (e.g., the dielectric interface), which can be material specific. The average power of the pump source 60 is selected to be below the optical damage threshold of the material. For example, pump source 60 can be selected to have an average optical power between 1-2 W when the interrogating material comprises silicon so as to not exceed the optical damage threshold for silicon.

Probe laser 10 may be any of a nanosecond, picosecond or femtosecond or faster pulse laser source. Two options that are currently commercially available lasers having the peak power, wavelength and reliability needed are doped fiber and Ti:Sapphire units. Coherent's VITESSE and Spectra Physics' MAI TAI lasers are examples of suitable Ti:Sapphire devices. Femtolasers Gmbh and others manufacture also manufacture other relevant Ti:Sapphire devices. Suitable doped fiber lasers are produced by IMRA, OneFive, and Toptica Photonics. Pico- and/or nano-second lasers from many manufacturers, such as Hamamatsu, may be options as well depending on the substrate material and pump type. Laser 10 may operate in a wavelength range between about 100 nm to about 2000 nm with a peak power between about 10 kW and 1 GW, but delivering power at an average below about 150 mW.

Various other optional so-called "intermediate" optical components may be employed in system 100. For example, the system may include a dichroic reflective or refractive filter 70 for selectively passing the SHG signal coaxial with reflected radiation directly from laser 10 and/or source 60. Alternatively, a prism may be employed to differentiate the weaker SHG signal from the many-orders-of-magnitude-stronger reflected primary beam. However, as the prism approach has proved to be very sensitive to misalignment, a dichroic system as referenced above may be preferred. Other options include the use of diffraction grating or a Pellicle beam splitter. An optical bundle 80 for focusing and collimating/columniation optics may be provided. Alternatively, a filter wheel 90, polarizer(s) 92 and/or zoom len(s) 94 units or assemblies may be employed in the system. Also, an angular (or arc-type) rotational adjustment (with corresponding adjustment for the detector) and in-line optical components may be desirable.

In the implementation illustrated in FIG. 1C, the beam 12 from the laser 10 can be split by a beam splitter 74 between two optical paths. The beam splitter 74 can split the beam 12 unequally between the two optical paths. For example, 70% of the energy of the beam 12 can be directed along a first optical path (e.g., as beam 16) and 30% of the energy of the beam 12 can be directed along a second optical path (e.g., as beam 18). As another example, 60% of the energy of the beam 12 can be directed along the first optical path and 40% of the energy of the beam 12 can be directed along the second optical path. As yet another example, 80% of the energy of the beam 12 can be directed along the first optical path and 20% of the energy of the beam 12 can be directed along the second optical path. The split may thus be unequal (e.g., 70-30%, 80-20%, 60-40% or any range therebetween, such as between 60-90% in one path and between 40-10% in another path as well as outside these ranges), sending a majority of the power in the pump beam, and a minority in the probe beam. For example, the split may be 60-70% and 40-30%, for the pump and probe, respectively, 70-80% versus 30-20% for the pump and probe, respectively, 80-90% versus 20-10%, for the pump and probe respectively, or 90-99.999% versus 10-0.001%, for the pump and probe respectively. In different embodiments, the probe beam could be between 0.001% to 49.99% while the pump beam could be between 50.001% and 99.999%, for example. The sum of the two beams may be 100% or approximate thereto. The split may be determined by the particular material system being characterized in some cases. In the example shown in FIG. 1C, 5% of the beam energy of the beam 12 is directed along the first optical path and 95% of the energy of the beam 12 is directed along the second optical path.

The beam splitter 74 can comprise a dielectric mirror, a splitter cube, a metal coated mirror, a pellicle mirror or a waveguide splitter. In implementations, where the beam 12 includes optical pulses, the beam splitter 74 can include an optical component having negligible dispersion that splits the beam 12 between two optical paths such that optical pulses are not broadened. As illustrated in FIG. 1C, each of the beams can be redirected or aimed using various mirror elements 2072.

The output from the detector 40 and/or the photon counting system 44 can be input to an electronic device 48. The electronic device 48 can be a computing device, a computer, a tablet, a microcontroller or a FPGA. The electronic device 48 includes a processor that may be configured to execute one or more software modules. In addition to executing an operating system, the processor may be configured to execute one or more software applications, including a web browser, a telephone application, an email program, or any other software application. The electronic device 48 can implement the methods discussed herein by executing instructions included in a machine-readable non-transitory storage medium, such as a RAM, ROM, EEPROM, etc. The electronic device 48 can include a display device and/or a graphic user interface to interact with a user. The electronic device 48 can communicate with one or more devices over a network interface. The network interface can include transmitters, receivers and/or transceivers that can communicate such as, for example, wired Ethernet, Bluetooth®, or wireless connections.

Regarding other options, since an SHG signal is weak compared to the reflected beam that produces it, it is desirable to improve the signal-to-noise ratio of SHG counts. As photon counting gate times for the photon counting system 44 decrease for the blocking and/or delay processes described herein, improvement becomes even more important. One method of reducing noise that may be employed is to actively cool the photon counter. This can be done using cryogenic fluids such as liquid nitrogen or helium or solid state cooling through use of a Peltier device. Others areas of improvement may include use of a Marx Bank Circuit (MBC) as relevant to shutter speed. Moreover, system 100 may be incorporated in-line within a production line environment. Production line elements preceding or following system 100 may include any of epitaxial growth system, lithography and/or deposition (CVD, PVD, sputtering, etc.) systems.

Figure 2B:
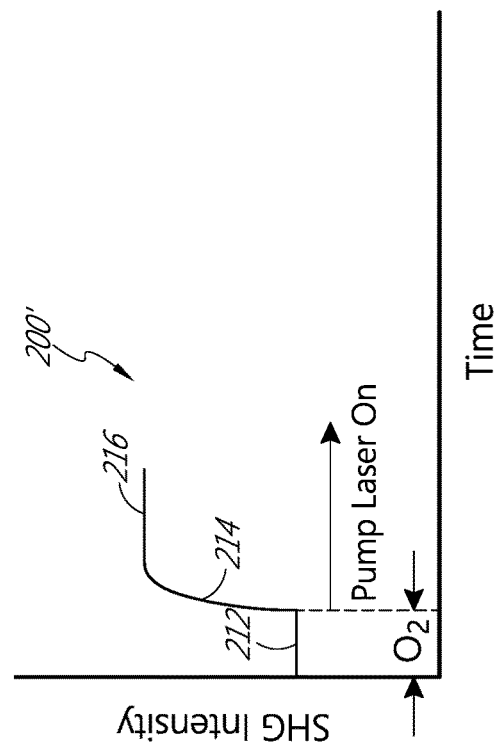
FIGS. 2A/2B and 3A/3B are diagrams illustrating example pump/probe system uses for producing characteristic SHG signals.
Figure 2A:
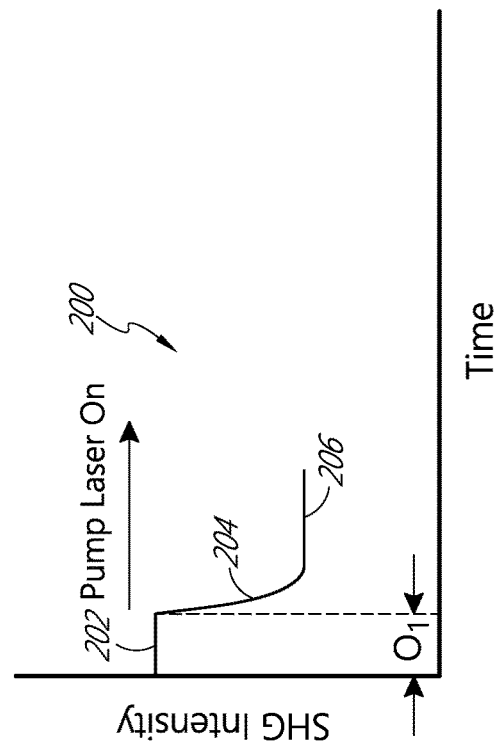

Turning now to FIGS. 2A/2B and 3A/3B, these are schematic diagrams illustrating example types of SHG curves that may be produced with the subject pump/probe system in their methods of use. In FIGS. 2A and 2B, the timescale to obtain such signals in on the order of milliseconds ($10^{-3}$ s). Thus, these are "fast" processes. As further discussed below, they may offer several orders of magnitude of time-wise improvement relative to existing approaches. For example, a flash lamp capable of exposing the entire surface of a test material to UV radiation prior to SHG probing drastically reduces the overall scan time since sustained measurements at each point may not be required.

Specifically, in FIG. 2A an SHG signal 200 is measured with an initial intensity 202. This signal is produced by the probe source radiation applied at a surface location. Upon adding pump source radiation (to that of the probe which stays on) after a given temporal offset ($O_1$), the signal intensity drops along a time-dependent curve 204 to a lower level 206. Conversely, in FIG. 2B SHG signal 200' at a lower level 212 produced by probe radiation alone increases along a time-dependent curve 214 to a higher plateau 216 upon applying pump radiation after a time offset ($O_2$). Signals 200 and 200' also include a time-independent component or portion at the beginning and end of the curves.

Both observations in FIGS. 2A and 2B may be made with the subject system depending on substrate material and different laser powers (e.g., in this case, that of the pump). In various embodiments charge separation comprise electrons and holes separating from each other after excitation from a photon. Electrons injected into the $SiO_2$ conduction band from the silicon valence band by the photons from the laser are trapped primarily on the top surface of the oxide. The holes congregate mostly in the silicon valence band close to the $Si/SiO_2$ interface. This separation of charge carriers due to excitation from the incident radiation or from internal photoemission contributes to the electric field(s) present inside the subject system, which in turn changes the SHG measured. Various factors, such as the presence of gaseous Oxygen at the testing site, as well as the composition and structure of the sample in question, will determine whether the observation is made as in FIG. 2A or 2B.

Indeed, a combination of signals 200 and 200' has been observed in some instances. In those instances, the signal intensity first dropped from a peak, bottomed out, and then rose to an asymptote again. Generally, the SHG intensity curves are determined by the non-linear susceptibility tensor, which is in turn affected by molecular orientation, atomic organization, electronic structure and external fields. Charge carriers moving across the interface will change the charge state in the structure and the electric field in the sub-interfacial layer where the SHG signal generation occurs. Depending on the type (positive or negative) of charge carriers crossing the interface, and the initial state of the field across the interface, different time-dependent curves will be observed. The intensity of the detected SHG signal can depend on various factors including spot size, average laser power, and peak laser power. In various implementations, the system 100 can be configured to detect SHG signal having an intensity in a range between about 400 counts/second and about 7 million counts/second. The pump/probe system described herein can reduce the time required for the charge carriers moving across the interface to reach a saturation level. In various embodiments, the time required for the charge carriers moving across the interface to reach a saturation level can between 1 millisecond and 1000 seconds in the pump/probe system described herein. Since it may be advantageous to obtain the time evolution of the SHG signal when the charge carrier density in the region including interface is below saturation as well as when the charge carrier density in the region including interface reaches saturation level, the system can be configured to obtain SHG signal measurements within about 1 microsecond after turning on/turning off the pump radiation. For example, the system can be configured to obtain SHG signal measurements within 10 seconds after turning on/turning off the pump radiation (or probe radiation), within about 6 seconds after turning on/turning off the pump radiation (or probe radiation), within about 1 second after turning on/turning off the pump radiation (or probe radiation), within about 100 milliseconds after turning on/turning off the pump radiation (or probe radiation) or within about 1 millisecond after turning on/turning off the pump radiation (or probe radiation), within 1 microsecond after turning on/turning off the pump radiation (or probe radiation), within 1 nanosecond after turning on/turning off the pump radiation (or probe radiation) or in any range formed by any of these values (for example, for time periods greater than a nanosecond, greater than a microsecond, greater than a millisecond, etc.) as well as outside any of those ranges. These values and ranges apply for obtaining data obtained from a single point, but with proper imaging optics, could be increased to substantial areas of the wafer, up to and including the entire wafer at once. As indicated by the parentheticals above, these values and ranges also apply to the probe radiation. Reducing the charging time and the time required to obtain the SHG signal can allow for faster testing of interfaces and thus increase through-put of testing and/or manufacturing production lines.

Figure 3B:
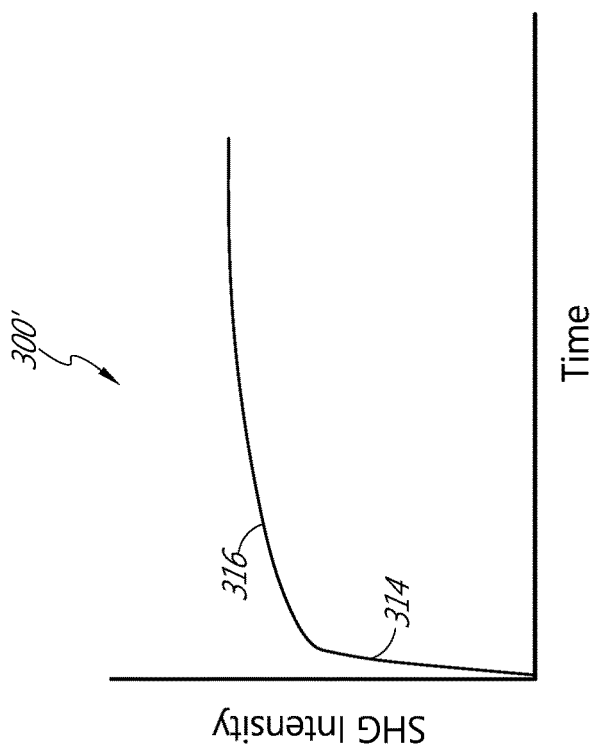
Figure 3A:
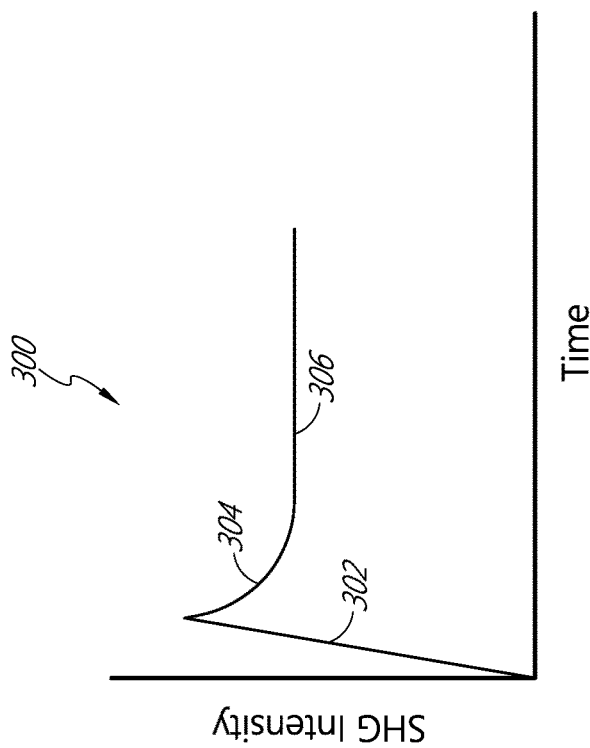

By way of comparison, FIGS. 3A and 3B schematically illustrate SHG signal curves 300 and 300' for corresponding materials in which only one radiation source is used (in this case a high average power and high peak power laser) to interrogate the substrate as in existing SHG techniques. The time scale for generating signals 300 and 300 in FIGS. 3A and 3B is on the order of tens- to hundreds ($10^2$ s) seconds.

Over such time, these signals (like the signals in FIGS. 2A and 2B) include lower and upper plateaus 306, 316 that can be characterized after initial 302 and/or time-dependent signals. Thus, while similar (or identical) analysis may be performed with the signals 200/200' and 300/300', the main difference is that with the subject systems (i.e., using a lower peak power femto-second probe laser in conjunction with a higher average power pump for material pre-excitation) allows for vastly improved time-wise efficiency in obtaining the requisite signal information. Moreover, the subject approach provides a way to more easily determining time-independent SHG measurements without the use of a filter-wheel or some other method.

Figure 4:
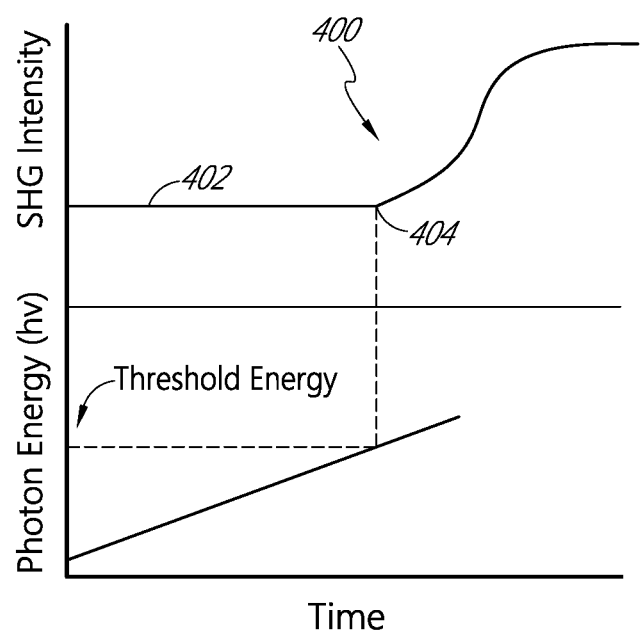
FIG. 4 is a diagram illustrating probe/pump system use to determine threshold injection carrier energy.

In any case, FIG. 4 illustrates a method for determining threshold injection carrier energy. In this case, the pump comprises a tunable wavelength laser. This allows ramp-up of the output frequency (and hence energy by E=hv) of the photons over time from the pump incident on the sample. The observed SHG activity action is illustrated as signal 400. With the pump laser so-applied or engaged, an initial SHG signal level 402 generated by application of a probe laser is observed to the point the signal suddenly changes (i.e., producing an inflection, discontinuity, maximum, minimum, step function, cusp, or sudden change in slope of sorts at 404). The frequency at this point is taken to correspond to the threshold energy. In various implementations, the threshold energy is the energy required to transport electrons from the valence band of one semiconductor material to the conduction band of another semiconductor material across an interface between two materials such as two semiconductor materials or a semiconductor material and a dielectric material (e.g., Si and $SiO_2$, Si and $Si_3N_4$, Si and $Ta_2O_5$, Si and $BaTiO_3$, Si and $BaZrO_3$, Si and $ZrO_2$, Si and $HfO_2$, Si and $La_2O_3$, Si an $Al_2O_3$, Si and $Y_2O_3$, Si and $ZrSiO_4$). The system 100 can be configured to measure threshold energy in the range between about 1.0 eV and about 6.0 eV. The systems and methods described herein can be configured to determine threshold energy for a variety of interfaces such as for example, between two different semiconductors, between a semiconductor and a metal, between a semiconductor and a dielectric, etc.

Figure 5:
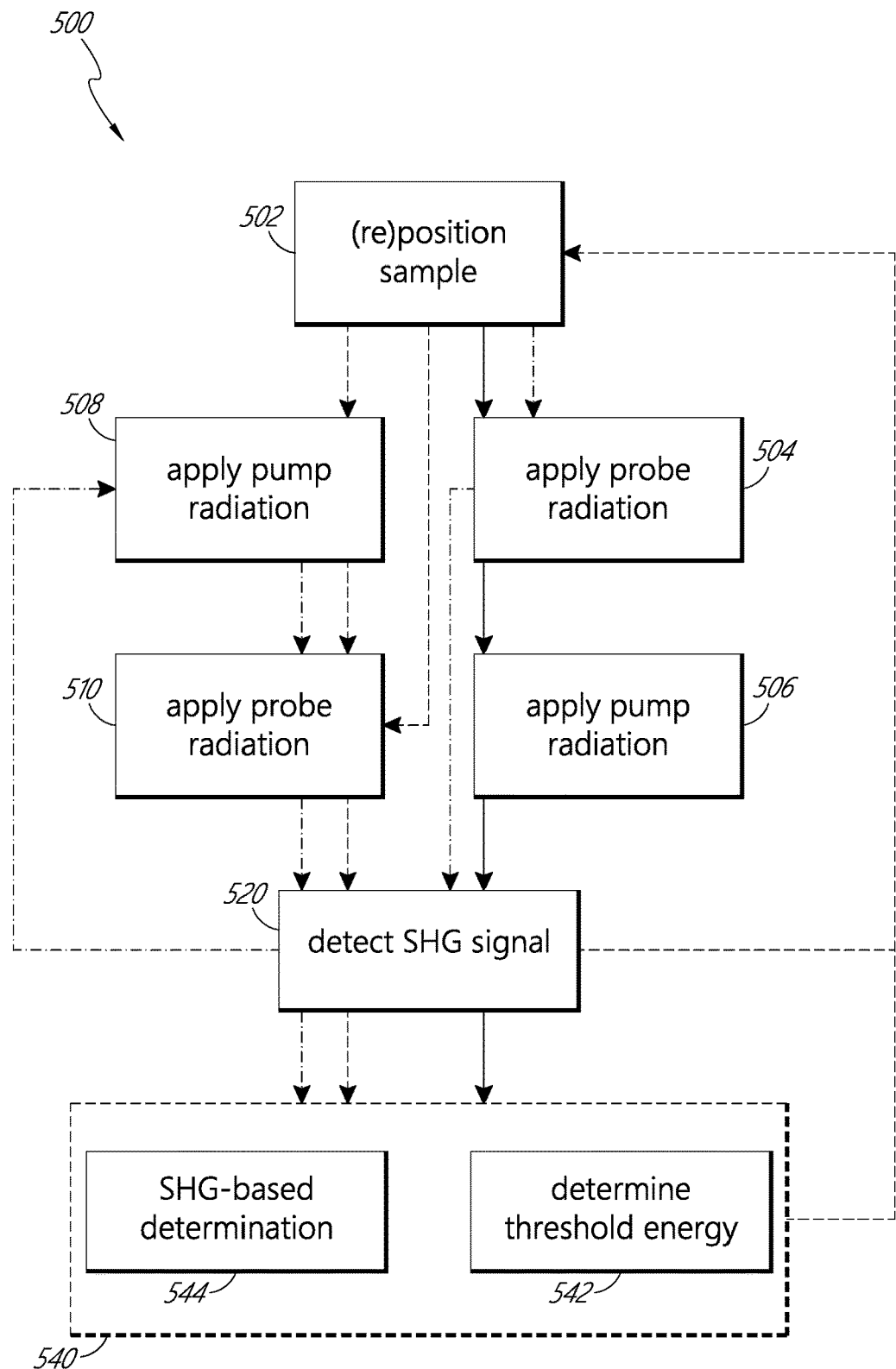
FIG. 5 is a flowchart detailing methods to produce signals as presented in the diagrams.

FIG. 5 is a flowchart 500 illustrating an implementation of a method for characterizing semiconductor devices with SHG. Various process flowpaths are indicated. Any such methods may begin at 502 with positioning a sample at a desired location (e.g., typically by locating chuck 30 after a wafer 20 has been secured thereto). Progressive positioning (i.e., re-positioning) may occur after any given SHG detection event 520 as further described for scanning multiple surface positions or even every surface position in a region of the sample or even every surface position of the sample. Alternatively, such action may occur after a given determination at 540 is made concerning a detected SHG signal (either "return" option indicated by dotted line). Further details regarding alternative determinations may be appreciated in reference to the other portions of this application referenced above. In any case, following sample positioning or re-positioning, a given flowpath is selected (or another flowpath may be run at the same surface position after in sequence to generate different data).

Following a one process flowpath (solid lines, in part), at 504 probe source radiation is applied to the sample surface at a given location. Next, at 506 pump source radiation is applied. In this example, the pump radiation is applied in a varying manner that (optionally) increases photon energy linearly by decreasing the radiation wavelength. The resulting SHG is detected at 520. At 542 signal analysis (per the example in FIG. 4) allows for carrier injection threshold energy to be determined. In various implementations, the energy of the pump radiation can correspond to the threshold energy of the semiconductor interface. Accordingly, the energy of the pump radiation can be between about 1.0 eV and about 6.0 eV. For example, to determine the threshold energy across a Si and $SiO_2$ interface, the threshold energy of the pump radiation can vary between about 4.1 eV and about 5.7 eV. Variation in the energy of the pump radiation can be accomplished by varying the frequency (or wavelength) of the radiation. For example, to interrogate a sample with an expected value of the threshold energy around 3.2 eV, the wavelength of the pump radiation can be varied between about 443 nm and about 365 nm. In various implementations, the energy of the pump radiation can be below the threshold energy of the semiconductor interface since the photons from the pump radiation can generate electrons with twice energy (e.g., when a single electron absorbs two photons). In such implementations, the charging time is increased which may provide observation with increases resolution and intensity. Increasing the charging time can also increase the time required to test a sample site which can reduce throughput.

Following another flowpath (dashed lines, in part), at 508 pump radiation is applied to the substrate. Such application may be directed only at the surface (e.g., by a laser) to be immediately interrogated or the entire surface of the wafer (e.g., using a flash lamp). Next, at 510 the section of the sample to be interrogated is exposed to probe source radiation. The resulting SHG is detected at 520. The pump-probe-detect aspects of the method may then repeat potentially after sample repositioning at 502. As indicated, however, action box 508 may be skipped and pumping again may be avoided or omitted from a sequential scanning process, as in the example above where the whole substrate was initially exposed to pump radiation. In any case, at 544 any of a variety of SHG-based signal analysis may be conducted to make a determination other than for threshold energy as in block 542 as discussed elsewhere in this patent application.

Following another process flow path (dash-and-dot/centerline lines, in part) probe interrogation is performed at 504 and 510 before and after pump radiation is applied at 508 with SHG signal data collection at 520 directly after probe radiation application at 504 and 510. Again, this method may be done recursively to sample a plurality of sites such as every section of a substrate or a region thereof, returning to flowchart element 502 for repositioning and the probe-detect-pump-probe-detect method or sub-method repeated.

Notably, any of the SHG signal analysis methods or sub-methods (generically embraced in box 540 and 542) can be performed in real-time, as in instantaneous or near-instantaneous output. In doing so, any of the spectrographic properties determined by the data gathered can be computed by a software package either by integrated software on the machine or remotely. Alternatively, SHG signal analysis may be handled in post-processing after some or all of the SHG data has been detected or collected.

The systems and methods described herein can be used to characterize a sample (e.g., a semiconductor wafer or a portion thereof). For example, the systems and methods described herein can be used to detect defects or contaminants in the sample as discussed above. The systems and methods described herein can be configured to characterize the sample during fabrication or production of the semiconductor wafer. Thus, the systems and methods can be used along a semiconductor fabrication line in a semiconductor fabrication facility. The systems and methods described herein can be integrated with the semiconductor fabrication/production line. The systems and methods described herein can be integrated into a semiconductor fab line with automated wafer handling capabilities. For example, the system can be equipped with an attached Equipment Front End Module (EFEM), which accepts wafer cassettes such as a Front Opening Unified Pod (FOUP). Each of these cassettes can be delivered to the machine by human operators or by automated cassette-handling robots which move cassettes from process to process along fabrication/production line.

In various embodiments, the system can be configured such that once the cassettes are mounted on the EFEM, the FOUP is opened, and a robotic arm selects individual wafers from the FOUP and moves them through an automatically actuated door included in the system, into a light-tight process box, and onto a bias-capable vacuum chuck. The chuck may be designed to fit complementary with the robotic arm so that it may lay the sample on top. At some point in this process, the wafer can be held over a scanner for identification of its unique laser mark.

Accordingly, a system configured to be integrated in a semiconductor fabrication/assembly line can have automated wafer handling capability from the FOUP or other type of cassette; integration with an EFEM as discussed above, a chuck designed in a way to be compatible with robotic handling, automated light-tight doors which open and close to allow movement of the robotic wand/arm and software signaling to EFEM for wafer loading/unloading and wafer identification.

Part II

Figure 6C:
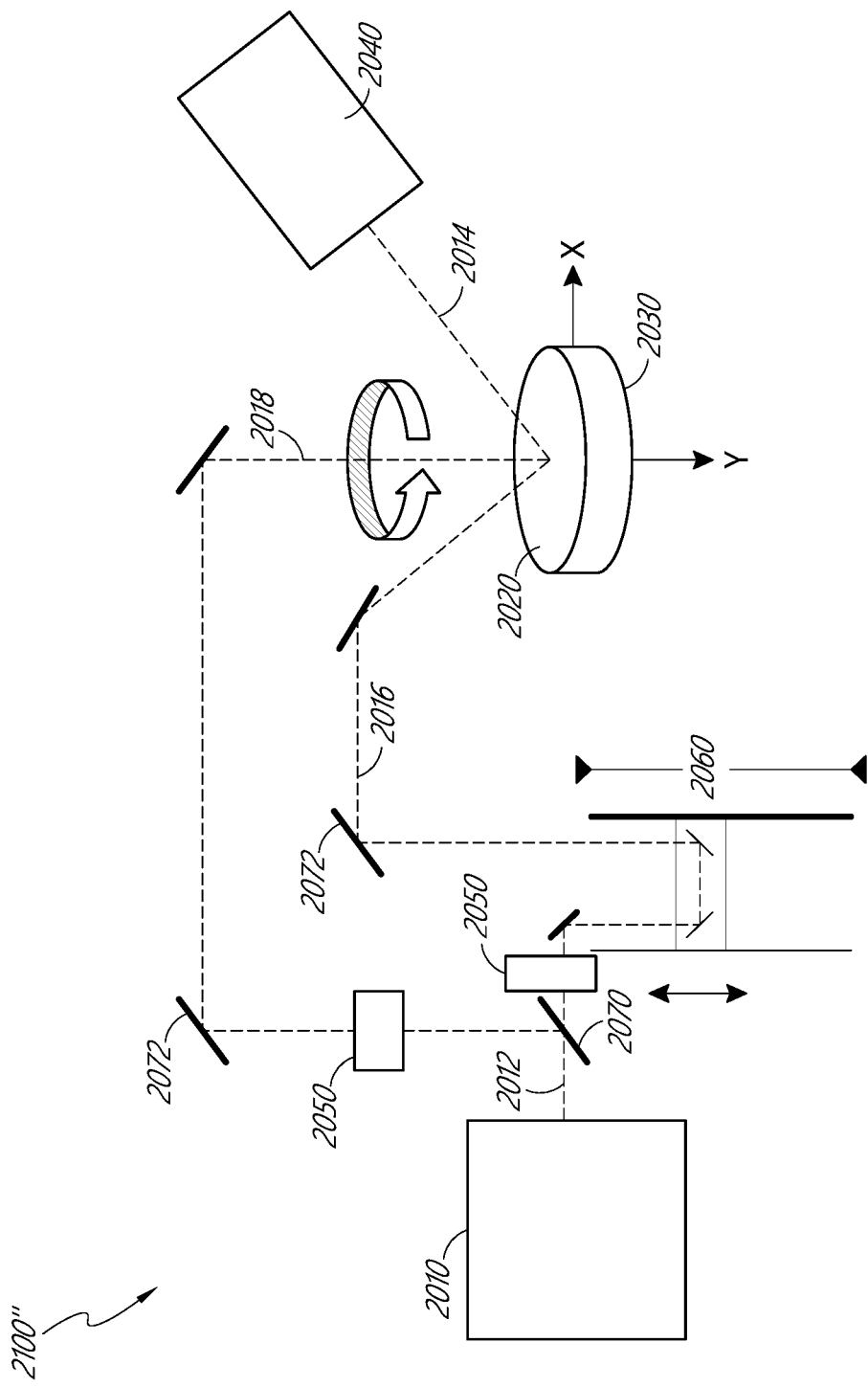

FIG. 6A is a diagram of a first system 2100 as may be employed in connection with the subject methodology. Alternative systems 2100' and 2100" are shown in FIGS. 6B and 6C. Each system includes a primary laser 2010 for directing a primary beam 2012 of electro-magnetic radiation at a sample wafer 2020, which sample is held by a vacuum chuck 2030. The chuck 2030 includes or is set on x- and y-stages and optionally also a rotational stage for positioning a sample site 2022 across the wafer relative to where the laser(s) are aimed. A beam 2014 of reflected radiation directed at a detector 2040 will include an SHG signal. The detector may be any of a photomultiplier tube, a CCD camera, a avalanche detector, a photodiode detector, a streak camera and a silicon detector. The sample site 2022 can include one or more layers. The sample site 2022 can comprise a composite substrate including at least two layers. The sample site 2022 can include an interface between two dissimilar materials (e.g., between two different semiconductor materials, between two differently doped semiconductor materials, between a semiconductor and an oxide, between a semiconductor and a dielectric material, between a semiconductor and a metal, between an oxide and a metal, between a metal and a metal or between a metal and a dielectric).

Also common to each of the embodiments is the inclusion of one or more shutter-type devices 2050. These are employed as described in connection with the methodology below. The type of shutter hardware used will depend on the timeframe over which the laser radiation is to be blocked, dumped or otherwise directed away from the sample site.

An electro-optic blocking device such as a Pockel's Cell or Kerr Cell is used to obtain very short blocking periods (i.e., with switching times on the order of $10^{-9}$ to $10^{-12}$ seconds). For longer blocking time intervals (e.g., from about $10^{-5}$ seconds and upwards) mechanical shutters or flywheel chopper type devices may be employed.

However, electro-optic blocking devices will allow a wider range of materials to be tested in accordance with the methods below. A photon counting system 2044 capable of discretely gating very small time intervals, typically, on the order of picoseconds to microseconds can be included to resolve the time-dependent signal counts.

Hardware is contemplated for pushing the methods into faster-yet time frames. Namely, as shown in FIG. 6C, the system(s) may include delay line hardware 2060. Beam splitting and switching (or shuttering on/off) between a plurality of set-time delay lines for a corresponding number of time-delayed interrogation events is possible. However, a variable delay line may be preferred as offering a single solution for multiple transient charge decay interrogation events on a time frame ranging from immediately (although delay of only $10^{-12}$ seconds may be required for many methodologies) to tens of nanoseconds after pump pulse. The desired delay time may even go into the microsecond regime if using a slower, kilohertz repetition laser. And while such hardware is uniquely suited for carrying out the subject methodology (both of which methodology and such hardware is believed heretofore unknown), it might be put to other uses as well.

In the implementation illustrated in FIG. 6C, the beam 2012 from the laser 2010 can be split by a beam splitter 2070 between two optical paths. The beam splitter 2070 can split the beam 2012 unequally between the two optical paths. For example, 70% of the energy of the beam 2012 can be directed along a first optical path (e.g., as beam 2016) and 30% of the energy of the beam 12 can be directed along a second optical path (e.g., as beam 2018). As another example, 60% of the energy of the beam 2012 can be directed along the first optical path and 40% of the energy of the beam 2012 can be directed along the second optical path. As yet another example, 80% of the energy of the beam 2012 can be directed along the first optical path and 20% of the energy of the beam 2012 can be directed along the second optical path. The beam splitter 2070 can comprise a dielectric mirror, a splitter cube, a metal coated mirror, a pellicle mirror or a waveguide splitter. In implementations, where the beam 2012 includes optical pulses, the beam splitter 2070 can include an optical component having negligible dispersion that splits the beam 2012 between two optical paths such that optical pulses are not broadened. As indicated by the double-arrow in FIG. 6C, the path of an "interrogation" beam 2016 taken off a beam splitter 2070 from primary beam 2012 can be lengthened or shortened to change its arrival timing relative to a "pump" beam 2018 wherein each of the beams are shown directed or aimed by various mirror elements 2072. Another approach (mentioned above) employs fiber optics in the optical delay component and/or other optical pathways (e.g., as presented in U.S. Pat. No. 6,819,844 incorporated herein by reference in its entirety for such description).

The output from the detector 2040 and/or the photon counting system 2044 can be input to an electronic device 2048 (see, e.g., FIGS. 6A and 6B). The electronic device 2048 can be a computing device, a computer, a tablet, a microcontroller or a FPGA. The electronic device 2048 includes a processor or processing electronics that may be configured to execute one or more software modules. In addition to executing an operating system, the processor may be configured to execute one or more software applications, including a web browser, a telephone application, an email program, or any other software application. The electronic device 2048 can implement the methods discussed herein by executing instructions included in a machine-readable non-transitory storage medium, such as a RAM, ROM, EEPROM, etc. The electronic device 2048 can include a display device and/or a graphic user interface to interact with a user. The electronic device 2048 can communicate with one or more devices over a network interface. The network interface can include transmitters, receivers and/or transceivers that can communicate over wired or wireless connections.

Figure 10:
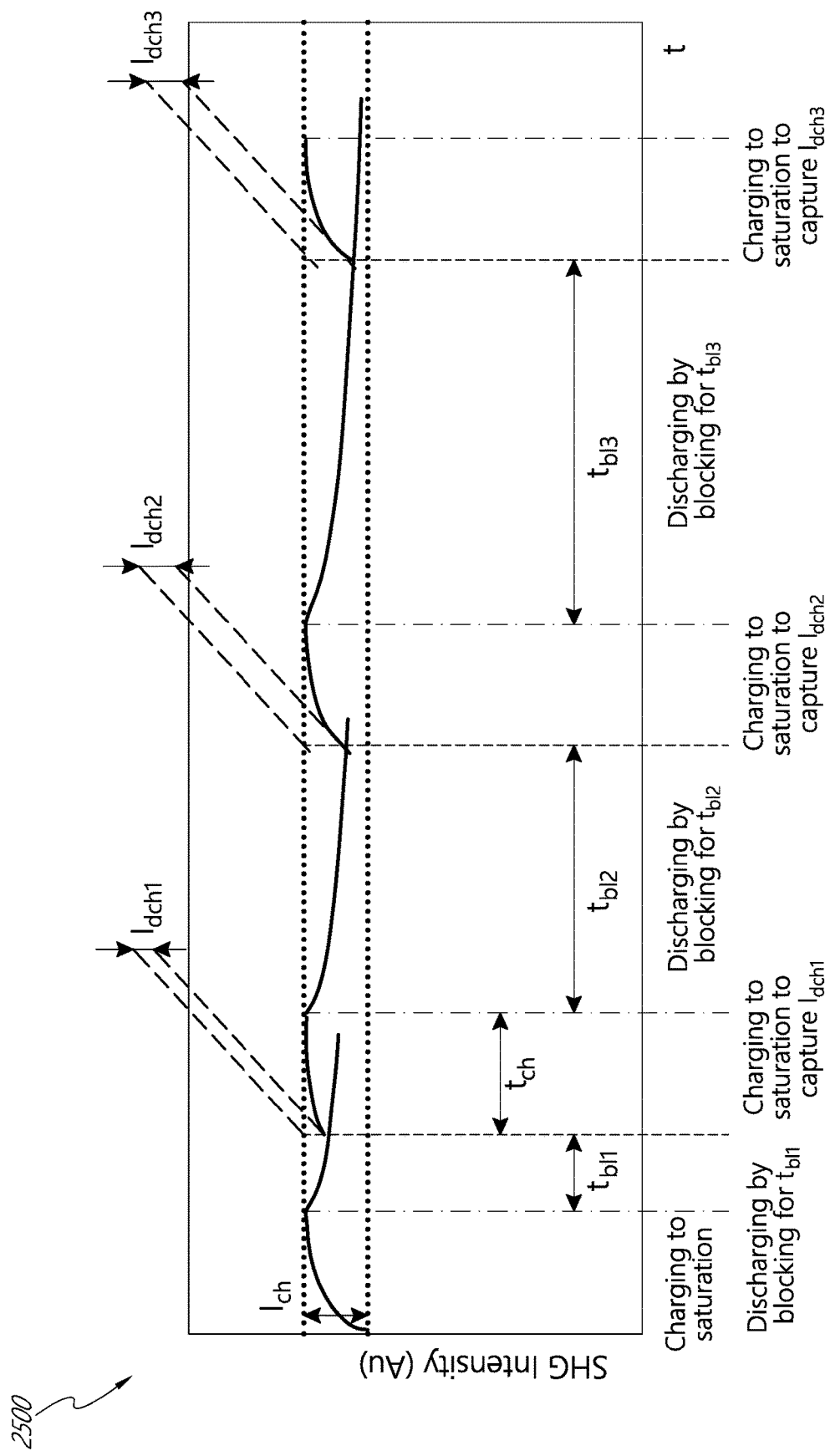
FIGS. 10 and 11 plot SHG interrogation-related method embodiments.
Figure 11:
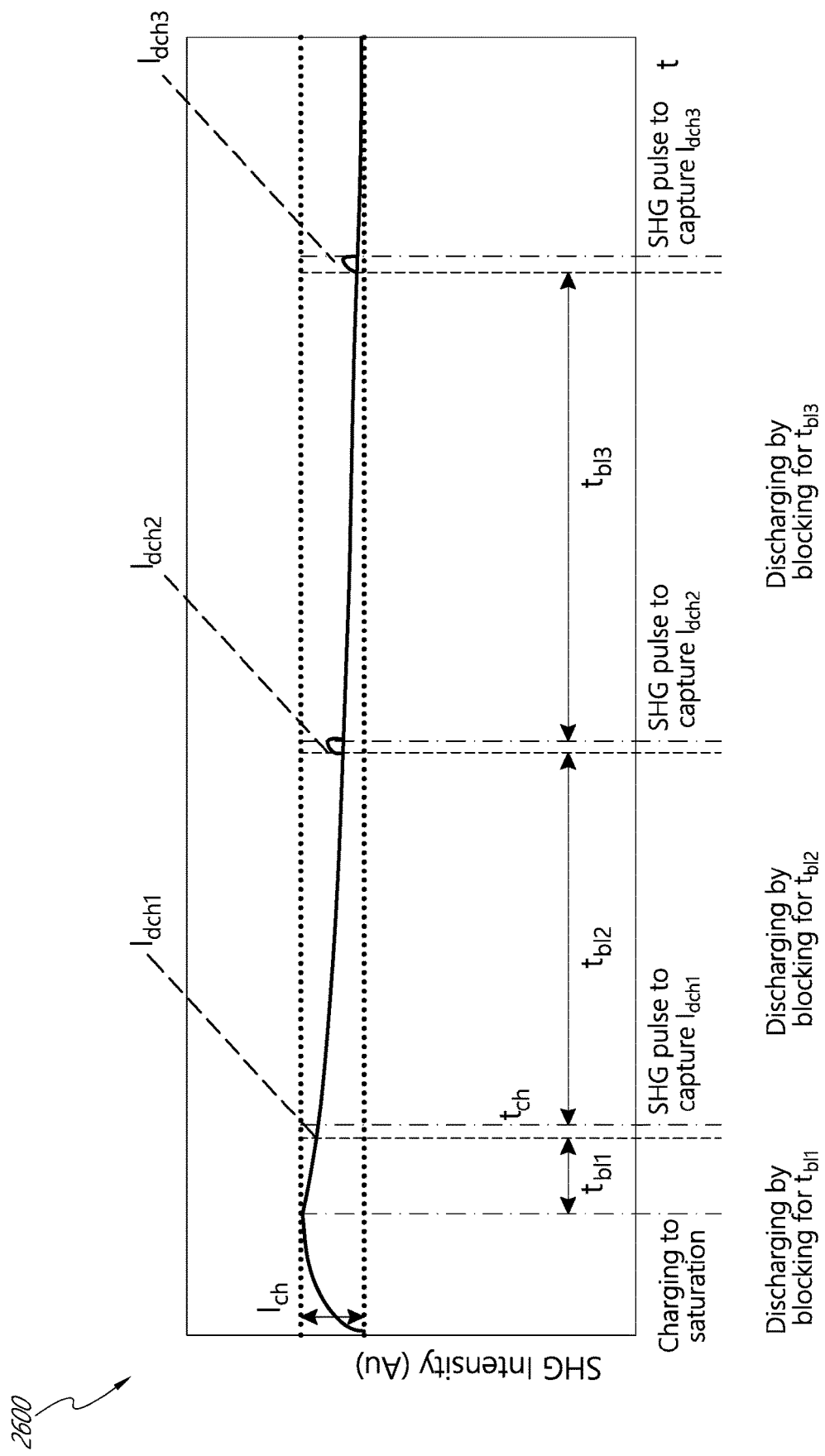

Another potential aspect of system 2100" concerns the manner in which the initial beam splitter works. Namely, the split may be unequal (e.g., 70-30%, 80-20%, 60-40% or any range therebetween, such as between 60-90% in one path and between 40-10% in another path as well as outside these ranges), sending a majority of the power in the pump beam, and a minority in the probe beam. For example, the split may be 60-70% and 40-30%, for the pump and probe, respectively, 70-80% versus 30-20% for the pump and probe, respectively, 80-90% versus 20-10%, for the pump and probe respectively, or 90-99.999% versus 10-0.001%, for the pump and probe respectively. In different embodiments, the probe beam could be between 0.001% to 49.99% while the pump beam could be between 50.001% and 99.999%, for example. The sum of the two beams may be 100% or approximate thereto. The split may be determined by the particular material system being characterized in some cases. The value (at least in part) of doing so may be to help facilitate methods such as shown in FIGS. 10 and 11 in which the power involved in SHG interrogation subsequent to material charging is desirably reduced or minimized as discussed below. Still another aspect is that the pump and probe beams are brought in at different angles. Such an approach facilitates measuring pump and probe SHG responses separately. In such cases, two detectors may be advantageously employed with one for each reflected beam path.

Various other optional optics distinguish the embodiments shown. For example, embodiments 2100 and 2100' are shown including a dichroic reflective or refractive filter 2080 for selectively passing the SHG signal coaxial with reflected radiation directly from the laser 2010. Alternatively, a prism may be employed to differentiate the weaker SHG signal from the many-orders-of-magnitude-stronger reflected primary beam. However, as the prism approach has proved to be very sensitive to misalignment, a dichroic system as referenced above may be preferred. Other options include the use of diffraction grating or a Pellicle beam splitter. As shown in system 2100, an optical bundle 2082 of focusing and collimating/collimation optics may be provided. As shown in system 2100', a filter wheel 2084, zoom lens 2086 and/or polarizers 2088 may be employed in the system(s). Also, an angular (or arc-type) rotational adjustment (with corresponding adjustment for the detector 2040 and in-line optical components) as shown in system 2100' may be desirable. An additional radiation source 2090 (be it a laser illustrated emitting a directed beam 2092 or a UV flash lamp emitting a diverging or optically collimated or a focused pulse 2094) may also be incorporated in the system(s) to provide such features as referenced above in connection with the portion of U.S. Provisional Application No. 61/980,860, filed on Apr. 17, 2014, titled "WAFER METROLOGY TECHNOLOGIES," referred to as Section I entitled "PUMP AND PROBE TYPE SHG METROLOGY," and/or initial charging/saturation in the methods below.

In these systems, laser 10 may operate in a wavelength range between about 700 nm to about 2000 nm with a peak power between about 10 kW and 1 GW, but delivering power at an average below about 100 mW. In various embodiments, average powers between 10 mW and 10 W should be sufficient. Additional light source 2090 (be it a another laser or a flash lamp) may operate in a wavelength range between about 80 nm and about 800 nm delivering an average power between about 10 mW and 10 W. Values outside these ranges, however, are possible.

Regarding other system options, since an SHG signal is weak compared to the reflected beam that produces it, it may be desirable to improve the signal-to-noise ratio of SHG counts. As photon counting gate times decrease for the blocking and/or delay processes described herein, improvement becomes even more useful. One method of reducing noise that may be employed is to actively cool the detector. The cooling can decreases the number of false-positive photon detections that are generated randomly because of thermal noise. This can be done using cryogenic fluids such as liquid nitrogen or helium or solid state cooling through use of a Peltier device. Others areas of improvement may include use of a Marx Bank Circuit (MBC) as relevant to shutter speed.

These improvements may be applied to any of the systems in FIGS. 6A-6C. Likewise, any or all of the above features described above in connection with systems 2100 and 2100' may be incorporated in system 2100". Indeed a, mix-and-match of features or components is contemplated between all of the systems.

Figure 7:
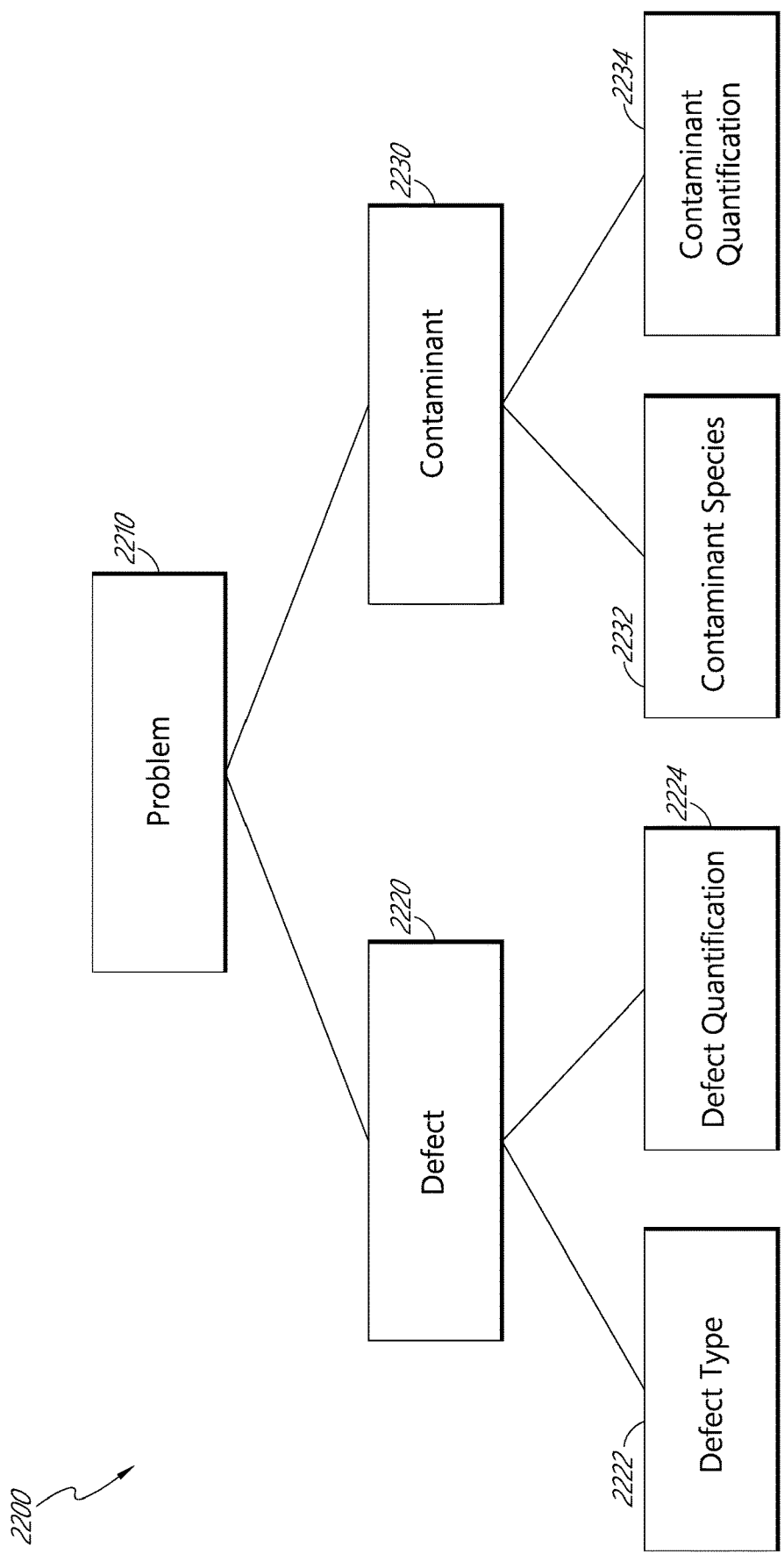
FIG. 7 is a chart of system function.

With such systems running the subject methodology, various determinations can be made not heretofore possible using laser-blocking and/or delay related techniques. FIG. 7 illustrates a process map or decision tree 2200 representing such possibilities. Namely, a so-called problem 2210 that is detected can be parsed between a defect 2210 (extended defects such as bond voids or dislocations, Crystal Originated Particle (COP) or the like) and a contaminant 2220 (such as copper inclusion or other metals in point defect or clustered forms). In terms of a defect, the defect type 2222 and/or a defect quantification 2224 determination (e.g., in terms of density or degree) can also be made. In terms of a contaminant, the contaminant species or type 2232 and/or a contaminant quantification 2234 determination can be made. Such parsing between defect and contaminant and identification of species may be performed in connection with determining charge carrier lifetimes, trap energies, trap capture cross-section and/or trap densities then comparing these to values in look-up tables or databases. Essentially these tables or databases include listings of properties of the material as characterized by the subject methods, and then matching-up the stated properties with entries in a table or database that correspond to particular defects or contaminants.

Trap capture cross-section and trap density may be observed in connection with, optionally, detected charging kinetics. As for determining charge carrier lifetimes and trap energies, the following equation based on work by I. Lundstrom, provides guidance:

$$\tau = \tau_0 \exp\left\{\frac{4}{3\hbar}\sqrt{2em^*_{ox}}\left[\phi_T^{3/2} - (\phi_T - E_{ox}d_T)^{3/2}\right] / E_{ox}\right\}$$

where τ is the tunneling time constant for the tunneling mechanism of the trap discharge, $\phi_r$ denotes the trap energy, $E_{ox}$ denotes the strength of the electric filed at the interface and the remaining equation variables and context are described at I. Lundstrom, JAP, v. 43, n. 12, p. 5045, 1972 which subject matter is incorporated by reference in its entirety. Further modeling and calculation options may be appreciated in reference to the portion of U.S. Provisional Application No. 61/980,860, filed on Apr. 17, 2014, titled "WAFER METROLOGY TECHNOLOGIES," referred to as Section III, titled "TEMPERATURE-CONTROLLED METROLOGY," which is incorporated herein by reference in its entirety.

In any case, the decay curve data obtained by the subject sample interrogation can be used to determine the parameters of trap energy and charge carrier lifetime by use of physical models and related mathematics. Representative sets of curves 2300, 2300' such as those pictured in FIGS. 8A and 8B may be calculated (where FIG. 8B highlights or expands a section of the data from FIG. 8A) from the equation above.

These curves demonstrate the relationship between time constant (vertical axis) and dielectric thicknesses (horizontal axis) for different trap or barrier energies. The vertical axis includes the ultrafast time scales of down to nanoseconds (1E-9s)). The horizontal axes are tunneling distances (or dielectric thickness, both terms being generally equivalent in this example). The different curves are lines of constant barrier energy. For example, in FIG. 8B, an electron caught in a trap with an energy depth of the listed barrier energy of 0.7 eV would exhibit a detrapping time constant of about 1E-5 seconds if the dielectric thickness was 40 Angstroms.

Further modeling with Poisson/Transport solvers can be used to determine trap density in MOS-like structures and more exotic devices using charge carrier lifetimes and known trap energies. Specifically, the photo-injected current due to femto-second optical pulses induces bursts of charge carriers which reach the dielectric conduction band. The average value of this current can be related to carrier concentration and their lifetimes in the regions. The E-field across the interface is the proxy by which SHG measures these phenomena.

Figure 8A:
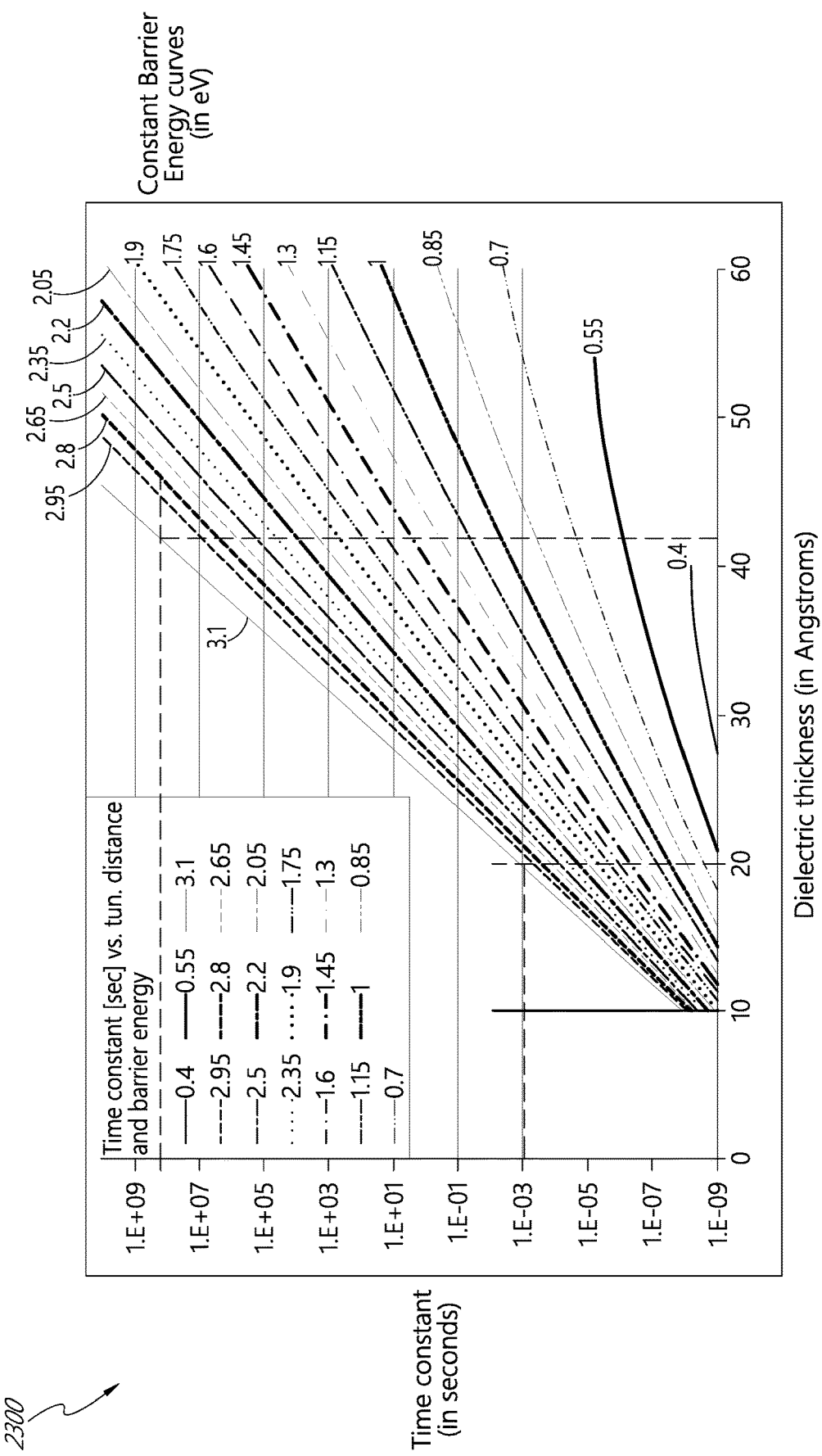
FIGS. 8A and 8B are charts representative of the manner of delivering such function.
Figure 8B:
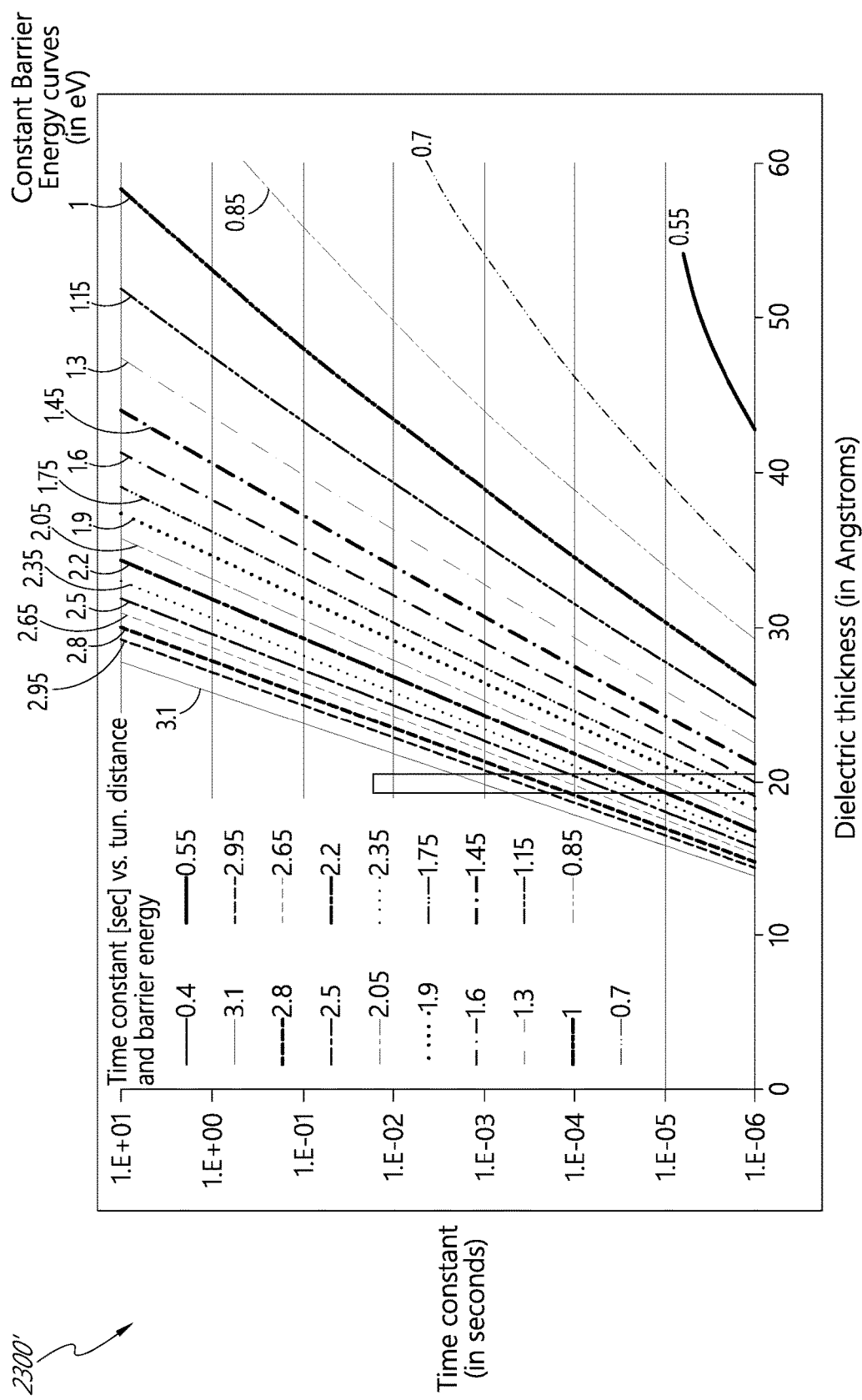

In the plot of FIG. 8A, it can be observed (see dashed lines) that 20 Angstrom of oxide has 1 msec discharge time constant for a trap having an energy of about 3 eV To relate the plots to an example of use in the subject system, suppose a 20 Angstrom oxide is interrogated after blocking laser excitation. As shown in FIG. 8B (see highlighted box) the result will be observable current from 1 μsec to about 1 msec and then all the current dies out.

The decay curves discussed in this application can be a product of multiple processes (e.g., charge relaxation, charge recombination, etc.) from traps having different energies and different relaxation/recombination time constants. Nevertheless, in various embodiments, the decay curves can be generally expressed by an exponential function $f(t)=A\exp(-\lambda t)+B$, where A is the decay amplitude, B denotes the baseline offset constant and λ denotes a decay constant. This general exponential function can be used to approximately characterize the "extent of decay" from experimentally obtained decay data curve. In various embodiments, it is possible to use the half-life $t_{1/2}$, average lifetime τ, and decay constant k, to characterize the extent of decay for a decay curve (obtained experimentally or by simulation). For example, the parameters A, B, and λ can be obtained from the decay data points that are obtained experimentally as discussed below. An average lifetime τ can then be calculated from the parameters A, B, and λ using theory of radioactive decay as a way of setting benchmarks for what is qualitatively called partial, or full-decay. For example, in some embodiments, τ can be given by the equation $(t_{1/2})/(\ln(2))$.

In various implementations, the charge state can be considered to have fully decayed after a time span of three average lifetimes τ, which corresponds to ~95% decay from full saturation. Partial decay can be expressed in terms of signal after a certain number of average lifetimes τ have elapsed.

In operations, the systems determine parameters (e.g., carrier lifetimes, trap energies, trapping cross-section, charge carrier density, trap charge density, carrier injection threshold energy, charge carrier lifetime, charge accumulation time, etc.) based at least in part on the subject methodology on a point-by-point basis on a portion (e.g., die size portion) of the wafer or an entire wafer. An entire wafer (depending on the material, surface area, and density of scan desired) can often be scanned in less than about 10 minutes, with these parameters determined for each point scanned. In various embodiments, a location of the wafer can be scanned in a time interval between about 100 milliseconds and about 3 seconds. For example, a location of the wafer can be scanned in about 950 milliseconds.

Figure 9:
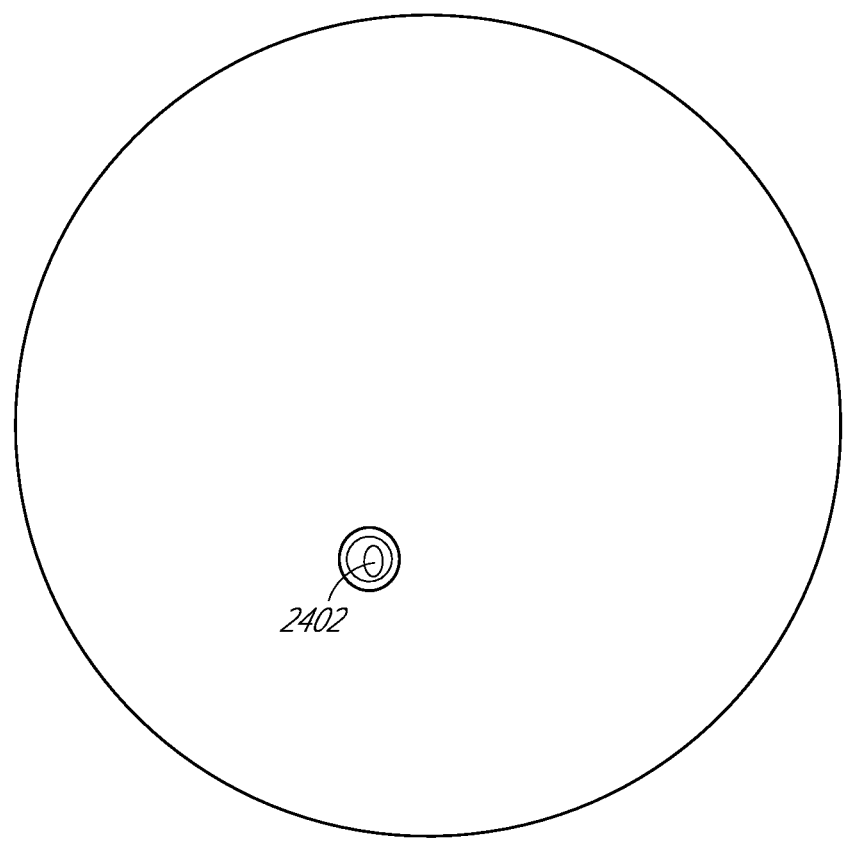
FIG. 9 represents system function in a graphical output.

A matrix of data containing the spatial distributions of the parameters determined can be plotted as individual color-coded heat maps or contour maps for each parameter, as a means for quantitative inspection, feedback and presentation. FIG. 9 illustrates one such map 2400. It depicts how a defect 2402 may be portrayed. But it is possible to show any of the further refined subject matters in FIG. 7. Once quantitative data has been obtained, providing such output is merely a matter of changing the code in the plotting program/script.

Such information and/or other information treated below may be shown on a computer monitor or dedicated system display and/or it may be recorded for later reference or use for analysis on digital media. In addition, each wafer spatial distribution can be cross-correlated by referencing with ellipsometry data to correct for layer thickness variability and cross-calibrated with independent contamination characterization data obtained, for example, by Total Reflection X-ray Fluorescence (TXRF), Time of Flight Secondary Ion Mass Spectroscopy (TOF-SIMS) and the like. These initial or corrected spatial distributions can then be compared to those from wafers known to be within specification, to determine if the samples in question have any defects or problematic features which warrant further testing. In general, however, it is desirable to use low-cost SHG and other methods hereof calibrated with, by or against slow and expensive direct methods like TXRF, etc.

Human decisions may be employed (e.g., in inspecting a generated heat map 2400) initially in determining the standard for what is an acceptable or unsatisfactory wafer, until the tool is properly calibrated to be able to flag wafers autonomously. For a well-characterized process in a fab, human decisions would then only need to be made to determine the root cause of any systemic problem with yields, based on the characteristics of flagged wafers.

However implemented, FIG. 10 provides a plot 2500 illustrating a first method embodiment hereof that may be used in making such determinations. This method, like the others discussed and illustrated below relies on characterizing SHG response with multiple shutter blocking events in which interrogation laser is gated for periods of time.

In this first example, a section of a sample to be interrogated is charged (typically by a laser) to saturation. In this example, a single source is used to generate as pump beam and probe beam, although separate pump and probe sources can be used in other embodiments. During which time, the SHG signal may be monitored. The saturation level may be known by virtue of material characterization and/or observing asymptotic behavior of the SHG signal intensity associate with charging ($I_{ch}$). Upon (or after) reaching saturation, the electromagnetic radiation from the laser (pump beam) is blocked from the sample section. The laser (probe beam) is so-gated for a selected period of time ($T_{b/1}$). After gating ceases, an SHG intensity measurement ($I_{dch1}$) is made with the laser (probe beam) exposing the surface, thus observing the decay of charge at a first discharge point. After charging the material section (with the pump beam) to saturation again over a period of time ($t_{ch}$), a second blocking event occurs for a time ($t_{b/2}$) different than the first in order to identify another point along what will become a composite decay curve. Upon unblocking the laser (probe beam), SHG signal intensity ($I_{dchs2}$) is measured again. This reduced signal indicates charge decay over the second gating event or blocking interval. Once-again charged to saturation by the laser (pump beam), a third differently-timed blocking event ($t_{b/3}$) follows and subsequent SHG interrogation and signal intensity measurement ($I_{dch3}$) is made for a third measurement of charge decay in relation to SHG intensity.

Although in the above example, the sample is charged to a saturation level, in other examples, the sample can be charged to a charge level below saturation. Although in the above example, the three blocking times $t_{b/1}$, $t_{b/2}$ and $t_{b/3}$ are different, in other examples, the three blocking times $T_{b/1}$, $t_{b/2}$ and $t_{b/3}$ can be the same. In various examples, the sample can be charged to a charging level initially and the SHG intensity measurement a ($I_{dch1}$), ($I_{dch2}$) and ($I_{dch3}$) can be obtained at different time intervals after the initial charging event.

As referred to above, these three points (corresponding to $I_{dch1}$, $I_{dch2}$ and $I_{dch3}$) can be used to construct a composite charge decay curve. It is referred to herein as a "composite" curve in the sense that its components come from a plurality of related events. And while still further repetition (with the possibility of different gating times employed to generate more decay curve data points or the use of same-relation timing to confirm certainty and/or remove error from measurements for selected points) may be employed so that four or more block-then-detect cycles are employed, it should be observed that as few as two such cycles may be employed. Whereas one decay-related data point will not offer meaningful decay curve characterization, a pair defining a line from which a curve may be modeled or extrapolated from to offer some utility, whereas three or more points for exponential decay fitting will yield an approximation with better accuracy. Stated otherwise, any simple (e.g., not stretched by dispersive transport physics) decay kinetics has a general formula: Measurable(t)=$M_0$*exp(-t/tau) so to find two unknown parameter $M_0$ and tau at least 2 points are needed assuming this simple kinetics. In dispersive (i.e., non-linear) kinetics it is desirable to measure as many point as possible to extract (n−1)-order correction parameters if n-points are measured and then apply a model appropriate for that order of approximation. Also, that set of measurements is to be measured for different electric fields (E) to be real practical and precise with the tau to assign it for a certain type of defects.

The method above can provide parameter vs. time (such as interfacial leakage current or occupied trap density v. time) kinetic curve by obtaining measurements at a few time points. A time constant ($\tau$) can be extracted from the parameter vs. time kinetic curve. The time constant can be attributed to a time constant characteristic for a certain type of defect.

In any case, the decay-dependent data obtained may be preceded (as in the example) by SHG data acquisition while saturating the material with the interrogation (or probe) laser. However, charging will not necessarily go to saturation (e.g., as noted above). Nor will the measurement necessary be made prior to the blocking of a/the charging laser. Further, the charging will not necessarily be performed with the interrogation/probe laser (e.g., see optional pump/probe methodology cited above).

Regardless, after the subject testing at one sample site, the sample material is typically moved or indexed to locate another section for the same (or similar) testing. In this manner, a plurality of sections or even every section of the sample material may be interrogated and quantified in scanning the entire wafer as discussed above.

FIG. 11 and plot 2600 illustrate an alternative (or complimentary approach) to acquiring charge decay related data by scanning is shown in plot 2600. In this method, after charging to saturation a/the first time, continuous (or at least semi-continuous) discharge over multiple blocking time intervals ($t_{b/1}$, $t_{b/2}$, $t_{b/3}$) is investigated by laser pulses from an interrogation or a probe laser measuring different SHG intensities ($I_{dch1}$, $I_{dch2}$, $I_{dch3}$). The intensity and/or frequency of the laser pulses from the interrogation/probe laser are selected such that the average power of the interrogation/probe laser is reduced to avoid recharging the material between blocking intervals while still obtaining a reasonable SHG signal. To do so, as little as one to three laser pulses may be applied. So-reduced (in number and/or power), the material excitation resulting from the interrogation or probe laser pulses may be ignored or taken into account by calibration and or modeling considerations.

In various embodiments, a separate pump source can be used for charging. However, in some embodiments, the probe beam can be used to charge the sample.

In any case, the delay between pulses may be identical or tuned to account for the expected transient charge decay profile or for other practical reason. Likewise, while the delay is described in terms of "gating" or "blocking" above, it is to be appreciated that the delay may be produced using one or more optical delay lines as discussed above in connection with FIG. 6C. Still further, the same may hold true for the blocking/gating discussed in association with FIG. 10.

Further, as above, the method in FIG. 11 may be practiced with various modifications to the number of blocking or delay times or events. Also, SHG signal may or may not be measured during charge to saturation. Anyway, the method in FIG. 11 may be practiced (as illustrated) such that the final gating period takes the SHG signal to null. Confirmation of this may be obtained by repeating the method at the same site in a mode where charging intensity ($I_{ch}$) is measured or by only observing the SHG signal in (re)charging to saturation.

Figure 12A:
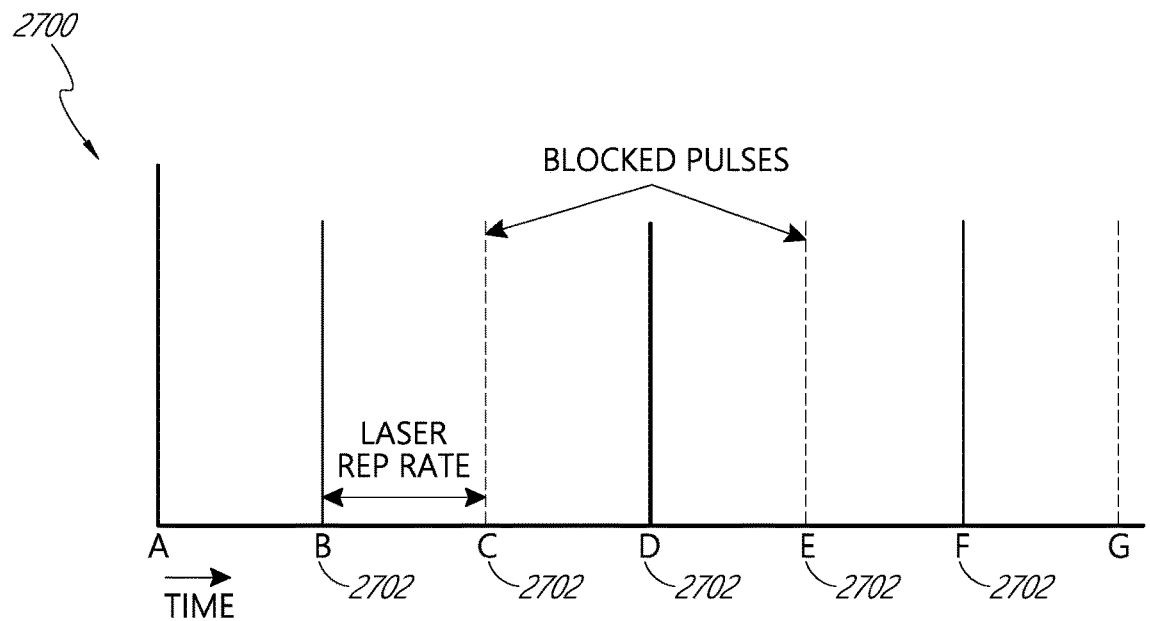
FIGS. 12A-12E plot time dynamics associated with the system in FIG. 6C that may be employed in the methods of FIGS. 10 and 11.

FIGS. 12A-12E are instructive regarding the manner in which the subject hardware is used to obtain the decay-related data points. FIG. 12A provides a chart 2700 illustrating a series of laser pulses 2702 in which intermediate or alternating pulses are blocked by shutter hardware (e.g., as described above) in a so-called "pulse picking" approach. Over a given time interval, it is possible to let individual pulses through (indicated by solid line) and block others (as indicated by dashed line).

Figure 12B:
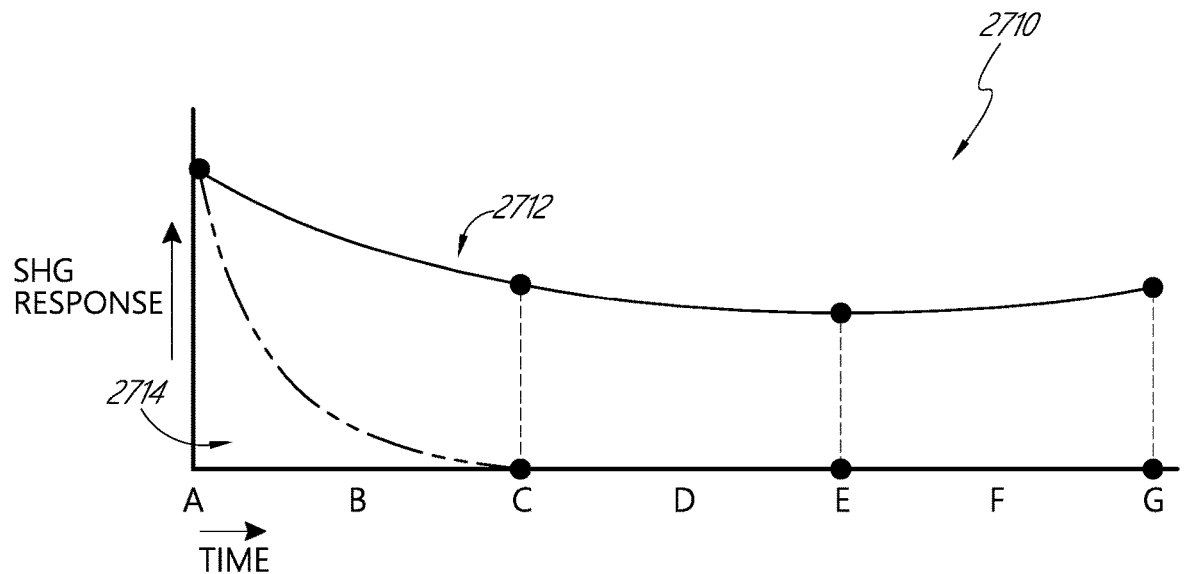

FIG. 12B provides a chart 2710 illustrating the manner in which resolution of a blocking technique for SHG investigation can be limited by the repetition (rep) rate of the probe laser. Specifically, when presented with a decay curve like decay curve 2712 it is possible to resolve the time delay profile with blocking of every other pulse using a pulsed laser illustrated to operate at the same time scale as in FIG. 12A. However, a shorter curve 2714 cannot be resolved or observed under such circumstances. As such, use optical delay stage(s) can offer additional utility.

Figure 12C:
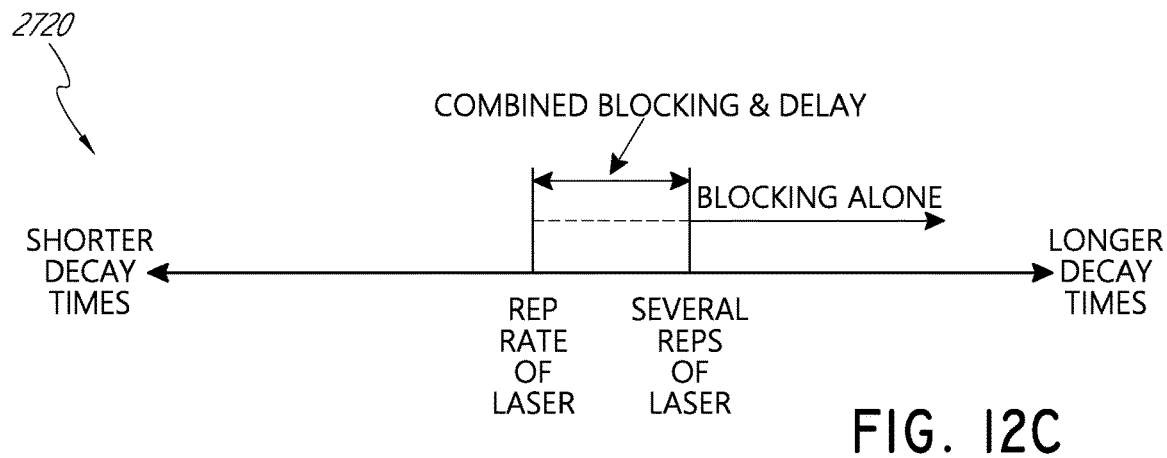

Accordingly, chart 2720 in FIG. 12C illustrates (graphically and with text) how blocking and introducing a delay with respect to a reference time associated with charging the sample can offer overlapping areas of usefulness, in terms of the decay time of the curve relative to the rep rate of the laser. It also shows how there are short time ranges when only delay stages would allow interrogation of the decay curve, and longer time ranges when only blocking the pumping and/or the probing beam would be practical.

Figure 12D:
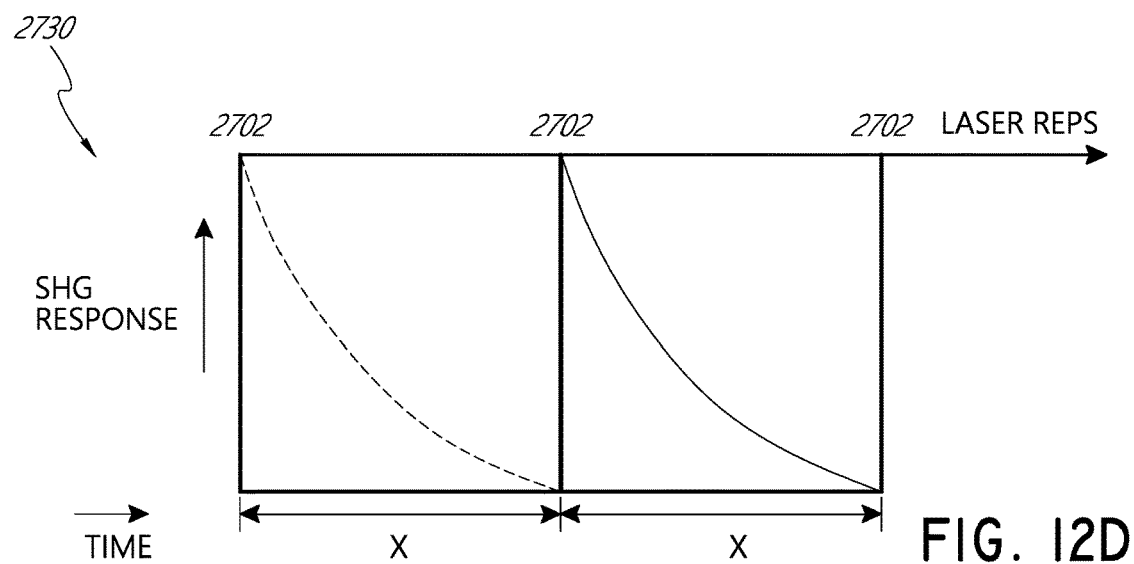
Figure 12E:
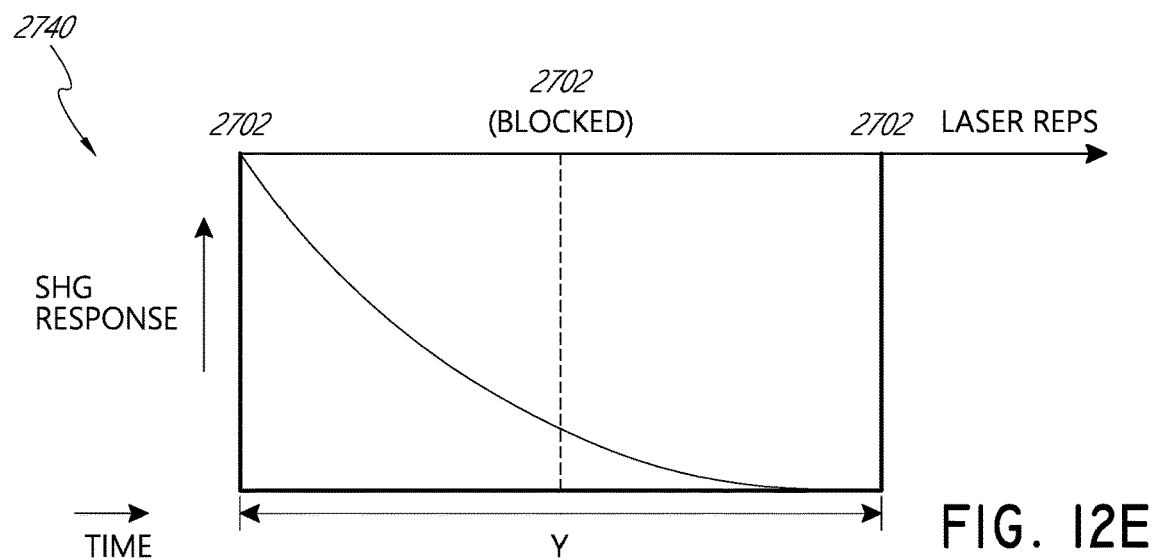

FIGS. 12D and 12E further illustrate the utility of the combined block/delay apparatus. Chart 2730 illustrates exemplary SHG signals produced by individual laser pulses 2702. With a delay stage alone, only the range (X) between each such pulse may be interrogated by varying optical delay. In contrast, additional utility over a range (Y) may be achieved with a system combining a delay stage and blocking or shutter means such as a chopper, shutter, or modulator. As illustrated by chart 2740, such a system is able to measure decay curves (and their associated time constants) in the range from one to several pulse times.

Figure 13:
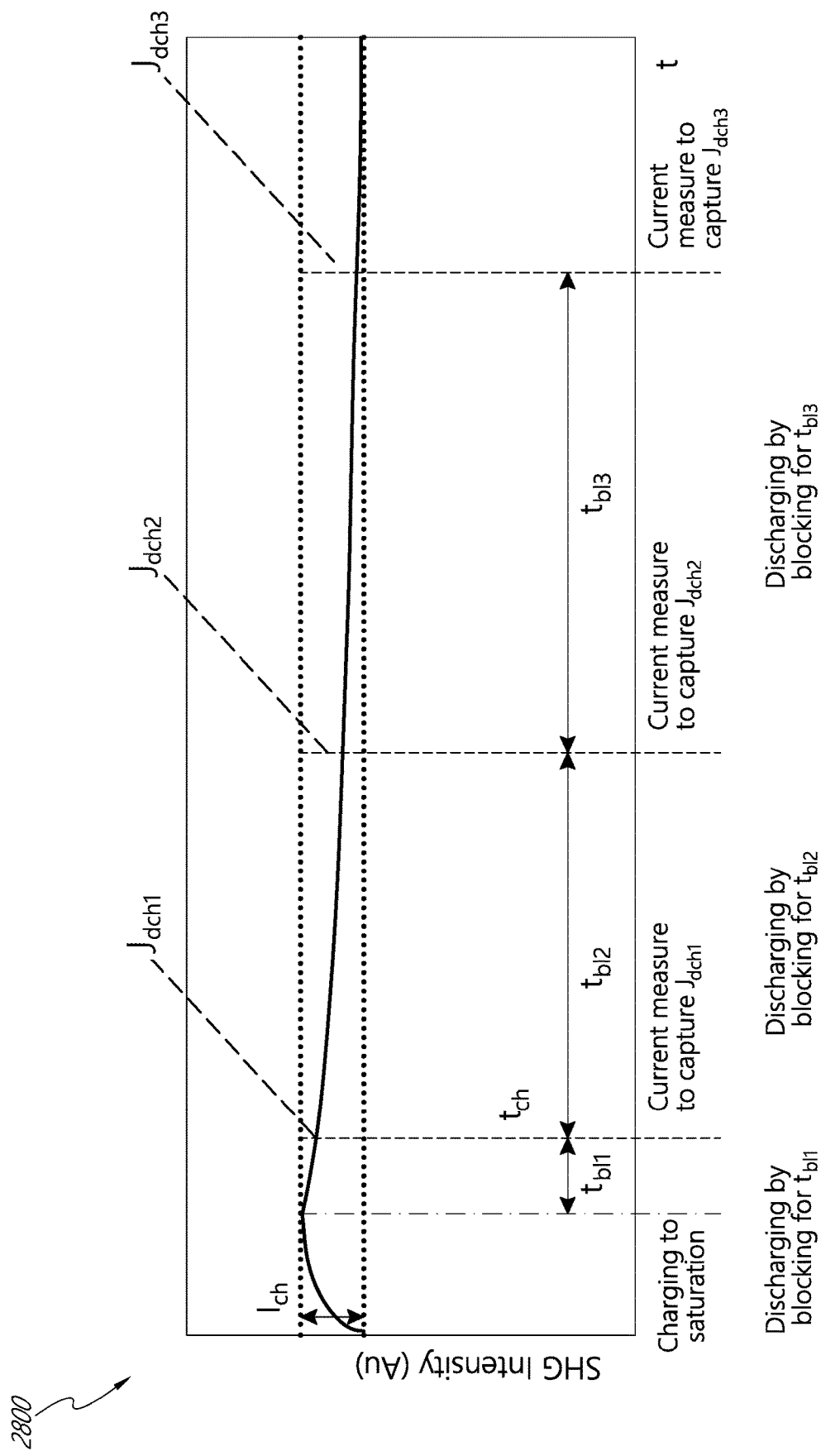
FIG. 13 plots a current-based interrogation method for observing transient electric field decay.

FIG. 13 provides a plot 2800 illustrating a third method embodiment hereof. This embodiment resembles that in FIG. 11, except that discharge current ($J_{dch1}$, $J_{dch2}$, $J_{dch3}$) is measured at time intervals (e.g., $t_i=t_0$, $2t_0$, $3t_0$, $7t_0$, $10t_0$, $20t_0$, $30t_0$, $70t_0$—basically according to a log time scale vs. linear time—where $t_0$ is a scale parameter of about $10^{-6}$ sec or $10^{-3}$ sec when measurement is started) after charging the material with a laser (optionally monitoring or capturing its SHG intensity ($I_{ch}$) signal) or other electro-magnetic radiation source and then blocking or otherwise stopping the laser radiation application to the sample, thereby allowing discharge. This approach gives an estimation of the mobile carrier lifetime in the substrate by the moment after the e-h-plasma in the substrate is decayed and when the discharge current starts to be seen, thus offering an important physical parameter of the wafer. And after carrier lifetime is determined, the discharge of current can be interpreted in its time dependence (i.e., its kinetics regarding charge decay) in the same manner as if it were obtained by SHG sensing of discharged charge.

Various embodiments can be used to measure time constant (e.g., for decay) having a range of values. For example, the time constants can range between 0.1 femtosecond and 1 femtosecond, 1 femtosecond and 10 femtoseconds, 10 femtoseconds and 100 femtoseconds, 100 femtoseconds and 1 picosecond, between 1 picosecond and 10 picoseconds, between 10 picoseconds and 100 picoseconds, between 100 picoseconds and 1 nanosecond, between 1 nanosecond and 10 nanoseconds, between 10 nanosecond and 100 nanoseconds, between 100 nanoseconds and 1 microsecond, between 1 nanoseconds and 100 microseconds, between 100 microseconds and 1 millisecond, between 1 microsecond and 100 milliseconds, between 100 microsecond and 1 second, between 1 second and 10 seconds, between 10 second and 100 seconds or larger or smaller. Likewise, time delays (A) for example between the probe and pump (or pump and probe) can be, for example, between 0.1 femtosecond and 1 femtosecond, 1 femtosecond and 10 femtoseconds, 10 femtoseconds and 100 femtoseconds, 100 femtoseconds and 1 picosecond, between 1 picosecond and 10 picoseconds, between 10 picoseconds and 100 picoseconds, between 100 picoseconds and 1 nanosecond, between 1 nanosecond and 10 nanoseconds, between 10 nanosecond and 100 nanoseconds, between 100 nanoseconds and 1 microsecond, between 1 nanoseconds and 100 microseconds, between 100 microseconds and 1 millisecond, between 1 microsecond and 100 milliseconds, between 100 microsecond and 1 second, between 1 second and 10 seconds, between 10 second and 100 seconds. Values outside these ranges are also possible.

Figure 14A:
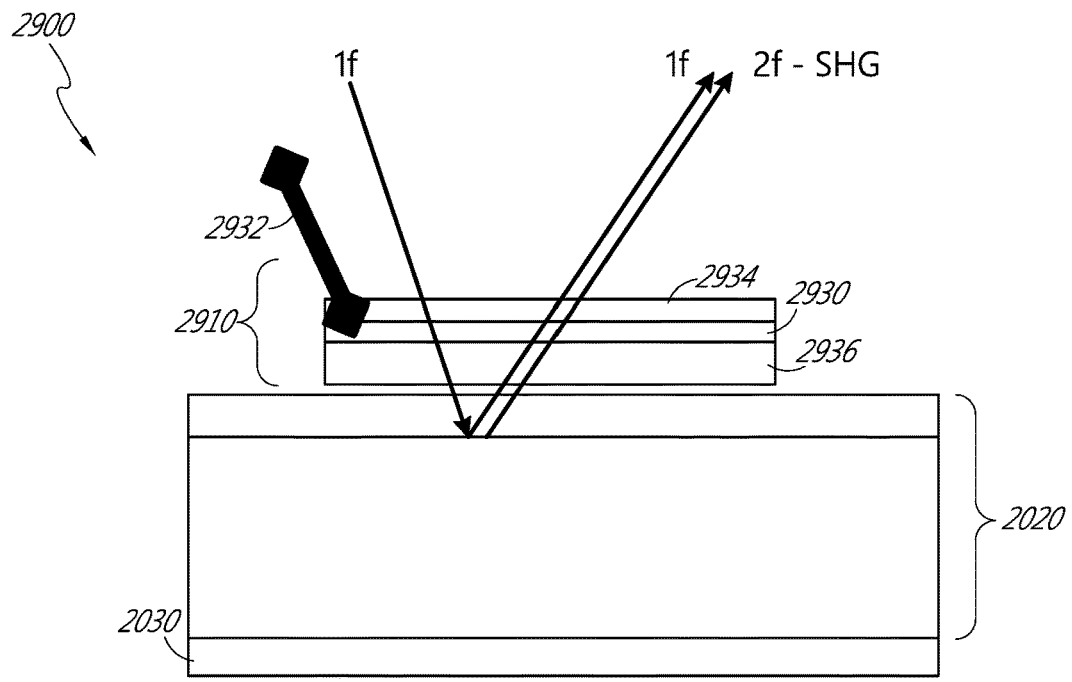
FIGS. 14A and 14B illustrate hardware configurations that may be employed in the method of FIG. 13.
Figure 14B:
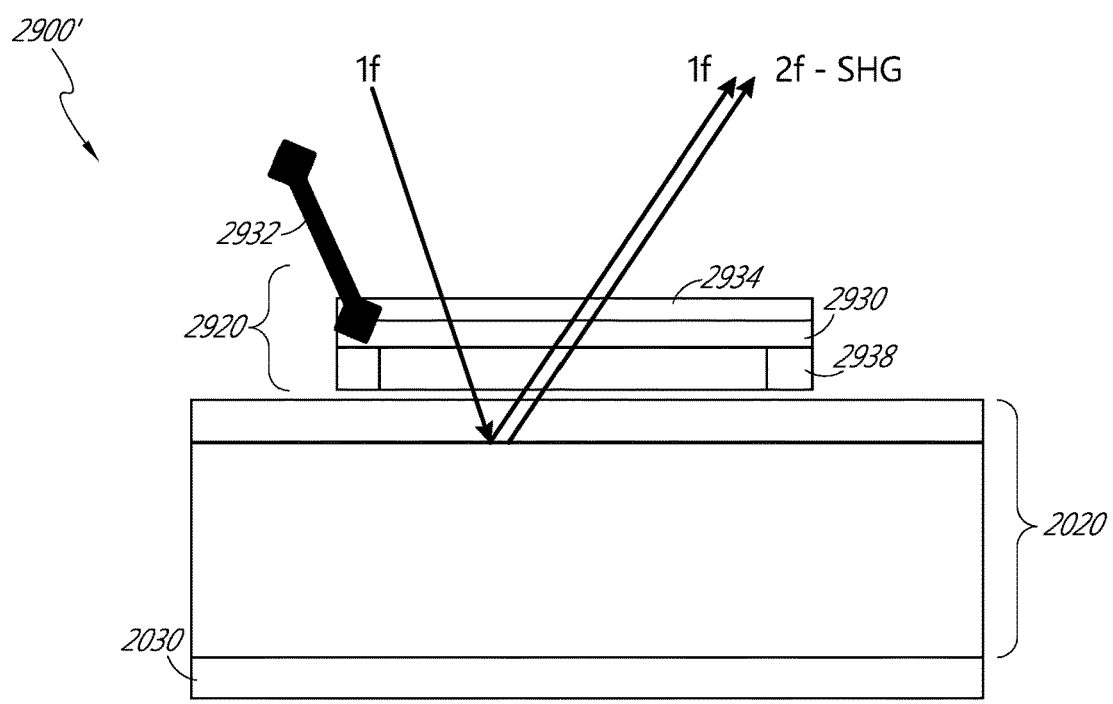

Various physical approaches can be taken in providing a system suitable for carrying out the method in FIG. 13—which method, notably, may be modified like those described above. Two such approaches are illustrated in FIGS. 14A and 14B.

Systems 2900 and 2900' use gate electrodes 2910 and 2920, respectively, made of a conductive material that is transparent in the visible light range. Such an electrode may touch a wafer 2020 to be inspected, but need not as they may only be separated by a minimal distance. In various implementations, the electric field in the dielectric can be estimated by extracting the electrode-dielectric-substrate structure parameters using AC measurement of the Capacitance-Voltage curve (CV-curve). CV-curve measurement can be done by using a standard CV-measurement setup available on the market, connected to a material sample in the subject tool (e.g., the applied voltage is to provide the electric field in the dielectric between about 0.1 MV/cm and about 5 MV/cm). The wafer may be held upon a conductive chuck 2030 providing electrical substrate contact. Another alternative construction for a gate electrode would be an ultrathin Au film or Al film on a glass of 10-30 A thickness which can reduce the sensitivity due to absorption of some photons by the thin semi-transparent metal layer.

However, electrodes 2910 and 2920 present no appreciable absorption issues (although some refraction-based considerations may arise that can be calibrated out or may be otherwise accounted for in the system). These electrodes may comprise a transparent conductor gate layer 2930 made of a material such as ZnO, SnO or the like connected with an electrical contact 2932. An anti-reflective top coat 2934 may be included in the construction. Gate layer 2930 may be set upon a transparent carrier made 2936 of dielectric ($SiO_2$) with a thickness ($D_{gc}$) as shown. In various embodiments, the transparent carrier comprises an insulator that is used as a gate for a noncontact electrode that may employ for example capacitive coupling to perform electrical measurements, similar to those described in the portion of U.S. Provisional Application No. 61/980,860, filed on Apr. 17, 2014, titled "WAFER METROLOGY TECHNOLOGIES," referred to as Section IV entitled, "FIELD-BIASED SHG METROLOGY". As the wafer is charged from the incoming laser radiation, the electric field across one or more of its interfaces will change, and the layers of the wafer should capacitavely couple with the plates in the electrode similar to a plate capacitor. The charging of the electrode will involve movement of charge carriers that will be measured as current.

$D_{gc}$ would be calibrated by measuring CV curve on the semiconductor substrate with a non-invasive approach and used in electric field (E) calculation when applied voltage is known. A negligible gap distance between the gate and sample can be an air gap. Alternatively the electrode can be directly in contact with the sample rather than being separated by an air gap or dielectric. Accordingly normal CV or IV measurements may be performed in various embodiments.

Or given a close refractive index match between water and $SiO_2$, filling the gap with deionized water may be helpful in reducing boundary-layer reflection without any ill effect (or at least one that cannot be addressed). Deionized (or clean-room grade) water can maintain cleanliness around the electrically sensitive and chemically pure substrate wafers. Deionized water is actually less conductive than regular water.

In FIG. 14B, a related construction is shown with the difference being the architecture of the carrier or gate-holder 2938. Here, it is configured as a ring, optimally formed by etched away in the center and leaving material around the electrode perimeter as produced using MEMS techniques. But in any case, because of the large unoccupied zone through with the laser and SHG radiation must pass, it may be especially desirable to fill the same with DI water as described above.

Regardless, in the overall electrode 2910, 2920 constructions each embodiment would typically be stationary with respect to the radiation exciting the material in use. Prior to and after use, the electrode structure(s) may be stowed by a robotic arm or carriage assembly (not shown).

As describe above, in various embodiments the electrode directly contacts the wafer to perform electrical measurements such as measuring current flow. However, non-contact methods of measuring current, such as for example using electrodes that are capacatively coupled with the sample, can also be used.

The systems and methods described herein can be used to characterize a sample (e.g., a semiconductor wafer or a portion thereof). For example, the systems and methods described herein can be used to detect defects or contaminants in the sample as discussed above. The systems and methods described herein can be configured to characterize the sample during fabrication or production of the semiconductor wafer. Thus, the systems and methods can be used along a semiconductor fabrication line in a semiconductor fabrication facility. The systems and methods described herein can be integrated with the semiconductor fabrication/production line. The systems and methods described herein can be integrated into a semiconductor fab line with automated wafer handling capabilities. For example, the system can be equipped with an attached Equipment Front End Module (EFEM), which accepts wafer cassettes such as a Front Opening Unified Pod (FOUP). Each of these cassettes can be delivered to the machine by human operators or by automated cassette-handling robots which move cassettes from process to process along fabrication/production line.

In various embodiments, the system can be configured such that once the cassettes are mounted on the EFEM, the FOUP is opened, and a robotic arm selects individual wafers from the FOUP and moves them through an automatically actuated door included in the system, into a light-tight process box, and onto a bias-capable vacuum chuck. The chuck may be designed to fit complementary with the robotic arm so that it may lay the sample on top. At some point in this process, the wafer can be held over a scanner for identification of its unique laser mark.

Accordingly, a system configured to be integrated in a semiconductor fabrication/assembly line can have automated wafer handling capability from the FOUP or other type of cassette; integration with an EFEM as discussed above, a chuck designed in a way to be compatible with robotic handling, automated light-tight doors which open and close to allow movement of the robotic wand/arm and software signaling to EFEM for wafer loading/unloading and wafer identification.

Part III

FIGS. 15A and 15B show suitable hardware for use in the subject systems and methods as further described in the portion of U.S. Provisional Application No. 61/980,860, filed on Apr. 17, 2014, titled "WAFER METROLOGY TECHNOLOGIES," referred to as Section I entitled "PUMP AND PROBE TYPE SHG METROLOGY". Other system and method options are presented in the portion of U.S. Provisional Application No. 61/980,860, filed on Apr. 17, 2014, titled "WAFER METROLOGY TECHNOLOGIES," referred to as Section II entitled "CHARGE DECAY MEASUREMENT SYSTEMS AND METHODS," for example, as to intermediate optics, the inclusion of optical delay line(s) and optional electrode features.

As shown, system 3000 includes a primary or probe laser 3010 for directing an interrogation beam 3012 of electromagnetic radiation at a sample wafer 3020, which is held by a vacuum chuck 3030. As illustrated in FIG. 15B, the chuck 3030 includes or is set on x- and y-stages and optionally also a rotational stage for positioning a sample site 3022 across the wafer relative to where the laser(s) are aimed. The x-y stage enables scanning multiple wafer surface sites or locations 3022 without movement of other hardware. A rotational stage optionally enables assessing crystal structure effects on SHG. Further optional features, aspects and/or uses of chuck 3030 are presented elsewhere in this application entitled. The sample site 3022 can include one or more layers. The sample site 3022 can comprise a composite substrate including at least two layers. The sample site 3022 can include an interface between two dissimilar materials (e.g., between two different semiconductor materials, between two differently doped semiconductor materials, between a semiconductor and an oxide, between a semiconductor and a dielectric material, between a semiconductor and a metal or an oxide and a metal).

When system 3000 is in use, a beam 3014 of reflected radiation directed at a detector 3040 will include an SHG signal. The detector 3040 may be any of a photomultiplier tube, a CCD camera, an avalanche detector, a photodiode detector, a streak camera and a silicon detector. System 3000 may also include one or more shutter-type devices 3050. The type of shutter hardware used will depend on the timeframe over which the laser radiation is to be blocked, dumped or otherwise directed away from the sample site 3022. An electro-optic blocking device such as a Pockel's Cell or Kerr Cell can be used to obtain very short blocking periods (i.e., with actuation times on the order of $10^{-9}$ to $10^{-12}$ seconds).

For longer blocking time intervals (e.g., from about $10^{-5}$ seconds and upwards) mechanical shutters or flywheel chopper type devices may be employed. However, electro-optic blocking devices will allow a wider range of materials to be tested in accordance with the methods below. A photon counting system 3044 capable of discretely gating very small time intervals, typically, on the order of picoseconds to microseconds can be employed to resolve the time-dependent signal counts. For faster-yet time frames optical delay line(s) may be incorporated as noted above.

System 3000 can include an additional electromagnetic radiation source 3060 also referred to as a pump source. In various implementations, the radiation source 3060 can be a laser illustrated as emitting a directed beam 3062 or a UV flash lamp emitting a diverging or optically collimated pulse 3064. In the case of a laser source, its beam 3062 may be collinear with beam 3012 (e.g., as directed by additional mirrors or prisms, etc.) Source 3060 output wavelengths of light may be anywhere from about 80 nm and about 1000 nm. Using shorter wavelengths in this range (e.g. less than about 450 nm), is possible to drive charge excitation using fewer photons and/or with lower peak intensities than at longer wavelengths.

For a flash lamp, energy per flash or power level during flash may be substrate material dependent. A flashlamp producing a total energy of 1 J to 10 kJ per flash would be appropriate for fully depleted silicon-on-insulator (FD-SOI). However a pulsed or constant UV source would be viable as well. The important factor in the pump characteristics and use is that charge carriers are injected into the dielectric of the material to be interrogated. Manufacturers of suitable flash lamps include Hellma USA, Inc. and Hamamatsu Photonics K.K.

When a laser is employed as source 3060, it may be any of a nanosecond, picosecond or femtosecond or faster pulse laser source. It may even be a continuous solid-state laser. In various embodiments, the pump source is tunable in wavelength. Commercially available options regarding lasers which are tunable include Spectra Physics' Velocity and Vortex Tunable Lasers. Additional tunable solid state solutions are available from LOTIS Ltd.'s LT-22xx series of solid state lasers.

Whether provided as a laser or a flash lamp, pump source 3060 can be selected for relatively high average power. This could be from about 10 mW to about 10 W, but more typically from about 100 mW to about 4 W, depending on material to be interrogated (as, again, the consideration is ensuring that charge carrier mobility is induced in a way such that charge carriers are injected into the interface of the material (e.g., the dielectric interface), which can be material specific. The average power of the pump source 3060 is selected to be below the optical damage threshold of the material. For example, pump source 3060 can be selected to have an average optical power between 1-2 W when the interrogating material comprises silicon so as to not exceed the optical damage threshold for silicon.

Probe laser 3010 may be any of a nanosecond, picosecond or femtosecond or faster pulse laser source. Two options are currently commercially available regarding lasers have the peak power, wavelength and reliability needed are doped fiber and Ti:Sapphire units. Coherent's VITESSE and Spectra Physics' MAI TAI lasers are examples of suitable Ti:Sapphire devices. Femtolasers Gmbh and others manufacture also manufacture other relevant Ti:Sapphire devices. Suitable doped fiber lasers are produced by IMRA, OneFive, and Toptica Photonics. Pico- and/or nano-second lasers from many manufacturers, such as Hamamatsu, may be options as well depending on the substrate material and pump type. Laser 3010 may operate in a wavelength range between about 100 nm to about 2000 nm with a peak power between about 10 kW and 1 GW, but delivering power at an average below about 150 mW.

Various other optional so-called "intermediate" optical components may be employed in system 3000. For example, the system 3000 may include a dichroic reflective or refractive filter 3070 for selectively passing the SHG signal coaxial with reflected radiation directly from laser 3010 and/or source 3060. Alternatively, a prism may be employed to differentiate the weaker SHG signal from the many-orders-of-magnitude-stronger reflected primary beam. However, as the prism approach has proved to be very sensitive to misalignment, a dichroic system as referenced above may be preferred. Other options include the use of diffraction grating or a Pellicle beam splitter. An optical bundle 3080 for focusing and collimating/columniation optics may be provided. Alternatively, a filter wheel 3090, polarizer(s) 3092 and/or zoom len(s) 3094 units or assemblies may be employed in the system. Also, an angular (or arc-type) rotational adjustment (with corresponding adjustment for the detector) and in-line optical components may be desirable.

The output from the detector 3040 and/or the photon counting system 3044 can be input to an electronic device 3048. The electronic device 3048 can be a computing device, a computer, a tablet, a microcontroller or a FPGA. The electronic device 3048 includes a processor that may be configured to execute one or more software modules. In addition to executing an operating system, the processor may be configured to execute one or more software applications, including a web browser, a telephone application, an email program, or any other software application. The electronic device 3048 can implement the methods discussed herein by executing instructions included in a machine-readable non-transitory storage medium, such as a RAM, ROM, EEPROM, etc. The electronic device 3048 can include a display device and/or a graphic user interface to interact with a user. The electronic device 3048 can communicate with one or more devices over a network interface. The network interface can include transmitters, receivers and/or transceivers that can communicate such as, for example, wired Ethernet, Bluetooth®, or wireless connections.

Regarding other options, since an SHG signal is weak compared to the reflected beam that produces it, it is desirable to improve the signal-to-noise ratio of SHG counts. As photon counting gate times for the photon counting system 3044 decrease for the blocking and/or delay processes described herein, improvement becomes even more important. One method of reducing noise that may be employed is to actively cool the photon counter. This can be done using cryogenic fluids such as liquid nitrogen or helium or solid state cooling through use of a Peltier device. Others areas of improvement may include use of a Marx Bank Circuit (MBC) as relevant to shutter speed. Moreover, system 3000 may be incorporated in-line within a production line environment. Production line elements preceding or following system 100 may include any of epitaxial growth system, lithography and/or deposition (CVD, PVD, sputtering, etc.) systems.

Figure 16A:
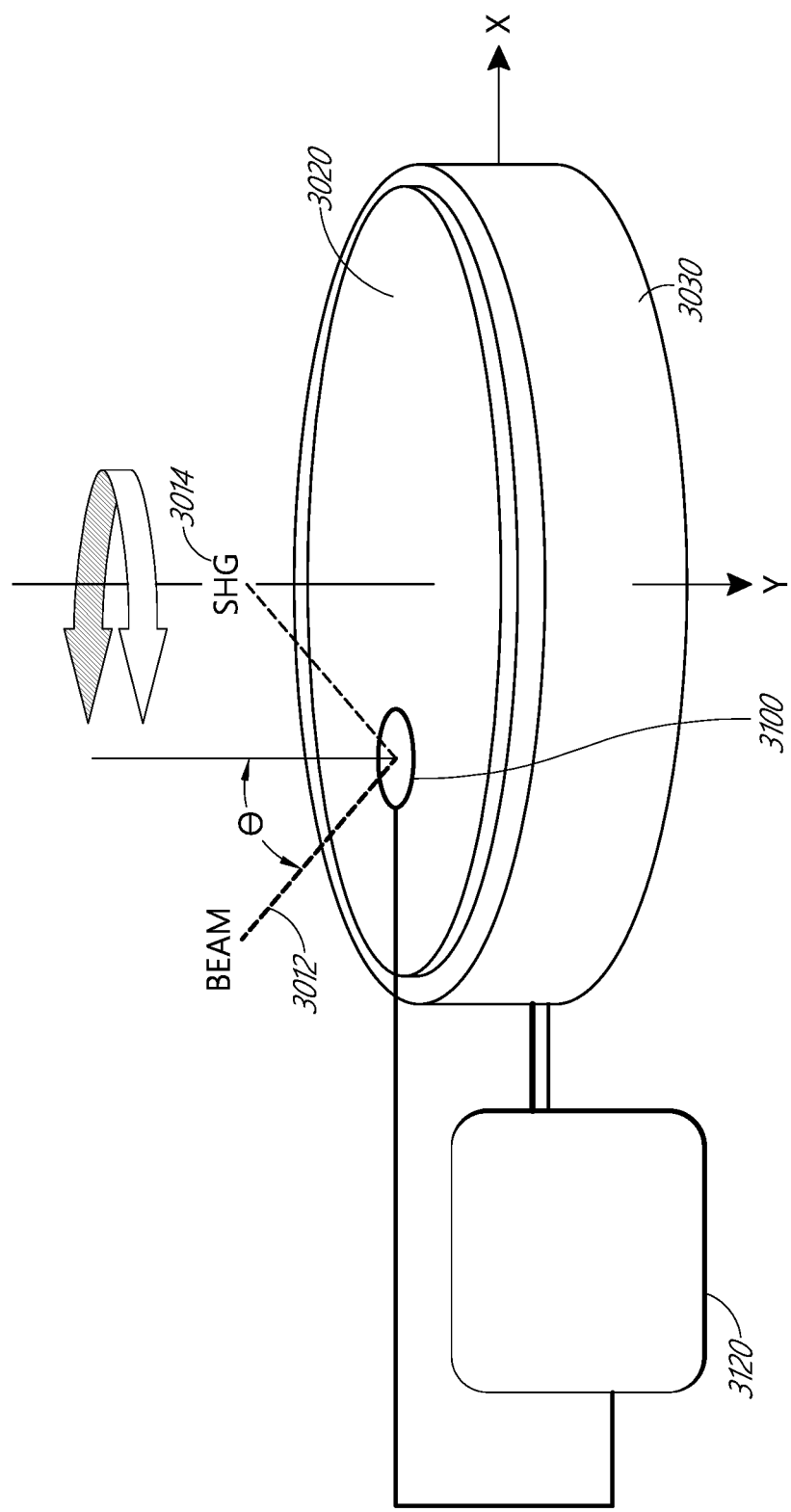
FIG. 16A is a perspective view of a first chuck configuration hereof.
Figure 16B:
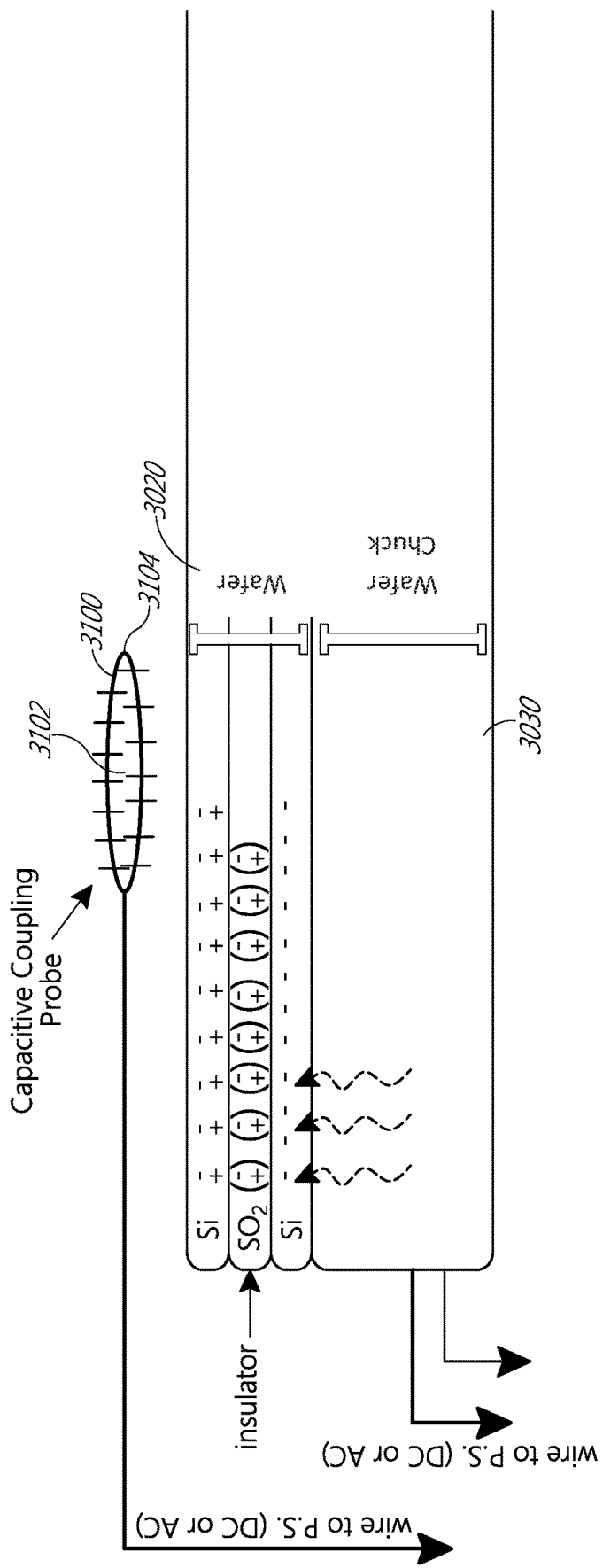
FIG. 16B is a side-sectional view of the chuck configuration in FIG. 16A.

In any case, FIGS. 16A and 16B provide views of a first set of purpose-specific chuck hardware that may be employed in the subject SHG system. The chuck 3030 holds a wafer 3020 by vacuum thereto or other means. The chuck 3030 is conductive and connected to a power supply. Optionally, a capacitive coupling probe 3100 is also connected to the power supply 3120. The power supply may be computer controlled, or at least its output is coordinated by computer for timing reasons as summarized above. The probe 3100 may likewise be controlled and/or monitored. It will be controlled in the sense that it will be part of a capacitive circuit attached to the power supply 3120. It may be monitored along with the chuck 3030 by a voltmeter to ensure that voltage is being induced as intended.

The probe 3100 includes a hole 3102 or port (e.g., 0.2 mm in diameter) in its ring 3104 to allow the optical beams 3012, 3014 (interrogation beam(s) and reflected SHG beam) to pass unblocked, and is fixed relative to the optics so that it moves or stays with the optical elements to remain centered on the (re)positioned sample site 3022 as the device surface is scanned. The coupling (indicated as having a positive "+" charge) is positioned close to the sample device surface (e.g., within about 1 mm to about 2 mm) but does not touch.

It is supported by a cantilever arm or otherwise. The probe 3100 may be provided as a ring 3104 as shown in FIG. 16B, or it may comprise a larger disc or plate.

With the example shown in cross section in FIG. 16B, a wafer 3020 or device surface (comprising silicon) is separated from a silicon bulk layer by $SiO_2$ insulator. Thus, as explained above, the need for inductive bias to the device surface because it is otherwise (at least substantially) electrically insulated or isolated from the underlying silicon in contact with the conductive chuck 3030.

Figure 17A:
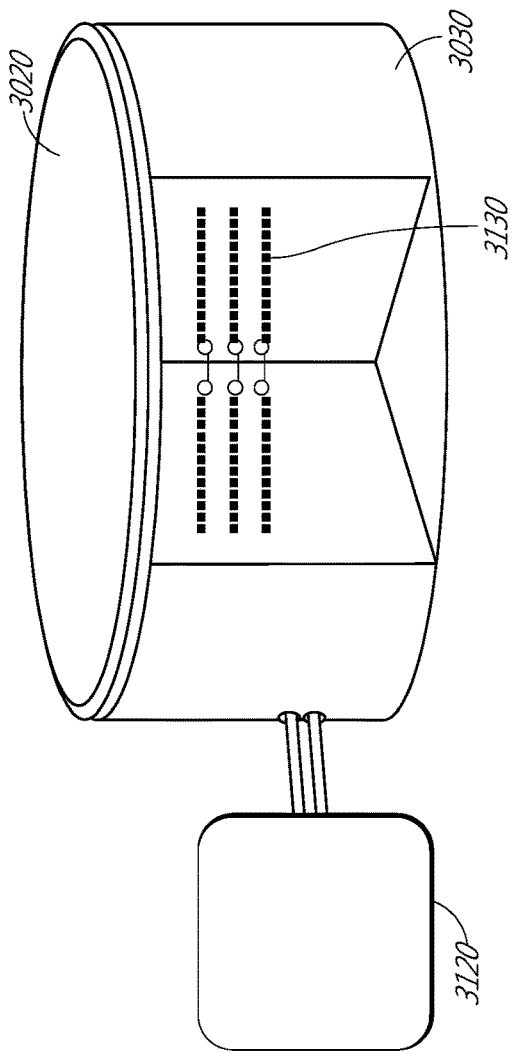
FIGS. 17A and 17B are partial cutaway, perspective views of a second chuck configuration hereof.
Figure 17B:
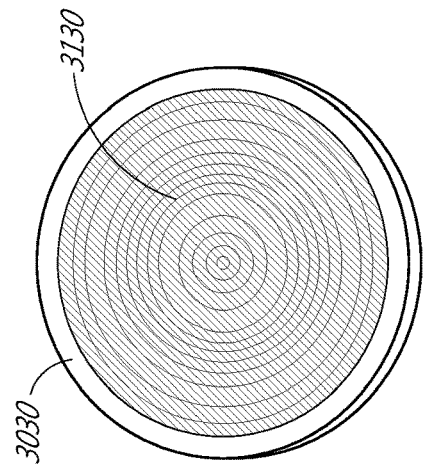
Figure 17C:
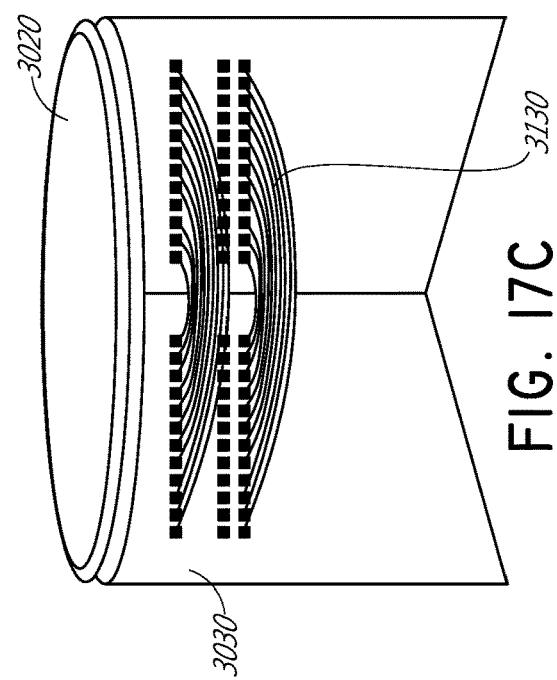
FIG. 17C is cutaway top view of the chuck in FIG. 17A/17B.

FIGS. 17A-17C detail an electromagnetic chuck 3030 that includes electrical coil(s) 3130 connected to a power supply 3120. In use, the wafer 3020 sits and is secured on top of the chuck 3030. When an alternating current (AC) is applied to the coil(s) 3130, this generates an alternating magnetic field through the wafer 3020. The magnetic field induces an electric potential across the wafer 3020 including its device surface. This electric field then enables the various modes of SHG interrogation noted above, some of which are detailed below. Alternatively, DC current may be applied to the coils 3130 which are oriented parallel to the chuck 3030, creating a constant magnetic field across the chuck for other effects as described above.

Figure 18A:
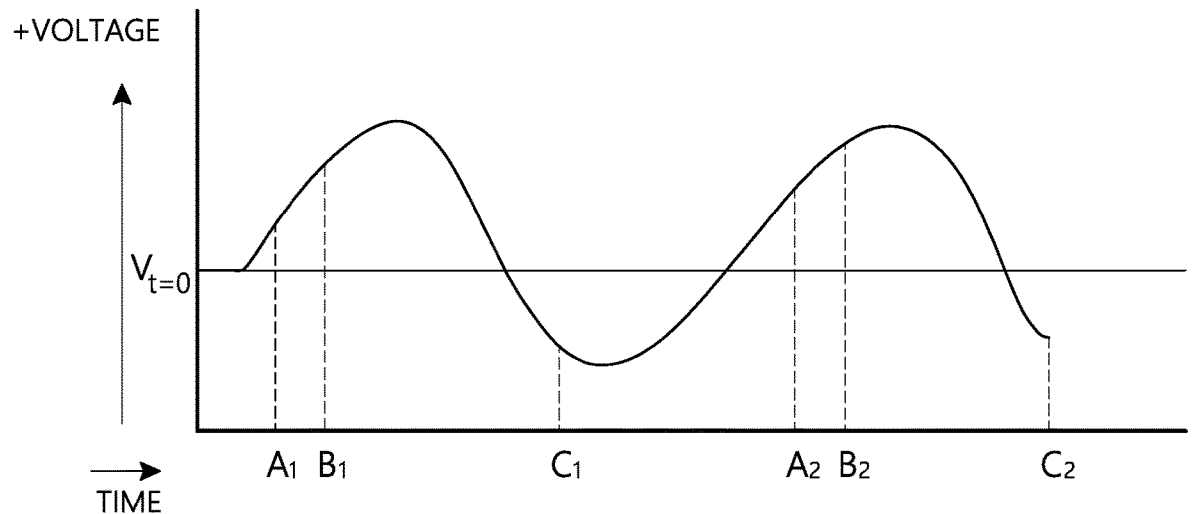
FIGS. 18A and 18B relate to AC voltage applied to and exhibited in a sample for DC bias probe elimination.
Figure 18B:
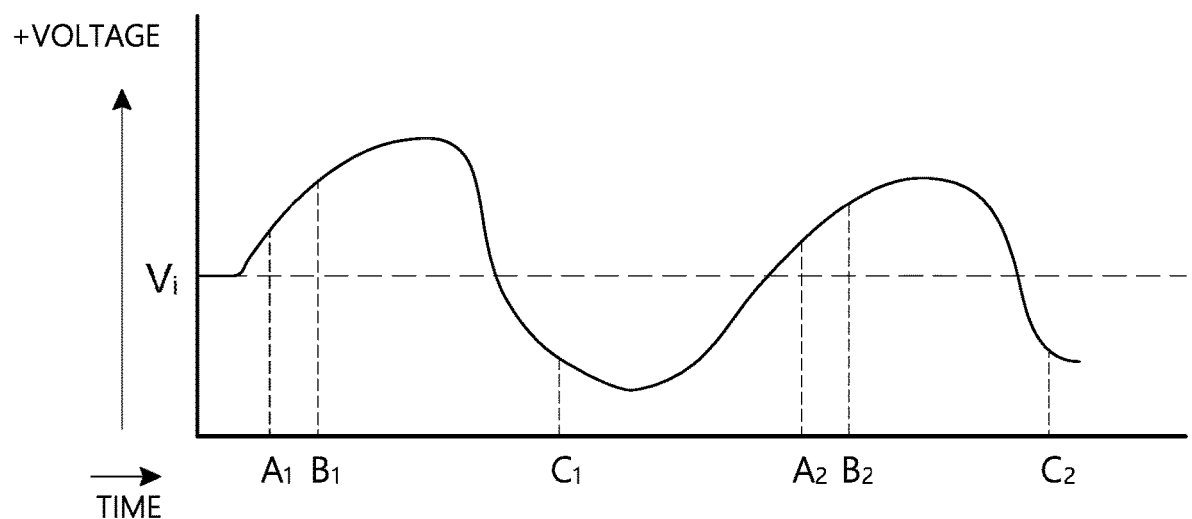
Figure 19A:
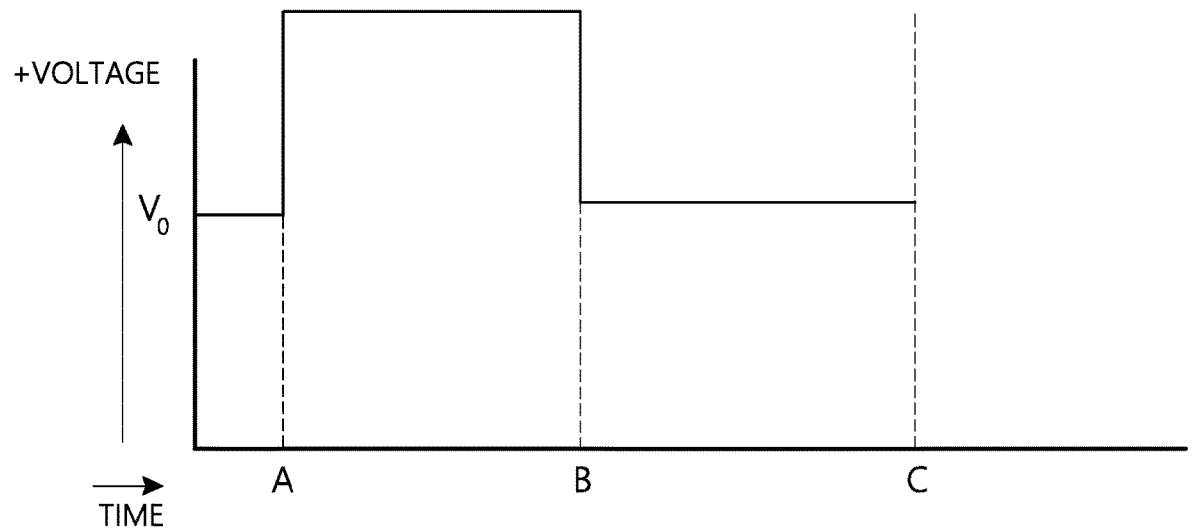
FIGS. 19A and 19B relate to AC voltage applied to and exhibited in a sample for testing leakage current.
Figure 19B:
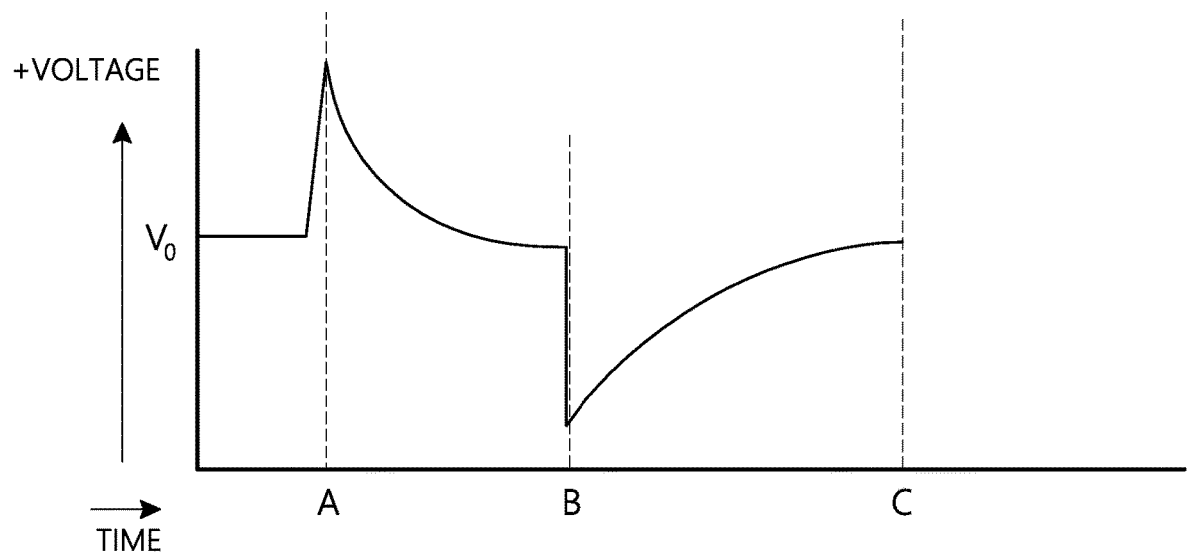

FIG. 18A shows an example AC voltage (V) profile (sinusoidal wave) applied to the substrate bulk layer over time. FIG. 18B shows a hypothetical response for induced voltage between the device and bulk layers ($V_i$) of the substrate on which the device is fabricated. In various embodiments, the substrate can comprise the silicon wafer or a portion of a semiconductor material. FIG. 19A shows an example AC voltage ($V_o$) profile (square wave) applied to the substrate bulk layer over time. FIG. 19B shows a hypothetical response for induced voltage between the device and bulk layers ($V_i$). Notably, the voltage input in either of FIG. 18A or 19A may differ from that shown, and could potentially be applied in steps, ramps, sine waves, or other forms.

More specifically regarding FIGS. 18A and 18B, as alluded to above, in order to minimize noise and obtain statistically relevant indicator(s) of SHG intensity as a function of voltage across the interfaces, multiple photon counting windows may be desirable. For such purposes, example points A1 and A2 are timed so that the voltage between the bulk and device layers, voltage A, is the same for both points. This is true for example points B1 and B2 at voltage B, and example points C1 and C2 at voltage C. Using voltage A as an example, SHG is recorded, and counts at points A1 can be summed with counts at point A2 and further at A3, A4, $A_n$ . . . in an arbitrarily long series depending on the desired measurement time. The total number of counts measured in this period is then divided by the time over which this "gate" spans as a way of finding the average number of counts per second, so that SHG intensity can be plotted as a function of bulk-device voltage A. The same method can be used to obtain measurements for voltage B at points B1 and B2 as well as at B3, B4, $B_n$ . . . in an arbitrarily long series depending on the desired measurement time. The total number of counts measured in this period is then divided by the time over which this "gate" spans as a way of finding the average number of counts per second, so that SHG intensity can be plotted as a function of bulk-device voltage B. Likewise, this method can be used to obtain measurements for voltage C at points C1 and C2 as well as at C3, C4, $C_n$ . . . in an arbitrarily long series depending on the desired measurement time. The total number of counts measured in this period is then divided by the time over which this "gate" spans as a way of finding the average number of counts per second, so that SHG intensity can be plotted as a function of bulk-device voltage C. Further details regarding the utility of SHG intensity as a function of bias voltage can be found in the DC biasing literature, an example of which is, "Charge Trapping in Irradiated SOI Wafers Measured by Second Harmonic Generation," IEEE Transactions on Nuclear Science, Vol. 51, No. 6. December 2004 and "Optical probing of a silicon integrated circuit using electric-field-induced second-harmonic generation," Applied Physics Letters 88, 114107, (2006), each of which publication is incorporated herein by reference in its entirety.

More specifically regarding FIGS. 19A and 19B, these figures illustrate an example for interrogating a Silicon-On-Insulator (SOI) device. In this example, a conductive chuck begins at a 'neutral' ground state, and bulk and device layers being at an equilibrium potential. At moment 'A', voltage applied to the chuck is changed rapidly, applying that voltage to the sample's conductive bulk layer. Since the sample's device layer is separated from the bulk by a thin buried oxide layer and not directly connected with a conductor, an electric potential field, or voltage will be induced between the device and bulk layers. Between times 'A' and B', the voltage applied to the chuck is not changed. Since the dielectric between the bulk and device layers is not perfect, the induced potential will drive a leakage current between the layers, causing the potential between the bulk and device layers to return to its natural state. This spike and decay in electric field is then monitored via SHG to provide insight to the leakage current. At time B' the voltage applied to the chuck is returned to ground, causing the voltage across the interface to reverse.

The systems and methods described herein can be used to characterize a sample (e.g., a semiconductor wafer or a portion thereof). For example, the systems and methods described herein can be used to detect defects or contaminants in the sample as discussed above. The systems and methods described herein can be configured to characterize the sample during fabrication or production of the semiconductor wafer. Thus, the systems and methods can be used along a semiconductor fabrication line in a semiconductor fabrication facility. The systems and methods described herein can be integrated with the semiconductor fabrication/production line. The systems and methods described herein can be integrated into a semiconductor fab line with automated wafer handling capabilities. For example, the system can be equipped with an attached Equipment Front End Module (EFEM), which accepts wafer cassettes such as a Front Opening Unified Pod (FOUP). Each of these cassettes can be delivered to the machine by human operators or by automated cassette-handling robots which move cassettes from process to process along fabrication/production line.

In various embodiments, the system can be configured such that once the cassettes are mounted on the EFEM, the FOUP is opened, and a robotic arm selects individual wafers from the FOUP and moves them through an automatically actuated door included in the system, into a light-tight process box, and onto a bias-capable vacuum chuck. The chuck may be designed to fit complementary with the robotic arm so that it may lay the sample on top. At some point in this process, the wafer can be held over a scanner for identification of its unique laser mark.

Accordingly, a system configured to be integrated in a semiconductor fabrication/assembly line can have automated wafer handling capability from the FOUP or other type of cassette; integration with an EFEM as discussed above, a chuck designed in a way to be compatible with robotic handling, automated light-tight doors which open and close to allow movement of the robotic wand/arm and software signaling to EFEM for wafer loading/unloading and wafer identification.

Variations

As described above each of Sections I, II, III, and IV of U.S. Provisional Application No. 61/980,860, filed on Apr. 17, 2014, titled "WAFER METROLOGY TECHNOLOGIES," are incorporated herein by reference in their entirety. Similarly, patent applications (i) U.S. patent application Ser. No. 14/690,179, filed Apr. 17, 2015 titled "PUMP AND PROBE TYPE SECOND HARMONIC GENERATION METROLOGY", published as U.S. Publication No. 2015/0330908, (ii) U.S. patent application Ser. No. 14/690,256, filed Apr. 17, 2015 titled "CHARGE DECAY MEASUREMENT SYSTEMS AND METHODS", published as U.S. Publication No. 2015/0331029, and (iii) U.S. patent application Ser. No. 14/690,251, filed Apr. 17, 2015 titled "FIELD-BIASED SECOND HARMONIC GENERATION METROLOGY", published as U.S. Publication No. 2015/0331036, are each incorporated herein by reference in their entirety. PCT Application No. PCT/US2015/026263, filed Apr. 16, 2015 titled "WAFER METROLOGY TECHNOLOGIES" is also incorporated herein by reference in its entirety. Accordingly, features from the disclosure of any of these documents incorporated by reference may be combined with any features recited elsewhere herein.

Example invention embodiments, together with details regarding a selection of features have been set forth above. As for other details, these may be appreciated in connection with the above-referenced patents and publications as well as is generally known or appreciated by those with skill in the art. The same may hold true with respect to method-based aspects of the invention in terms of additional acts as commonly or logically employed. Regarding such methods, including methods of manufacture and use, these may be carried out in any order of the events which is logically possible, as well as any recited order of events. Furthermore, where a range of values is provided, it is understood that every intervening value, between the upper and lower limit of that range and any other stated or intervening value in the stated range is encompassed within the invention. Also, it is contemplated that any optional feature of the inventive variations described may be set forth and claimed independently, or in combination with any one or more of the features described herein.

As used herein, a phrase referring to "at least one of" a list of items refers to any combination of those items, including single members. As an example, "at least one of: a, b, or c" is intended to cover: a, b, c, a-b, a-c, b-c, and a-b-c.

Though the invention embodiments have been described in reference to several examples, optionally incorporating various features, they are not to be limited to that which is described or indicated as contemplated with respect to each such variation. Changes may be made to any such invention embodiment described and equivalents (whether recited herein or not included for the sake of some brevity) may be substituted without departing from the true spirit and scope hereof. Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The various illustrative processes described may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, DisplayPort, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An example storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more example embodiments, the functions described may be implemented in hardware, software, firmware, or any combination thereof. If implemented in software, the functions may be stored on, transmitted over or resulting analysis/calculation data output as one or more instructions, code or other information on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices.

Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Operations as described herein can be carried out on or over a website. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

Also, the inventors hereof intend that only those claims which use the words "means for" are to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

It is also noted that all features, elements, components, functions, acts and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and acts or steps from different embodiments, or that substitute features, elements, components, functions, and acts or steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In some instances entities are described herein as being coupled to other entities. It should be understood that the terms "interfit", "coupled" or "connected" (or any of these forms) may be used interchangeably herein and are generic to the direct coupling of two entities (without any non-negligible, e.g., parasitic, intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

Reference to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below.

It is further noted that the claims may be drafted to exclude any optional element (e.g., elements designated as such by description herein a "typical," that "can" or "may" be used, etc.). Accordingly, this statement is intended to serve as antecedent basis for use of such exclusive terminology as "solely," "only" and the like in connection with the recitation of claim elements, or other use of a "negative" claim limitation language. Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Yet, it is contemplated that any such "comprising" term in the claims may be amended to exclusive-type "consisting" language. Also, except as specifically defined herein, all technical and scientific terms used herein are to be given as broad a commonly understood meaning to those skilled in the art as possible while maintaining claim validity.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, acts, steps, or elements of the embodiments may be recited in or added to the claims, as well as negative limitations (as referenced above, or otherwise) that define the inventive scope of the claims by features, functions, steps, or elements that are not within that scope. Thus, the breadth of the inventive variations or invention embodiments are not to be limited to the examples provided, but only by the scope of the following claim language.

That being said, we claim:

1. A system for optically interrogating a surface, comprising
    a pump optical source configured to emit pumping radiation, the pumping radiation having an average optical pump power;
    a probe optical source configured to emit probing radiation, the probing radiation having an average optical probe power less than the average optical pump power;
    at least one optical detector configured to detect second harmonic generated light generated by at least one of the pumping radiation or the probing radiation, the second harmonic generated light being generated by a semiconductor wafer whose surface is to be interrogated;

at least one of a shutter, a modulator or a variable optical path that is configured to introduce a variable time offset between the pumping and the probing radiation; and a processor configured to determine a characteristic of the detected second harmonic generated light, wherein the system is configured to obtain a time dependence of the detected second harmonic generated light in less than 10 seconds after applying at least one of the pumping radiation and the probing radiation.

2. The system of claim 1, wherein the pump optical source comprises a UV flash lamp.

3. The system of claim 1, wherein the pump optical source comprises a laser.

4. The system of claim 3, wherein the pump optical source comprises a pulsed laser.

5. The system of claim 4, wherein the pulsed laser is selected from a group consisting of nanosecond, picosecond and femtosecond lasers.

6. The system of claim 4, wherein the pulsed laser comprises a wavelength tunable laser.

7. The system of claim 1, wherein the probe optical source comprises a pulsed laser.

8. The system of claim 1, wherein the optical detector is selected from a photomultiplier tube, a CCD camera, an avalanche detector, a photodiode detector, a streak camera and a silicon detector.

9. The system of claim 8, wherein the system is configured to obtain the second harmonic generated light in less than 1 second after applying at least one of the pumping radiation and the probing radiation.

10. The system of claim 1, wherein the system comprises the variable optical path that is configured to introduce a variable time offset between the pumping and the probing radiation.

11. The system of claim 10, wherein the variable optical path is a programmable optical delay.

12. The system of claim 1, wherein the shutter is an optical shutter selected from a Kerr cell and a Pockels cell.

13. The system of claim 1, wherein the shutter is a mechanical shutter.

14. The system of claim 1, wherein the shutter is configured to introduce a time offset between about 1 millisecond and about 60 seconds.

15. The system of claim 1, wherein the processor is configured to obtain a time dependence of the detected second harmonic generated light in less than 10 seconds after applying at least one of the pumping radiation and the probing radiation.

16. The system of claim 1, wherein the processor is configured to determine a characteristic of the detected second harmonic generated light including a reduction in intensity of the detected second harmonic generated light in the presence of pumping energy.

17. The system of claim 1, wherein the processor is configured to determine a characteristic of the detected second harmonic generated light including an increase in intensity of the detected second harmonic generated light in the presence of pumping energy.

18. The system of claim 1, wherein the variable optical path comprises an optical delay line.

19. The system of claim 18, wherein the optical delay line comprises at least one of a fiber-based device, a mirror-based device, a plurality of set-time delay lines, or a variable delay line.

20. The system of claim 1, wherein the processor is further configured to determine a characteristic of the surface based on the detected second harmonic generated light and the variable time offset.

21. The system of claim 1, wherein the average optical pump power is less than 10 W.

22. The system of claim 1, wherein the average optical probe power is less than 150 mW.

23. The system of claim 1, wherein the pumping radiation comprises a plurality of optical pulses having a peak optical pump power, and wherein the probing radiation comprises a plurality of optical pulses having a peak optical probe power greater than the peak optical pump power.

24. A system for optically interrogating a surface, comprising:

a pump optical source configured to emit pumping radiation, the pumping radiation having an average optical pump power;

a probe optical source configured to emit probing radiation, the probing radiation having an average optical probe power less than the average optical pump power;

at least one optical detector configured to detect second harmonic generated light generated by at least one of the pumping radiation or the probing radiation, the second harmonic generated light being generated by a semiconductor wafer whose surface is to be interrogated; and a controller configured to obtain information regarding time dependence of the detected second harmonic generated light produced in less than 10 seconds after applying at least one of the pumping radiation and the probing radiation.

25. The system of claim 24, wherein the average optical pump power is less than 10 W.

26. The system of claim 24, wherein the average optical probe power is less than 150 mW.

27. The system of claim 24, wherein the pumping radiation comprises a plurality of optical pulses having a peak optical pump power, and wherein the probing radiation comprises a plurality of optical pulses having a peak optical probe power greater than the peak optical pump power.

28. A system for optically interrogating a surface, comprising a pump optical source configured to emit pumping radiation with variable energy, the pumping radiation having an average optical pump power;

a probe optical source configured to emit probing radiation, the probing radiation having an average optical probe power less than the average optical pump power;

an optical detector configured to detect second harmonic generated light generated by at least one of the pumping radiation or the probing radiation, the second harmonic generated light being generated by a semiconductor wafer whose surface is to be interrogated; and processing electronics configured to:

obtain information regarding time dependence of the detected second harmonic generated light generated less than 10 seconds after applying at least one of the pumping radiation and the probing radiation; and detect a region of discontinuity in the second harmonic generated light to determine threshold injection carrier energy as the energy of the pumping radiation is varied.

29. The system of claim 28, wherein the intensity of the second harmonic generated light increases as the energy of the pumping radiation increases after the region of discontinuity.

30. The system of claim 28, wherein the average optical pump power is less than 10 W.

31. The system of claim 28, wherein the average optical probe power is less than 150 mW.

32. The system of claim 28, wherein the pumping radiation comprises a plurality of optical pulses having a peak optical pump power, and wherein the probing radiation comprises a plurality of optical pulses having a peak optical probe power greater than the peak optical pump power.

* * * * *